US012385074B2

(12) United States Patent
Stoynova et al.

(10) Patent No.: US 12,385,074 B2
(45) Date of Patent: Aug. 12, 2025

(54) METHOD OF PRODUCING L-AMINO ACIDS

(71) Applicant: AJINOMOTO CO., INC., Tokyo (JP)

(72) Inventors: Natalia Viktorovna Stoynova, Moscow (RU); Olga Nikolaevna Igonina, Moscow (RU); Evgeniya Aleksandrovna Malykh, Moscow (RU); Natalya Sergeevna Plekhanova, Moscow (RU); Irena Alexandrovna Kononova, Moscow (RU); Ivan Alexandrovich Butov, Moscow (RU); Viktor Vasilievich Samsonov, Moscow (RU); Irina Vladimirovna Biryukova, Moscow (RU); Irina Segreevna Shmagina, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 827 days.

(21) Appl. No.: 17/486,357

(22) Filed: Sep. 27, 2021

(65) Prior Publication Data

US 2022/0010343 A1 Jan. 13, 2022

Related U.S. Application Data

(63) Continuation of application No. PCT/JP2020/015390, filed on Apr. 3, 2020.

(30) Foreign Application Priority Data

Apr. 5, 2019 (RU) ................................ 2019110100

(51) Int. Cl.
*C12P 13/04* (2006.01)
*C12P 13/08* (2006.01)
(Continued)

(52) U.S. Cl.
CPC ............... *C12P 13/04* (2013.01); *C12P 13/08* (2013.01); *C12P 13/12* (2013.01); *C12P 13/227* (2013.01); *C12P 13/24* (2013.01)

(58) Field of Classification Search
CPC ................................ C12P 19/04; C12P 13/04
See application file for complete search history.

(56) References Cited

U.S. PATENT DOCUMENTS 4,278,765 A 7/1981 Debabov et al.
4,346,170 A 8/1982 Sano et al.
(Continued)

FOREIGN PATENT DOCUMENTS

EP 0685555 A1 12/1995
WO WO95/16042 A1 6/1995
(Continued)

OTHER PUBLICATIONS

A0A080IDY1_ECOLX. UniProtKB/TrEMBL. Jun. 7, 2017.*
(Continued)

*Primary Examiner* — Yong D Pak
(74) *Attorney, Agent, or Firm* — Cermak & McGowan LLP; Shelly Guest Cermak

(57) ABSTRACT

A method is described for producing an L-amino acid including the steps of cultivating in a culture medium an L-amino acid-producing bacterium belonging to the family Enterobacteriaceae to produce and accumulate the L-amino acid in the culture medium, cells of the bacterium, or both, and collecting the L-amino acid from the culture medium, the cells, or both, wherein said bacterium has been modified to overexpress a gene encoding a periplasmic adaptor protein.

11 Claims, 6 Drawing Sheets

Specification includes a Sequence Listing.

(51) Int. Cl.

| | |
|---|---|
| ***C12P 13/12*** | (2006.01) |
| ***C12P 13/22*** | (2006.01) |
| ***C12P 13/24*** | (2006.01) |

(56) References Cited

U.S. PATENT DOCUMENTS

| | | | |
|---|---|---|---|
| 5,661,012 | A | 8/1997 | Sano et al. |
| 5,965,391 | A | 10/1999 | Reinscheid et al. |
| 6,040,160 | A | 3/2000 | Kojima et al. |
| 2006/0216796 | A1 | 9/2006 | Hashiguchi et al. |

FOREIGN PATENT DOCUMENTS

| | | | |
|---|---|---|---|
| WO | WO96/15246 | A1 | 5/1996 |
| WO | WO2008/032757 | A1 | 3/2008 |
| WO | WO2008/044714 | A1 | 4/2008 |

OTHER PUBLICATIONS

Fransceus . J Ind Microbiol Biotechnol. May 2017;44(4-5):687-695.*

Sanavia. Computational and Structural Biotechnology Journal, vol. 18, 2020, pp. 1968-1979.*

Du, D., et al., "Assembly and operation of bacterial tripartite multidrug efflux pumps," Trends Microbiol. 2015;23(5):311-319.

Leopold, S. R., et al., "A precise reconstruction of the emergence and constrained radiations of *Escherichia coli* O157 portrayed by backbone concatenomic analysis," PNAS 2009;106(21):8713-8718.

Database UniParc, Dec. 15, 2005, Database accession No. UPI000013B383, 3 pp.

Invitation to Pay Additional Fees and, Where Applicable, Protest Fee for PCT Patent App. No. PCT/JP2020/015390 (Jun. 22, 2020).

International Search Report and Written Opinion for PCT Patent App. No. PCT/JP2020/015390 (Aug. 13, 2020).

Symmons, M. F., et al., "Architecture and roles of periplasmic adaptor proteins in tripartite efflux assemblies," Frontiers Microbiol. 2015, vol. 6, Article 513, pp. 1-20.

Daley, D. O., et al., "Global Topology Analysis of the Escherichia coli Inner Membrane Proteome," Science 2005;308:1321-1323.

Notice of Reasons for Refusal (dated Feb. 6, 2024) for Japanese Patent Application No. 2021-559331 with English language translation thereof.

Database Uniprot, Accession No. P37636 [online], Feb. 13, 2019 [Search Date Jan. 29, 2024], Internet: URL:https://rest.uniprot.org/unisave/P37636?format=txt&versions= 134.

Database Uniprot, Accession No. P52599 [online], Feb. 13, 2019 [Search Date Jan. 29, 2024], Internet: URL:https://rest.uniprot.org/unisave/P52599?format=txt&versions= 125.

Database Uniprot, Accession No. P76397 [online], Feb. 13, 2019 [Search Date Jan. 29, 2024], Internet: URL:https://rest.uniprot.org/unisave/P76397?format=txt&versions= 132.

* cited by examiner

METHOD OF PRODUCING L-AMINO ACIDS

METHOD OF PRODUCING L-AMINO ACIDS

This application is a Continuation of, and claims priority under 35 U.S.C. § 120 to, International Application No. PCT/JP2020/015390, filed Apr. 3, 2020, and claims priority therethrough under 35 U.S.C. § 119 to Russian Patent Application No. 2019110100, filed Apr. 5, 2019, the entireties of which are incorporated by reference herein. Also, the Sequence Listing filed electronically herewith is hereby incorporated by reference (File name: 2021-09-27T_US-631_Seq_List; File size: 89 KB; Date recorded: Sep. 27, 2021).

BACKGROUND

Technical Field

The present invention relates generally to the microbiological industry, and specifically to a method for producing L-amino acids by fermentation of a bacterium which has been modified to overexpress a gene encoding a periplasmic adaptor protein, so that production of the L-amino acids is enhanced.

Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acids production yields have been reported, including transformation of microorganisms with recombinant DNA (see, for example, U.S. Pat. No. 4,278,765 A) and alteration of expression regulatory regions such as promoters, leader sequences, and/or attenuators, or others known to persons skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Structural understanding of the tripartite efflux assemblies in bacteria has advanced in recent years. These assemblies constitute a group of multidrug efflux and type I secretion systems, and are largely responsible for efflux and secretion of antibiotics and other toxic compounds out of cells. A tripartite efflux assembly includes three major components: the inner membrane protein ("IMP"), the outer membrane protein ("OMP"), and the periplasmic adaptor protein ("PAP"). The IMPs can be inner-membrane transporters belonging to the major facilitator superfamily ("MF S") proteins, the ATP-binding cassette ("ABC") group of proteins, and the resistance-nodulation-cell division ("RND") protein family (Symmons et al. (2015) Front. Microbiol., 6: 513). The OMPs, which are also referred to as outer membrane factors ("OMF"), can be outer membrane channels that are also known as porins.

The yibH gene has been reported to encode an inner membrane protein with two predicted transmembrane domains (Daley et al. (2005) Science, 308(5726): 1321-1323). The yibH gene, along with the yibI gene, constitutes the yibIH operon. The effect of overexpression of the yibH gene or overexpression of the yibIH operon genes in bacteria on production of L-amino acids by fermentation has not been previously reported.

SUMMARY

It is an aspect of the invention to provide a method for producing an L-amino acid comprising cultivating in a culture medium an L-amino acid-producing bacterium belonging to the family Enterobacteriaceae to produce and accumulate the L-amino acid in the culture medium, cells of the bacterium, or both, and collecting the L-amino acid from the culture medium, the cells, or both, wherein said bacterium has been modified to overexpress a gene encoding a periplasmic adaptor protein.

It is a further aspect of the present invention to provide the method as described above, wherein said gene is selected from the group consisting of (A) a gene selected from the group consisting of yibH, acrA, emrA, zneB, emrK, mdtA, mexA, macA, and mdtE; (B) a gene comprising a nucleotide sequence selected from the group consisting of SEQ ID NOS: 1, 3, 5, 7, 9, 11, 13, 15, and 17; C) a gene comprising a nucleotide sequence that is able to hybridize under stringent conditions with a nucleotide sequence complementary to a sequence selected from the group consisting of SEQ ID NOS: 1, 3, 5, 7, 9, 11, 13, 15, and 17; and wherein if the gene is overexpressed in the bacterium, the amount of the L-amino acid produced by the bacterium is increased as compared to that in a non-modified bacterium; (D) a gene having an identity of not less than 90% with respect to an entire nucleotide sequence selected from the group consisting of SEQ ID NOS: 1, 3, 5, 7, 9, 11, 13, 15, and 17; and wherein if the gene is overexpressed in the bacterium, the amount of the L-amino acid produced by the bacterium is increased as compared to that in a non-modified bacterium; (E) a gene comprising a variant nucleotide sequence selected from the group consisting of SEQ ID NOS: 1, 3, 5, 7, 9, 11, 13, 15, and 17, wherein the variant nucleotide sequence is due to the degeneracy of the genetic code; (F) a gene encoding a protein comprising an amino acid sequence selected from the group consisting of SEQ ID NOS: 2, 4, 6, 8, 10, 12, 14, 16, and 18; and wherein if the gene is overexpressed in the bacterium, the amount of the L-amino acid produced by the bacterium is increased as compared to that in a non-modified bacterium; (G) a gene encoding a protein comprising an amino acid sequence selected from the group consisting of SEQ ID NOS: 2, 4, 6, 8, 10, 12, 14, 16, and 18, but wherein said amino acid sequence includes substitution, deletion, insertion, and/or addition of one or several amino acid residues; and wherein if the gene is overexpressed in the bacterium, the amount of the L-amino acid produced by the bacterium is increased as compared to that in a non-modified bacterium; and (H) a gene encoding a protein comprising an amino acid sequence having an identity of not less than 90% with respect to the entire amino acid sequence selected from the group consisting of SEQ ID NOS: 2, 4, 6, 8, 10, 12, 14, 16, and 18; and wherein if the gene is overexpressed in the bacterium, the amount of the L-amino acid produced by the bacterium is increased as compared to that in a non-modified bacterium.

It is a further aspect of the present invention to provide the method as described above, wherein said gene is overexpressed by increasing the copy number of the gene, by modifying an expression regulatory region of the gene, or both; so that the expression of said gene is increased as compared with a non-modified bacterium.

It is a further aspect of the present invention to provide the method as described above, wherein said bacterium belongs to the genus *Escherichia* or *Pantoea*.

It is a further aspect of the present invention to provide the method as described above, wherein said bacterium is *Escherichia coli* or *Pantoea ananatis*.

It is a further aspect of the present invention to provide the method as described above, wherein said L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

It is a further aspect of the present invention to provide the method as described above, wherein said bacterium has been modified further to overexpress a gene encoding an inner membrane protein, to overexpress a gene encoding an outer membrane protein, or both.

It is a further aspect of the present invention to provide the method as described above, wherein said gene encoding an inner membrane protein is selected from the group consisting of rhtA, rhtB, rhtC, leuE, eamA, argO, eamB, ygaZH, yddG, cydDC, yjeH, alaE, yahN, and lysO; and wherein said gene encoding an outer membrane protein is selected from the group consisting of mdtP, tolC, and mdtQ.

It is a further aspect of the present invention to provide the method as described above, wherein said gene encoding an inner membrane protein is selected from the group consisting of leuE and yddG, and said gene encoding an outer membrane protein is tolC.

It is a further aspect of the present invention to provide the method as described above, wherein said bacterium has been modified further to overexpress a yibI gene.

It is a further aspect of the present invention to provide the method as described above, wherein said L-amino acid is selected from the group consisting of L-histidine, L-cysteine, L-valine, and L-tryptophan.

It is a further aspect of the present invention to provide the method as described above, wherein said L-amino acid is selected from the group consisting of L-histidine and L-tryptophan.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF DRAWINGS

The invention of the present application will now be described in more detail with reference to exemplary embodiments of the present invention, given only by way of example, and with reference to the accompanying drawings, in which.

DETAILED DESCRIPTION OF EXEMPLARY EMBODIMENTS

Figure 1:
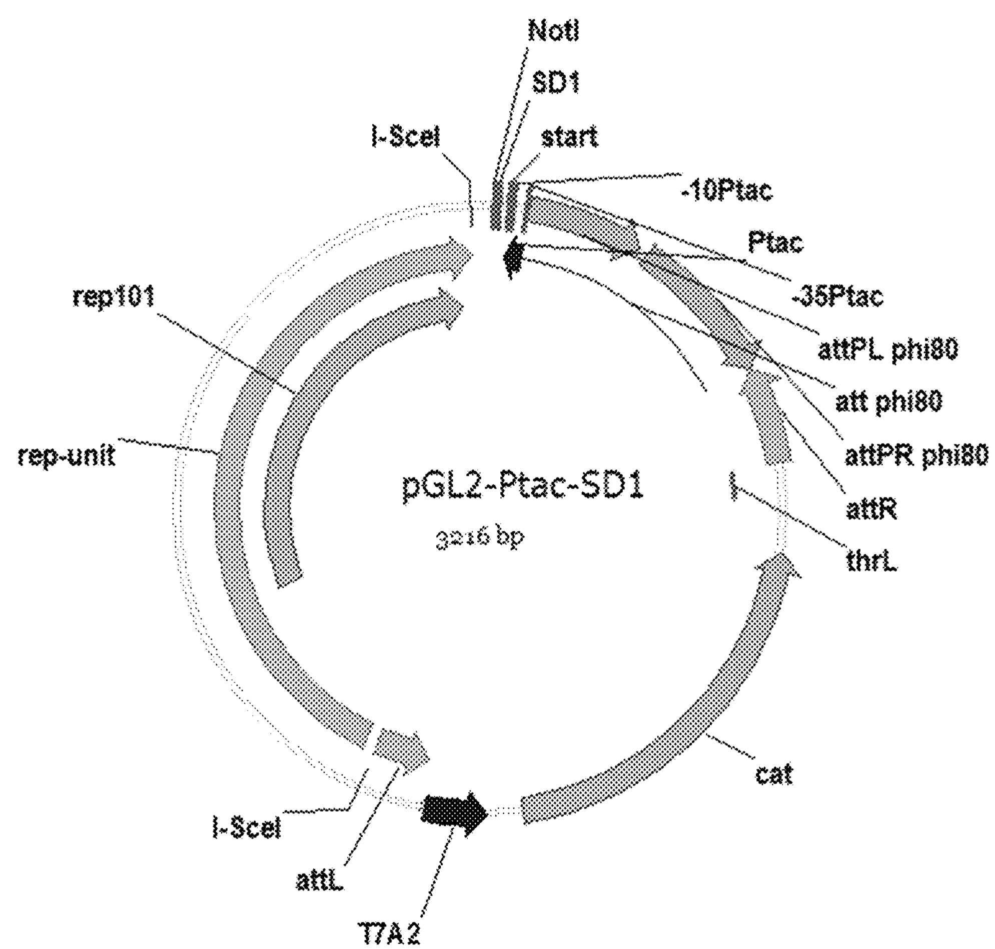
FIG. 1 illustrates the pGL2-$P_{tac}$-SD1 plasmid.

The method as described herein can include a method for producing an L-amino acid by fermentation of a bacterium. The method for producing L-amino acid can include the steps of cultivating the bacterium in a culture medium to produce and accumulate the L-amino acid in the culture medium or in cells of the bacterium (i.e. bacterial cells), or both, and collecting the L-amino acid from the culture medium and/or the bacterial cells. L-amino acid can be produced, for example, in a free form or as a salt thereof, or as a mixture thereof. A bacterium that has been modified to overexpress a gene encoding a periplasmic adaptor protein can be used in the method.

Periplasmic adaptor proteins (also referred to as "PAP") have been identified as a component in multidrug efflux pumps and type I secretion systems. In addition to the PAPs, these systems can also include inner membrane proteins (also referred to as "IMP") and outer membrane proteins (also referred to as "OMP"). The PAPs have been recently identified as playing active and diverse roles in the transport process. With the help of the PAPs, the IMPS are linked to the OMPs to create continuous conduits from the cytoplasm to the extracellular space, and forming the tripartite complex.

The YibH protein has now been identified for the first time as a PAP. The yibH gene encoding the YibH protein is located with the yibI gene, which encodes YibI protein with unknown function, on an yibIH operon. The structure of the YibH protein has now been identified as being similar to other known PAPs, including AcrA native to *Escherichia coli*, EmrA native to *Aquifex aeolicus*, ZneB native to *Cupriavidus metallidurans*, EmrK native to *Escherichia coli*, MdtA native to *Escherichia coli*, MexA native to *Pseudomonas aeruginosa*, MacA native to *Escherichia coli*, MdtE native to *Escherichia coli*, and to other known efflux pumps. Although less is known about the PAPs as compared to the other components of the tripartite complex, recent advances indicate that the PAPs are a critical component in the efflux and transport processes, including cargo recognition and selection, and control of energy flow. More importantly, the PAPs can link with multiple IMPs and multiple OMPs, making many variants of the tripartite pump system. Hence, the IMPs and OMPs used in the method as described herein are not limited, and include any IMP and/or OMP that can function with the chosen PAP in the tripartite pump system.

The IMPs that can be used in the method as described herein can include any known IMPs. Examples can include RhtA, RhtB (see EP10167710 B1; EP994190 A; Livshits et al. (2003) Res. Microbiol., 154(2): 123-135; Zakataeva et al. (2006) Microbiol., 75(4): 438-448), LeuE (also referred to as YeaS; see EP1016710 B1), EamA (see WO2012036151 A1), ArgO (see EP1580262 B1; Zakataeva et al. (2006)), EamB (see EP1016710 B1; Zakataeva et al. (2006)), YgaZH (see RU2215782 C2), YddG (see U.S. Pat. No. 7,666,655 B2; Doroshenko et al. (2007) FEMS Microbiol Lett., 275(2): 312-318), CydDC (see Cruz-Ramos et al. (2004) Microbiol., 150(Pt 10): 3415-3427), YjeH (see Liu et al. (2015) Appl Environ. Microbiol., 81(22): 7753-7766), AlaE (see Hori et al. (2011) Appl. Environ. Microbiol., 77(12): 4027-4034), YahN (see EP1016710 B1), and LysO (see WO2005073390

A2). The chosen IMP can be overexpressed in a bacterium that is used in the method, or the chosen IMP that is natively present in the chosen bacterial host can be used.

The OMPs that can be used in the method as described herein can include any known OMPs. Examples can include MdtP (see DE102008044768 A1), TolC (see U.S. Pat. No. 8,278,075 B2; Wiriyathanawudhiwong et al. (2009) Appl Microbiol Biotechnol., 81(5): 903-913; ecocyc.org/gene?orgid=ECOLI&id=EG11009), and MdtQ (ecocyc.org/gene?orgid=ECOLI&id=EG12020). TolC is a particular example. The chosen OMP can be overexpressed in a bacterium that is used in the method, or the chosen OMP that is natively present in the chosen bacterial host can be used.

The bacterium used in the method as described herein can be modified so that the activity of the PAP is increased, the activity of the IMP is increased, and/or the activity of the OMP is increased. The activity of the PAP, IMP, or OMP can be increased by overexpressing a gene encoding the PAP, IMP, or OMP gene. A gene encoding the PAP, IMP, or OMP can also be referred to as "PAP gene", "IMP gene", or "OMP gene", respectively. Hence, the phrase "a bacterium is modified so that the activity of PAP, IMP, or OMP is increased" can mean that the bacterium is modified to overexpress a PAP, IMP, or OMP gene. The phrase "overexpression of PAP, IMP, or OMP gene" may be used interchangeably or equivalently with the phrase "overexpression of PAP, IMP, or OMP". By modifying a bacterium so that at least the activity of the PAP is increased, L-amino acid production by the bacterium can be improved. In a particular example, by modifying a bacterium in which the activity of the PAP is increased, so that the activity of the IMP and/or the activity of the OMP is/are increased, L-amino acid production by the bacterium can be further improved. As it is shown in the non-limiting Examples section herein, simultaneous overexpression of IMP LeuE (also known in the art as YeaS) or YddG, OMP TolC, and the putative PAP YibH, can result in increased production of several L-amino acids, including L-histidine, L-cysteine, L-valine, and L-tryptophan, by the L-amino acid-producing bacterial strains in which they were overexpressed. Hence, overexpression of one, two, or all three of these proteins in one cell can increase efflux of the objective L-amino acid(s) into the medium and therefore can lead to better fermentation performance.

The bacterium can be obtained by modifying a bacterium having an L-amino acid-producing ability so that the activity of the PAP is increased, the activity of the IMP is increased, and/or the activity of the OMP is increased. Furthermore, the bacterium can also be obtained by modifying a bacterium so that the activity of the PAP is increased, the activity of the IMP is increased, and/or the activity of the OMP is increased, and then imparting an L-amino acid producing ability to the bacterium or enhancing L-amino acid-producing ability of the bacterium. The bacterium may also acquire an L-amino acid-producing ability by being modified so that the activity of the PAP is increased, the activity of the IMP is increased, and/or the activity of the OMP is increased. The modifications for constructing the bacterium can be performed in any order.

Any PAP can be used in the method as described herein so long as the PAP can form a tripartite efflux pump with the chosen IMP and the chosen OMP so that the tripartite efflux pump is able to export, efflux and/or secrete, or the like, an objective substance out of cells of the bacterium that can be used in the method as described herein. That is, any PAP can be used in the method as described herein so long as the PAP has an activity for functioning in a tripartite efflux pump that includes the chosen IMP and the chosen OMP so that the tripartite efflux pump can have a transporting activity towards the objective substance. Examples of the objective substance can include L-amino acids. Examples of the PAP can include YibH, AcrA, EmrA, ZneB, EmrK, MdtA, MexA, MacA, and MdtE, which are encoded by yibH, acrA, emrA, zneB, emrK, mdtA, mexA, macA, and mdtE genes, respectively. Specific examples of the PAP can include the YibH native to *Escherichia coli* (SEQ ID NO: 2), AcrA native to *Escherichia coli* (SEQ ID NO: 4), EmrA native to *Aquifex aeolicus* (SEQ ID NO: 6), ZneB native to *Cupriavidus metallidurans* (SEQ ID NO: 8), EmrK native to *Escherichia coli* (SEQ ID NO: 10), MdtA native to *Escherichia coli* (SEQ ID NO: 12), MexA native to *Pseudomonas aeruginosa* (SEQ ID NO: 14), MacA native to *Escherichia coli* (SEQ ID NO: 16), and MdtE native to *Escherichia coli* (SEQ ID NO: 18), which are encoded by the yibH (SEQ ID NO: 1), acrA (SEQ ID NO: 3), emrA (SEQ ID NO: 5), zneB (SEQ ID NO: 7), emrK (SEQ ID NO: 9), mdtA (SEQ ID NO: 11), mexA (SEQ ID NO: 13), macA (SEQ ID NO: 15), and mdtE (SEQ ID NO: 17) genes, respectively.

Any IMP can be used in the method as described herein so long as the IMP can form a tripartite efflux pump with the chosen PAP and the chosen OMP so that the tripartite efflux pump is able to export, efflux and/or secrete, or the like, an objective substance out of cells of the bacterium that can be used in the method. That is, any IMP can be used in the method as described herein so long as the IMP has an activity for functioning in a tripartite efflux pump that includes the chosen PAP and the chosen OMP so that the tripartite efflux pump can have a transporting activity towards the objective substance. An IMP can be appropriately selected depending on the objective substance which is exported, effluxed, and/or secreted out of the cells by means of the tripartite efflux pump that includes the IMP. Also, an IMP can be appropriately selected depending on the objective substance which is produced using the method as described herein. For example, when the objective substance is an L-amino acid, the IMP can be a protein having an L-amino acid-transporting activity for the objective L-amino acid. It is therefore acceptable that the IMP that can be used in the method as described herein can be an IMP having an L-amino acid-transporting activity and can form a tripartite efflux pump with the chosen PAP and the chosen OMP so that the tripartite efflux pump that includes the IMP is able to export, efflux and/or secrete, or the like, the L-amino acid out of cells of the bacterium that can be used in the method. Moreover, the IMP that can be used in the method as described herein can be an IMP having an ability to transport more than one substance such as, for example, more than one L-amino acid, that is, different substances such as different L-amino acids. It is well-known to the person skilled in the art that the IMP can have the ability to transport more than one substance such as, for example, different kinds of L-amino acids. For example, a LeuE protein (also known in the art as YeaS) which is encoded by the leuE gene (also known in the art as yeaS) and that can be used in the method as described herein can be the IMP that can transport different kinds of L-amino acids such as, for example, L-histidine, L-methionine, and L-leucine (Kutukova et al. (2005), FEBS Lett., 579(21): 4629-4634). In another example, a YddG protein which is encoded by the yddG gene and that can be used in the method as described herein can be the IMP that can transport different kinds of aromatic L-amino acids such as, for example, L-tryptophan, L-phenylalanine, and L-tyrosine (Doroshenko et al. (2007), FEMS Microbiol Lett., 275(2): 312-318). That is, examples of the IMP that can be used can include the LeuE protein (also known in the art as YeaS) which is encoded by the leuE gene and the YddG protein which is encoded by the yddG gene. Other examples of the IMP that can be used can include RhtA, RhtB, RhtC, EamA, ArgO, EamB, YgaZH, CydDC, YjeH, AlaE, YahN, and LysO, which are encoded by the rhtA, rhtB, rhtC, eamA, argO, eamB, ygaZH, cydDC, yjeH, alaE, yahN, and lysO genes, respectively.

Any OMP can be used in the method as described herein so long as the OMP can form a tripartite efflux pump with the chosen PAP and the chosen IMP so that the tripartite efflux pump is able to export, efflux, and/or secrete, or the like, an objective substance out of cells of the bacterium that can be used in the method. That is, any OMP can be used in the method as described herein so long as the OMP has an activity for functioning in a tripartite efflux pump that includes the chosen PAP and the chosen IMP so that the tripartite efflux pump can have a transporting activity towards the objective substance. Examples of the OMP can include MdtP, TolC, and MdtQ, which are encoded by the mdtP, tolC, and mdtQ genes, respectively.

The terms "tripartite efflux pump", "tripartite pump system", "tripartite efflux complex", "tripartite complex", and "tripartite efflux assembly" can be used interchangeably or equivalently.

Methods are known that can be used to determine whether the chosen protein can form a complex with, that is can assemble with, one or more other proteins (see, for example, Miteva et al. (2013) Anal Chem., 85(2): 749-768; von Mering et al. (2007) Nucleic Acids Res., 35(Database issue): D358-62). In particular, a method for the assembling a tripartite efflux pump in vitro using proteoliposomes that mimic the dual-membrane architecture of Gram-negative bacteria was described in detail (Verchere et al. (2015) Nat Commun., 6: 6890; Verchere et al. (2014) J Vis Exp. (84): e50894). A method for expression of a tripartite efflux pump in vivo can also be used (Srikumar et al. (1998) Antimicrob Agents Chemother., 42(1): 65-71; Du et al. (2018) Methods Mol Biol., 1700: 71-81). The transporting activity of a tripartite efflux pump towards the objective substance can be determined using, for example, a method in which the transporting activity of a tripartite efflux pump that is assembled in vitro using proteoliposomes can be determined (Verchere et al. (2014); Verchere et al. (2015)). A transporting activity of the IMP can be determined using known methods that can be used to determine a transporting activity of a transporter protein (see, for example, Lee et al. (1975) J. Bacteriol., 122(3): 1001-1005; Ghrist et al. (1995) Microbiol., 141(Pt 1): 133-140; Doroshenko et al. (2007) FEMS Microbiol. Lett., 275(2): 312-318; Livshits et al. (2003) Res. Microbiol., 154(2): 123-135; and so forth).

The protein concentration can be determined by the Bradford protein assay or the method of Lowry using bovine serum albumin (BSA) as a standard and a Coomassie dye (Bradford (1976) Anal. Biochem., 72: 248-254; Lowry et al. (1951) J. Biol. Chem., 193: 265-275).

Examples of the PAP, IMP, and OMP can include, for example, PAP, IMP, and OMP proteins native to various bacteria including bacteria belonging to the family Enterobacteriaceae such as *Escherichia coli* (hereinafter *E. coli*) and *Pantoea ananatis* (hereinafter *P. ananatis*) and other bacteria described for PAP. The amino acid sequences of PAP, IMP, and OMP proteins native to various bacteria and the nucleotide sequences of genes encoding them can be obtained from, for example, databases such as NCBI.

The yibH gene of the *E. coli* K-12 MG1655 (ATCC 47076) strain corresponds to the sequence of the positions from 3770243 to 3771379 (complement) in the genome sequence registered at the NCBI database as Gene ID: 948110. The YibH protein of the MG1655 strain is registered at the NCBI as NCBI Reference Sequence: NP_418054.1. The nucleotide sequence of the yibH gene and the amino acid sequence of the YibH protein of the MG1655 strain are shown as SEQ ID NOs: 1 and 2, respectively. The yibH gene encoding the YibH protein is located with the yibI gene (SEQ ID NO: 57), which encodes YibI protein (SEQ ID NO: 58) with unknown function, on an yibIH operon. The bacterium can be modified further to overexpress the yibI gene.

Figure 4:
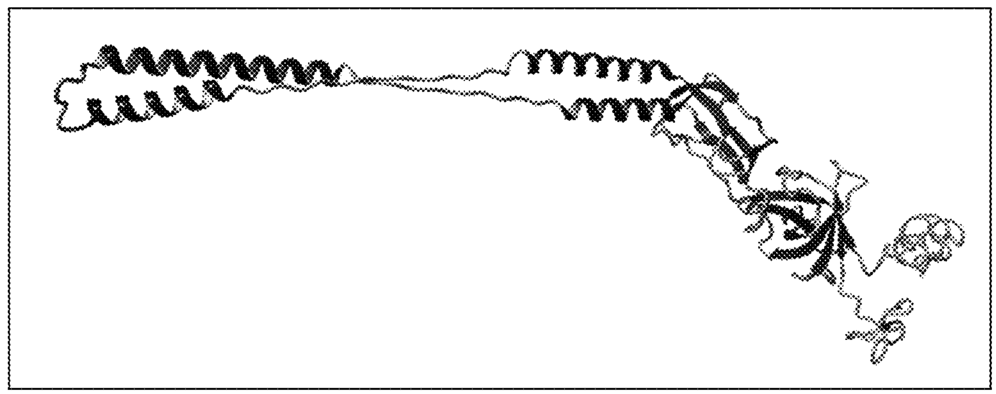
FIG. 4 illustrates the predicted structure by I-TASSER for YibH native to *E. col.*
Figure 5:
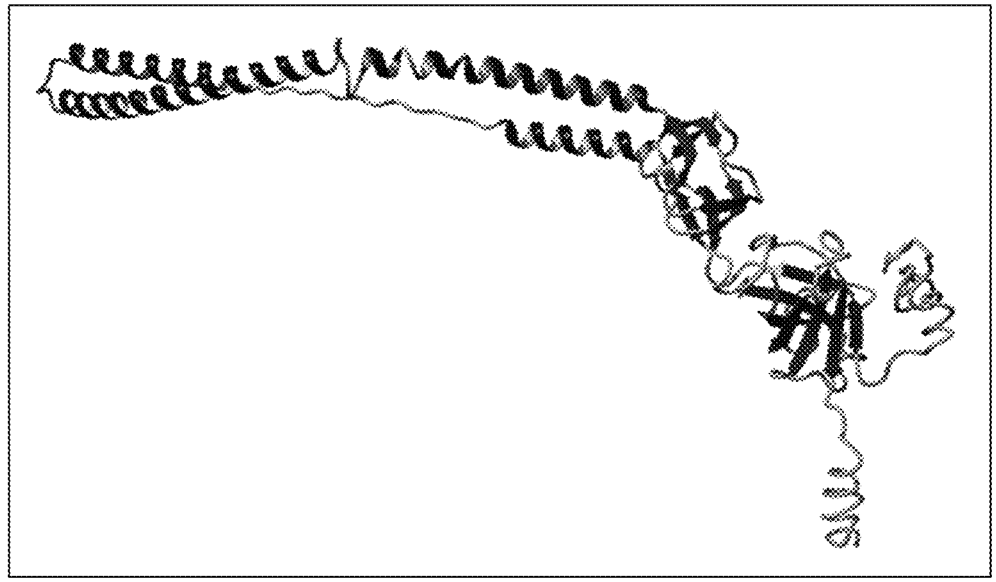
FIG. 5 illustrates the predicted structure by I-TASSER for a putative PAP native to *P. ananatis* having NCBI reference sequence No. WP_014594151.1.
Figure 6:
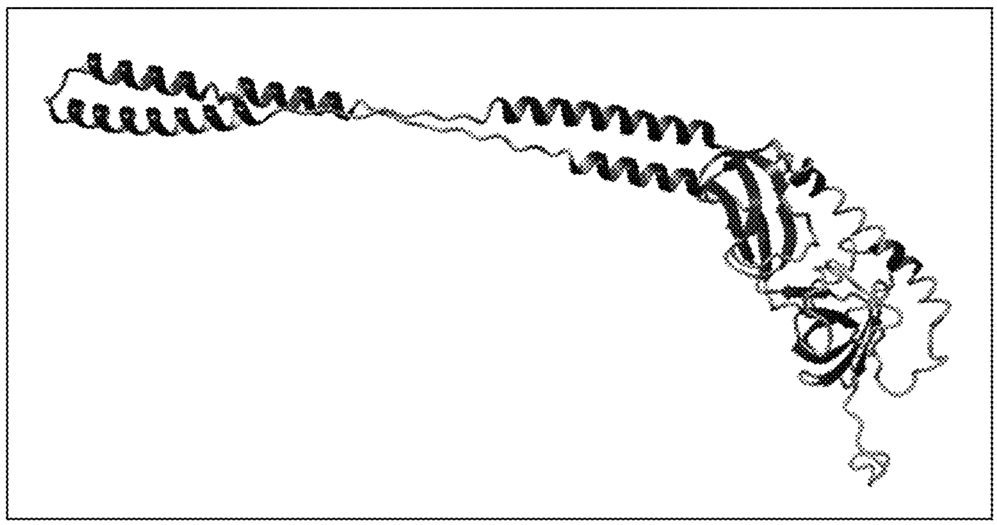
FIG. 6 illustrates the predicted structure by I-TASSER for a putative PAP native to *P. ananatis* having NCBI reference sequence No. WP_014593401.1.

The tertiary structure of YibH native to *E. coli* is similar to the structures of known established PAPs such as, for example, AcrA native to *E. coli* (PDB structure—2F1M.pdb), EmrA native to *Aquifex aeolicus* (4TKO.pdb), and MacA native to *E. coli* (3FPP.pdb) and *Actinobacillus actinomycetemcomitans* (4DK0.pdb) (Symmons et al. (2015) Front. Microbiol., 6: 513). Evaluative models of YibH native to *E. coli* and other putative PAPs native to *P. ananatis* have been generated using homology modeling with I-TASSER (see FIGS. 4 to 6). AcrA and a few other known adaptor proteins (Symmons et al. (2005)) were recognized by I-TASSER as structurally close to YibH native to *E. coli* and other putative PAPs native to *P. ananatis*.

From this modeling, it was determined that the tertiary structure of YibH native to *E. coli* contains an α-hairpin domain, which is responsible for the interactions with OMP likewise for other PAPs. Recognition between the PAP and OMP is essential for assembling tripartite complexes and their function. Other YibH domains are biotinyl/lipoyl carrier domain, β-barrel domain and N-terminal transmembrane domain. In other PAPs, these domains play an important role in stabilizing the complex assembly, anchoring to the inner membrane and interaction with IMP.

The PAP gene may be, for example, a gene having the nucleotide sequence shown as SEQ ID NO: 1, 3, 5, 7, 9, 11, 13, 15, or 17. Also, the PAP may be, for example, a protein having the amino acid sequence shown as SEQ ID NO: 2, 4, 6, 8, 10, 12, 14, 16, or 18. The phrase "a gene or protein has a nucleotide or amino acid sequence" can mean that the gene or protein is included as a part of a larger nucleotide or amino acid sequence, and can also mean that the gene or protein is only the nucleotide or amino acid sequence.

The PAP, IMP, and/or OMP proteins may be a variant of any of the proteins as specified above, so long as the original function thereof is maintained or the three-dimensional structure of the protein is not significantly changed relative to the non-modified protein such as, for example, the wild-type protein. Similarly, the genes encoding the PAP, IMP, and/or OMP proteins may be a variant of any of the PAP, IMP, and/or OMP genes exemplified above, so long as the original function thereof is maintained or the three-dimensional structure thereof is not significantly changed relative to the non-modified protein such as, for example, the wild-type protein. Such a variant that maintains the original function or the three-dimensional structure can also be referred to as a "conservative variant". Examples of the conservative variants can include, for example, homologues and artificially modified versions of the PAP, IMP, and/or OMP proteins described above and genes encoding them.

The terms "PAP protein", "IMP protein", and "OMP protein" include not only the PAP proteins, IMP proteins, and OMP proteins exemplified above, respectively, but also can include respective conservative variants thereof. Similarly, the terms "PAP gene", "IMP gene", and "OMP gene" include not only the PAP gene, IMP gene, and OMP gene exemplified above, but also can include respective conservative variants thereof. In addition, genes defined with the above-mentioned gene names and proteins defined with the above-mentioned protein names can include not only the genes and proteins exemplified above, respectively, but can also include respective conservative variants thereof. That is, for example, the term "yibH gene" can include not only the yibH gene exemplified above, such as the yibH gene having the nucleotide sequence shown as SEQ ID NO: 1, but can also include conservative variants thereof. Similarly, for example, the term "YibH protein" can include not only the YibH protein exemplified above, such as the YibH protein having the amino acid sequence shown as SEQ ID NO: 2, but can also include conservative variants thereof.

The phrase "the original function is maintained" can mean that a variant of gene or a variant of protein has a function such as activity or property corresponding to the function of the original gene or protein. That is, the expression "the original function is maintained" used for the PAP gene, IMP gene, and OMP gene can mean that a variant of the gene encode a protein having the PAP activity, a protein having the IMP activity, and a protein having the OMP activity, respectively. Also, the expression "the original function is maintained" used for the PAP protein, IMP protein, and OMP protein can mean that a variant of the protein has the PAP activity, the IMP activity, and the OMP activity, respectively. The phrase "PAP activity" can refer to an activity for functioning in a tripartite efflux pump that includes a chosen IMP and a chosen OMP so that the tripartite efflux pump can have a transporting activity towards an objective substance. The phrase "IMP activity" can refer to an activity for functioning in a tripartite efflux pump that includes a chosen PAP and a chosen OMP so that the tripartite efflux pump can have a transporting activity towards an objective substance. The phrase "OMP activity" can refer to an activity for functioning in a tripartite efflux pump that includes a chosen PAP and a chosen IMP so that the tripartite efflux pump can have a transporting activity towards an objective substance. Also, the expression "the original function is maintained" used for the PAP gene can mean that if a variant of the gene is overexpressed in the bacterium, the amount of the L-amino acid produced by the bacterium is increased as compared to that in a non-modified bacterium. Also, the expression "the original function is maintained" used for the PAP protein can mean that if a variant of the protein is overexpressed in the bacterium, the amount of the L-amino acid produced by the bacterium is increased as compared to that in a non-modified bacterium. Hereafter, examples of the conservative variants will be described.

Examples of homologues of PAP, IMP, and/or OMP proteins can include, for example, proteins that can be obtained from public databases by BLAST search or FASTA search (see, for example, ncbi.nlm.nih.gov) using any of the aforementioned amino acid sequences as a query sequence. Furthermore, homologues of the PAP, IMP, and/or OMP genes can be obtained by, for example, PCR (polymerase chain reaction; refer to White et al. (1989) Trends Genet., 5: 185-189) using a chromosomal DNA of various microorganisms as the template, and oligonucleotides prepared on the basis of any of the aforementioned nucleotide sequences as oligonucleotide primers.

The PAP, IMP, and/or OMP proteins may have any of the aforementioned amino acid sequences, but wherein the sequence includes substitution, deletion, insertion, and/or addition of one or several amino acid residues at one or several positions, so long as the original function is maintained or the three-dimensional structure of the protein is not significantly changed relative to the non-modified protein such as, for example, the wild-type protein. Although the amount intended by the phrase "one or several" may differ depending on the positions of amino acid residues in the three-dimensional structure of the protein or the types of amino acid residues, specifically, it can be, for example, 1 to 50, 1 to 40, 1 to 30, 1 to 20, 1 to 10, 1 to 5, or 1 to 3.

The aforementioned substitution, deletion, insertion, and/or addition of one or several amino acid residues can be a conservative mutation(s) that maintain(s) the function that is similar to the wild-type protein. Typical examples of the conservative mutation are conservative substitutions. The conservative substitution is a mutation wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Furthermore, such substitution, deletion, insertion, addition, or the like of amino acid residues as mentioned above includes a naturally occurring mutation due to an individual difference, or a difference of species of the organism from which the protein is native or derived.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence, and so long as the original function of the PAP, IMP, and/or OMP proteins is maintained or the three-dimensional structure of the protein is not significantly changed relative to the non-modified protein such as, for example, the wild-type protein.

The PAP, IMP, and/or OMP proteins may be a protein having an amino acid sequence having homology, defined as the parameter "identity" when using the computer program blastp, of, for example, 70% or more, 80% or more, 90% or more, 95% or more, 97% or more, 99% or more, to the total amino acid sequence of any of the aforementioned amino acid sequences, so long as the original function is maintained or the three-dimensional structure of the protein is not significantly changed relative to the non-modified protein such as, for example, the wild-type protein.

The PAP, IMP, and/or OMP proteins may be encoded by a DNA that is able to hybridize under stringent conditions with a probe that can be prepared from any of the aforementioned nucleotide sequences, such as a sequence complementary to a partial or entire sequence of any of the aforementioned nucleotide sequences, so long as the original function of the protein encoded by the DNA is maintained. The "stringent conditions" can refer to conditions under which a so-called specific hybrid is formed, and a non-specific hybrid is not formed. Examples of the stringent conditions can include those conditions under which a specific hybrid, for example, a hybrid having homology, defined as the parameter "identity" when using the computer program blastn, of, for example, not less than 70%, not less than 80%, not less than 90%, not less than 95%, not less than 97%, or not less than 99% is formed, and a non-specific hybrid, for example, a hybrid having homology lower than the above is not formed. For example, stringent conditions can be exemplified by washing one time, or 2 or 3 times, at a salt concentration and temperature corresponding to 1×SSC (standard sodium citrate or standard sodium chloride), 0.1% SDS at 60° C. (sodium dodecyl sulphate), 0.1×SSC, 0.1% SDS at 60° C., or 0.1×SSC, 0.1% SDS at 68° C. Furthermore, for example, when a DNA fragment having a length of about 300 bp is used as the probe, the washing conditions of the hybridization may be, for example, 2×SSC and 0.1% SDS at 50° C. Duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. A probe can be prepared by PCR (White et al. (1989)) using oligonucleotides as primers prepared on the basis of the DNA encoding the PAP, IMP, or OMP protein and a DNA fragment containing the nucleotide sequence as a template.

The calculation of a percent identity of a polypeptide can be carried out using the algorithm blastp. More specifically, the calculation of a percent identity of a polypeptide can be carried out using the algorithm blastp in the default settings of Scoring Parameters (Matrix: BLOSUM62; Gap Costs: Existence=11 Extension=1; Compositional Adjustments: Conditional compositional score matrix adjustment) provided by National Center for Biotechnology Information (NCBI). The calculation of a percent identity of a polynucleotide can be carried out using the algorithm blastn. More specifically, the calculation of a percent identity of a polynucleotide can be carried out using the algorithm blastn in the default settings of Scoring Parameters (Match/Mismatch Scores=1, −2; Gap Costs=Linear) provided by NCBI.

The sequence identity between two sequences can be calculated as the ratio of residues matching in the two sequences when aligning the two sequences so as to fit maximally with each other.

Furthermore, since the degeneracy of codons can differ depending on the host, any codons in the PAP, IMP, and/or OMP gene(s) may be replaced with respective equivalent codons according to the standard genetic code table (see, e.g., Lewin B., "Genes VIII", 2004, Pearson Education, Inc., Upper Saddle River, NJ 07458). For example, the PAP, IMP, and/or OMP gene(s) may be modified so that it has optimal codons according to codon frequencies in the chosen host.

The aforementioned descriptions concerning conservative variants of the genes and proteins can be applied mutatis mutandis to variants of any proteins such as, for example, the YibH protein and L-amino acid biosynthesis pathway enzymes and genes encoding them.

Bacterium

The phrase "an L-amino acid-producing bacterium" can be used interchangeably or equivalently to the phrase "a bacterium that is able to produce an L-amino acid" or the phrase "a bacterium having an ability to produce an L-amino acid".

The phrase "an L-amino acid-producing bacterium" can refer to a bacterium having an ability to generate or produce, and accumulate an objective L-amino acid in a medium or cells of the bacterium to such a degree that the L-amino acid can be collected, when the bacterium is cultured in the medium. The bacterium having an L-amino acid-producing ability may be able to accumulate an objective L-amino acid in a medium in an amount larger than that obtainable with a non-modified strain. The phrase "a non-modified strain" may be used interchangeably or equivalently to the phrase "a non-modified bacterium". The phrase "a non-modified strain" can mean, for example, a control strain that has not been modified to overexpress the PAP, IMP, and/or OMP gene(s). Examples of the non-modified strain include a wild-type strain and parental strain. Specific examples of the non-modified strain include bacterial strains exemplified below including, for example, *Escherichia coli* (*E. coli*) K-12 strains such as W3110 (ATCC 27325) and MG1655 (ATCC 47076), and *Pantoea ananatis* (*P. ananatis*) AJ13355 and SC17 (FERM BP-11091). The bacterium having an L-amino acid-producing ability may be a bacterium that can accumulate an objective L-amino acid in a medium in an amount of 0.5 g/L or more, or 1.0 g/L or more.

Examples of the L-amino acid include L-alanine, L-arginine, L-asparagine, L-aspartic acid, L-citrulline, L-cysteine, L-glutamic acid, glycine, L-glutamine, L-histidine, L-isoleucine, L-leucine, L-lysine, L-methionine, L-ornithine, L-phenylalanine, L-proline, L-serine, L-threonine, L-tryptophan, L-tyrosine, and L-valine. Specific examples of the L-amino acid include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, taurine, and L-methionine; acidic amino acids such as L-glutamic acid and L-aspartic acid; and amino acids having an amide group in the side chain such as L-glutamine and L-asparagine. Particular examples of the L-amino acid include L-histidine, L-cysteine, L-valine, and L-tryptophan. More particular examples of the L-amino acid include L-histidine and L-tryptophan. The bacterium can have an ability to produce a single kind of L-amino acid, or two or more kinds of L-amino acids.

Amino acids may be L-amino acids unless otherwise stated. Furthermore, the L-amino acid to be produced may be in the form of a free compound, a salt, or a mixture of these forms. That is, the term "L-amino acid" can refer to an L-amino acid in a free form, its salt, or a mixture of these, unless otherwise stated. Examples of the salt will be described later.

Examples of bacteria belonging to the family Enterobacteriaceae include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax.cgi?id=91347) can be used.

The *Escherichia* bacterial species are not particularly limited, and examples include species classified into the genus *Escherichia* according to the taxonomy known to those skilled in the field of microbiology. Examples of the *Escherichia* bacterium include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology, Second Edition, American Society for Microbiology Press, Washington, D.C.). Examples of the *Escherichia* bacterial species include, for example, *Escherichia coli* (*E. coli*). Specific examples of *E. coli* strains include, for example, *E. coli* K-12 strains such as W3110 (ATCC 27325) and MG1655 (ATCC 47076); *E. coli* K5 strain (ATCC 23506); *E. coli* B strains such as BL21 (DE3); and derivative strains thereof.

The *Enterobacter* bacteria are not particularly limited, and examples include species classified into the genus *Enterobacter* according to classification known to a person skilled in the art of microbiology. Examples of the *Enterobacter* bacterium include, for example, *Enterobacter agglomerans* and *Enterobacter aerogenes*. Specific examples of *Enterobacter agglomerans* strains include, for example, the *Enterobacter agglomerans* ATCC 12287. Specific examples of *Enterobacter aerogenes* strains include, for example, the *Enterobacter aerogenes* ATCC 13048, NBRC 12010 (Biotechnol Bioeng., 2007, Mar. 27; 98(2):340-348), and AJ110637 (FERM BP-10955). Examples the *Enterobacter* bacterial strains also include, for example, the strains described in European Patent Application Laid-open (EP-A) No. 0952221. In addition, *Enterobacter agglomerans* also include some strains classified as *Pantoea agglomerans.*

The *Pantoea* bacteria are not particularly limited, and examples include species classified into the genus *Pantoea* according to classification known to a person skilled in the art of microbiology. Examples of the *Pantoea* bacterial species include, for example, *Pantoea ananatis* (*P. ananatis*), *Pantoea stewartii, Pantoea agglomerans*, and *Pantoea citrea*. Specific examples of *P. ananatis* strains include, for example, the *P. ananatis* LMG20103, AJ13355 (FERM BP-6614), AJ13356 (FERM BP-6615), AJ13601 (FERM BP-7207), SC17 (FERM BP-11091), and SC17(0) (VKPM B-9246). Some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Int. J. Syst. Bacteriol., 43, 162-173 (1993)). The *Pantoea* bacteria include those reclassified into the genus *Pantoea* as described above.

Examples of the *Erwinia* bacteria include *Erwinia amylovora* and *Erwinia carotovora*. Examples of the *Klebsiella* bacteria include *Klebsiella planticola.*

These strains are available from, for example, the American Type Culture Collection (Address: P.O. Box 1549, Manassas, VA 20108, United States of America). That is, registration numbers are given to the respective strains, and the strains can be ordered by using these registration numbers (refer to atcc.org/). The registration numbers of the strains are listed in the catalogue of the American Type Culture Collection. These strains can also be obtained from, for example, the depositories at which the strains were deposited.

The bacterium may be a bacterium inherently having an L-amino acid-producing ability, or may be a bacterium modified so that it has an L-amino acid-producing ability. The bacterium having an L-amino acid-producing ability can be obtained by imparting an L-amino acid-producing ability to such a bacterium as mentioned above, or by enhancing an L-amino acid-producing ability of such a bacterium as mentioned above.

To impart or enhance an L-amino acid-producing ability, methods conventionally employed in the breeding of amino acid-producing strains of *Escherichia* bacteria, and so forth (see “Amino Acid Fermentation”, Gakkai Shuppan Center (Ltd.), 1st Edition, published May 30, 1986, pp.77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a typical mutagenesis treatment, and then selecting a strain exhibiting auxotrophy, analogue resistance, or a metabolic regulation mutation, and having an L-amino acid-producing ability from the obtained mutant strains. Examples of typical mutagenesis treatments include irradiation of X-ray or ultraviolet and a treatment with a mutation agent such as N-methyl-N'-nitro-N-nitrosoguanidine (MNNG), ethyl methanesulfonate (EMS), and/or methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP 1010755 A, and so forth. The detailed procedures for enhancing enzyme activity will be described later.

Furthermore, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The “enzyme that catalyzes a reaction branching away from the biosynthetic pathway of an objective L-amino acid to generate a compound other than the objective L-amino acid” includes an enzyme involved in decomposition of the objective amino acid. An enzyme activity can be reduced by, for example, modifying a bacterium so that the gene encoding the enzyme is inactivated. The method for reducing enzyme activity will be described later.

Hereafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Arginine-Producing Bacteria>

Examples of L-arginine-producing bacteria and parental strains which can be used to derive L-arginine-producing bacteria include, but are not limited to, strains belonging to the genus *Escherichia* such as *E. coli* strain 237 (VKPM B-7925) (U.S. Patent Application No. 2002058315 A1) and its derivative strains harboring mutant N-acetylglutamate synthase (Russian Patent No. 2215783 C2), *E. coli* strain 382 (VKPM B-7926, EP1170358 A1), which is an arginine-producing strain into which argA gene encoding N-acetylglutamate synthetase is introduced (EP1170361 A1), *E. coli* strain 382 ilvA+, which is a strain obtained from the strain 382 by introducing the wild-type allele of ilvA gene native to *E. coli* K-12 strain thereto, and the like. Examples of mutant N-acetylglutamate synthase include, for example, a mutant N-acetylglutamate synthase desensitized to feedback inhibition by L-arginine by substitution for the amino acid residues corresponding to the positions 15 to 19 of the wild type enzyme (EP1170361 A1).

Examples of L-arginine-producing bacteria and parental strains which can be used to derive L-arginine-producing bacteria also include strains in which expression of one or more genes encoding an L-arginine biosynthetic enzyme are enhanced. Examples of such genes include genes encoding N-acetylglutamate synthase (argA), N-acetylglutamate kinase (argB), N-acetyl-γ-glutamylphosphate reductase (argC), N-acetylornithine aminotransferase (argD), acetylornithine deacetylase (argE), ornithine carbamoyltransferase (argF, argI), argininosuccinate synthase (argG), argininosuccinate lyase (argH), ornithine acetyltransferase (argJ), and carbamoyl phosphate synthetase (carAB). As the N-acetylglutamate synthase gene (argA), for example, a gene encoding a mutant N-acetylglutamate synthase such as those exemplified above can preferably be used.

Examples of L-arginine-producing bacteria and parental strains which can be used to derive L-arginine-producing bacteria also include strains having resistance to amino acid analogues, and so forth. Examples of such strains include *E. coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (refer to Japanese Patent Laid-open (Kokai) No. 56-106598).

<L-Citrulline-Producing Bacteria>

Examples of L-citrulline-producing bacteria and parental strains which can be used to derive L-citrulline-producing bacteria include, but are not limited to, strains belonging to the genus *Escherichia* such as *E. coli* strains 237/pMADS11, 237/pMADS12, and 237/pMADS13, which have a mutant N-acetylglutamate synthase (RU2215783 C2, European Patent No. 1170361 B1, U.S. Pat. No. 6,790,647 B2), *E. coli* strains 333 (VKPM B-8084) and 374 (VKPM B-8086), both harboring mutant feedback-resistant carbamoyl phosphate synthetase (Russian Patent No. 2264459 C2), *E. coli* strains in which α-ketoglutarate synthase activity is increased, and ferredoxin $NADP^+$ reductase, pyruvate synthase, and/or α-ketoglutarate dehydrogenase activities are additionally modified (EP2133417 A1), and strain *Pantoea ananantis* NA1 sucAsdhA, in which succinate dehydrogenase and α-ketoglutarate dehydrogenase activities are decreased (U.S. Patent Application No. 2009286290 A1), and the like.

As L-citrulline is an intermediate of L-arginine biosynthetic pathway, examples of L-citrulline-producing bacteria and parent strains which can be used to derive L-citrulline-producing bacteria, include strains in which expression of one or more genes encoding an L-arginine biosynthetic enzyme is enhanced. Examples of such genes for L-citrulline production include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), ornithine acetyltransferase (argJ), and carbamoyl phosphate synthetase (carAB), and combinations thereof.

An L-citrulline-producing bacterium can be also easily obtained from any L-arginine-producing bacterium, for example *E. coli* 382 stain (VKPM B-7926), by inactivation of argininosuccinate synthase encoded by argG gene.

<L-Cysteine-Producing Bacteria>

Examples of L-cysteine-producing bacteria and parental strains which can be used to derive L-cysteine-producing bacteria include, for example, strains in which the activity or activities of one or more of the L-cysteine biosynthetic enzymes are enhanced. Examples of such enzymes include, but are not particularly limited to, serine acetyltransferase (cysE) and 3-phosphoglycerate dehydrogenase (serA). Shown in the parentheses after the names of the enzymes are examples of genes encoding the enzymes (the same nomenclature shall similarly apply when reciting proteins/enzymes and genes hereinafter). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and US2005-0112731A. Specific examples of such a mutant serine acetyltransferase include the mutant serine acetyltransferase encoded by cysE5 gene, in which the Val residue and the Asp residue at positions 95 and 96 of a wild-type serine acetyltransferase are replaced with Arg residue and Pro residue, respectively (US2005-0112731A). Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of L-cysteine-producing bacteria and parental strains which can be used to derive L-cysteine-producing bacteria include, for example, strains in which the activity or activities of one or more of enzymes that catalyze a reaction branching away from the biosynthesis pathway of L-cysteine to generate a compound other than L-cysteine are reduced. Examples of such enzymes include, for example, enzymes involved in decomposition of L-cysteine. Examples of the enzymes involved in decomposition of L-cysteine include, but are not particularly limited to, cystathionine-β-lyase (metC) (Japanese Patent Laid-open (Kokai) No. 11-155571; Chandra et al., *Biochemistry,* 1982, 21:3064-3069), tryptophanase (tnaA) (Japanese Patent Laid-open (Kokai) No. 2003-169668; Austin N. et al., *J. Biol. Chem.,* 1965, 240:1211-1218), O-acetylserine sulfhydrylase B (cysM) (Japanese Patent Laid-open (Kokai) No. 2005-245311), the malY gene product (Japanese Patent Laid-open (Kokai) No. 2005-245311), the d0191 gene product of *Pantoea ananatis* (Japanese Patent Laid-open (Kokai) No. 2009-232844), and cysteine desulfhydrase (aecD) (Japanese Patent Laid-open (Kokai) No. 2002-233384).

Furthermore, examples of L-cysteine-producing bacteria and parental strains which can be used to derive L-cysteine-producing bacteria include, for example, strains in which the activity or activities of the L-cysteine excretory system and/or the sulfate/thiosulfate transport system are enhanced. Examples of proteins of the L-cysteine excretory system include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system include the proteins encoded by the cysP TWA gene cluster.

Specific examples of L-cysteine-producing bacteria and parental strains which can be used to derive L-cysteine-producing bacteria include, but are not limited to, strains belonging to the genus *Escherichia* such as *E. coli* JM15 transformed with different cysE alleles encoding feedback-resistant serine acetyltransferases (U.S. Pat. No. 6,218,168 B1, Russian Patent No. 2279477 C2), *E. coli* W3110 having overexpressed genes which encode proteins suitable for secreting substances toxic for cells (U.S. Pat. No. 5,972,663 A), *E. coli* strains having a lowered cysteine desulfhydrase activity (JP11155571 A2), *E. coli* W3110 having an increased activity of a positive transcriptional regulator for cysteine regulon encoded by the cysB gene (WO0127307 A1), and the like.

<L-Glutamic Acid-Producing Bacteria>

Examples of L-glutamic acid-producing bacteria and parental strains which can be used to derive L-glutamic acid-producing bacteria include, but are not limited to, strains belonging to the genus *Escherichia* such as *E. coli* VL334thrC$^+$ (EP 1172433 A1). The *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K-12 (VKPM B-7) cells. As a result, an L-isoleucine auxotrophic strain VL334thrC$^+$ (VKPM B-8961), which is able to produce L-glutamic acid, was obtained.

Examples of L-glutamic acid-producing bacteria and parental strains which can be used to derive the L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltBD), isocitrate dehydrogenase (icdA), aconitate hydratase (acnA, acnB), citrate synthase (OA), methylcitrate synthase (prpC), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi), 6-phosphogluconate dehydratase (edd), 2-keto-3-deoxy-6-phosphogluconate aldolase (eda), and transhydrogenase. It is preferable to enhance the activity or activities of one or more kinds of enzymes selected from, for example, glutamate dehydrogenase, citrate synthase, phosphoenol pyruvate carboxylase, and methylcitrate synthase, among these enzymes.

Examples of strains belonging to the family Enterobacteriaceae and modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2. Furthermore, examples of strains belonging to the family Enterobacteriaceae and modified so that the expression of a gene of the Entner-Doudoroff pathway (edd, eda) is increased include those disclosed in EP1352966B.

Examples of L-glutamic acid-producing bacteria and parental strains which can be used to derive the L-glutamic acid-producing bacteria also include strains having a decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), succinate dehydrogenase (sdhABCD), and 1-pyroline-5-carboxylate dehydrogenase (putA). It is preferable to reduce or delete, for example, the α-ketoglutarate dehydrogenase activity, among these enzymes.

Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$,

*E. coli* AJ12624 (FERM BP-3853),

*E. coli* AJ12628 (FERM BP-3854),

*E. coli* AJ12949 (FERM BP-4881).

*E. coli* W3110sucA:Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Examples of L-glutamic acid-producing bacteria and parental strains which can be used to derive the L-glutamic acid-producing bacteria also include *Pantoea* bacteria, such as the *P. ananatis* AJ13355 strain (FERM BP-6614), *P. ananatis* SC17 strain (FERM BP-11091), and *P. ananatis* SC17(0) strain (VKPM B-9246). The AJ13355 strain is a strain isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depositary (currently, independent administrative agency, National Institute of Technology and Evaluation, International Patent Organism Depositary (NITE IPOD), #120, 2-5-8 Kazusakamatari, Kisarazu-shi, Chiba, 292-0818, Japan) on Feb. 4, 2009, and assigned an accession number of FERM BP-11091. The AJ13355 strain was deposited at the National Institute of Bioscience and Human Technology, Agency of Industrial Science and Technology, Ministry of International Trade and Industry (currently, NITE IPOD), #120, 2-5-8 Kazusakamatari, Kisarazu-shi, Chiba, 292-0818, Japan) on Feb. 19, 1998 and assigned an accession number of FERM P-16644. Then, the deposit was converted to an international deposit under the provisions of the Budapest Treaty on Jan. 11, 1999, and assigned an accession number of FERM BP-6614.

Examples of L-glutamic acid-producing bacteria and parental strains which can be used to derive the L-glutamic acid-producing bacteria also include mutant strains belonging to the genus *Pantoea* that are deficient in the α-ketoglutarate dehydrogenase activity or have a decreased α-ketoglutarate dehydrogenase activity, and can be obtained as described above. Such strains include *P. ananatis* AJ13356 (U.S. Pat. No. 6,331,419 B1), which is an α-ketoglutarate dehydrogenase E1 subunit (sucA) gene-deficient strain of the AJ13355 strain, and *Pantoea ananatis* SC17sucA (U.S. Pat. No. 6,596,517), which is a sucA gene-deficient strain of the SC17 strain. *P. ananatis* AJ13356 was deposited at the National Institute of Bioscience and Human-Technology, Agency of Industrial Science and Technology, Ministry of International Trade and Industry (currently, NITE IPOD, #120, 2-5-8 Kazusakamatari, Kisarazu-shi, Chiba, 292-0818, Japan) on Feb. 19, 1998 under the accession number FERM P-16645. It was then converted to an international deposit under the provisions of the Budapest Treaty on Jan. 11, 1999 and received an accession number of FERM BP-6615. The above strain was identified as *Enterobacter agglomerans* when it was isolated and deposited as the *Enterobacter agglomerans* AJ13356. However, it was recently re-classified as *P. ananatis* on the basis of nucleotide sequencing of 16S rRNA and so forth. Although AJ13356 was deposited at the aforementioned depository as *Enterobacter agglomerans*, for the purposes of this specification, they are described as *P. ananatis*.

Examples of L-glutamic acid-producing bacteria and parental strains which can be used to derive the L-glutamic acid-producing bacteria also include strains belonging to the genus *Pantoea* such as the *P. ananatis* SC17sucA/RSFCPG+pSTVCB strain, *P. ananatis* AJ13601 strain, *P. ananatis* NP106 strain, and *P. ananatis* NA1 strain. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) native to *E. coli*, and the plasmid pSTVCB containing the citrate synthase gene (gltA) native to *Brevibacterium lactofermentum*, into the SC17sucA strain. The AJ13601 strain is a strain selected from the SC17sucA/RSFCPG+pSTVCB strain as a strain resistant to a high concentration of L-glutamic acid at a low pH. The NP106 strain was obtained from the AJ13601 strain by curing the RSFCPG and pSTVCB plasmids. The AJ13601 strain was deposited at the National Institute of Bioscience and Human Technology, Agency of Industrial Science and Technology, Ministry of International Trade and Industry (currently, NITE IPOD, #120, 2-5-8 Kazusakamatari, Kisarazu-shi, Chiba, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parental strains which can be used to derive the L-glutamic acid-producing bacteria also include auxotrophic mutant strains. Specific examples of auxotrophic mutant strains include, for example, *E. coli* VL334thrC$^+$ (VKPM B-8961, EP1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC$^+$ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parental strains which can be used to derive the L-glutamic acid-producing bacteria also include strains having resistance to an aspartic acid analogue. Such strains can also be deficient in the α-ketoglutarate dehydrogenase activity. Specific examples of strains having resistance to an aspartic acid analogue and deficient in the α-ketoglutarate dehydrogenase activity include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* AJ13138 (FERM BP-5565, U.S. Pat. No. 6,110,714).

<L-Histidine-Producing Bacteria>

Examples of L-histidine-producing bacteria and parental strains which can be used to derive L-histidine-producing bacteria include strains in which expression of one or more genes encoding an L-histidine biosynthetic enzyme are enhanced. Examples of such genes include genes encoding ATP phosphoribosyltransferase (hisG), phosphoribosyl-ATP pyrophosphatase (hisE), phosphoribosyl-AMP cyclohydrolase (hisI), phosphoribosyl-AMP cyclohydrolase/phosphoribosyl-ATP pyrophosphatase (hisIE), phosphoribosyl-formimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine. Therefore an L-histidine-producing ability can also be efficiently enhanced by, for example, introducing a mutation conferring resistance to the feedback inhibition into ATP phosphoribosyltransferase (Russian Patent Nos. 2003677 C1 and 2119536 C1).

Specific examples of L-histidine-producing bacteria and parental strains which can be used to derive L-histidine-producing bacteria also include, for example, strains belonging to the genus *Escherichia* such as *Escherichia coli* strain 24 (VKPM B-5945, RU2003677 C1), *Escherichia coli* NRRL B-12116 to B-12121 (U.S. Pat. No. 4,388,405), *Escherichia coli* H-9342 (FERM BP-6675) and H-9343 (FERM BP-6676) (U.S. Pat. No. 6,344,347 B1), *Escherichia coli* H-9341 (FERM BP-6674) (EP1085087 A2), *Escherichia coli* AI80/pFM201 (U.S. Pat. No. 6,258,554 B1), *E. coli* FERM-P 5038 and 5048, which have been transformed with a vector carrying a DNA encoding an L-histidine-biosynthetic enzyme (JP 56-005099 A), *E. coli* strains transformed with rht, a gene for an amino acid-export (EP1016710 A2), *E. coli* 80 strain, which has been imparted with sulfaguanidine, DL-1,2,4-triazole-3-alanine, and streptomycin-resistance (VKPM B-7270, RU2119536 C1), *E. coli* MG1655+hisGr hisL'_Δ ΔpurR (RU2119536 and Doroshenko V. G. et al. (2013) *Prikl. Biochim. Mikrobiol.* (Russian), 49(2): 149-154), and so forth.

<L-Isoleucine-Producing Bacteria>

Examples of L-isoleucine-producing bacteria and parental strains which can be used to derive the L-isoleucine-producing bacteria include, but are not limited to, strains in which the activity or activities of one or more of the L-isoleucine biosynthetic enzymes are enhanced. Examples of such enzymes include, but not particularly limited to, threonine deaminase and acetohydroxy acid synthase (Japanese Patent Laid-open (Kokai) No. 2-458, EP0356739A, U.S. Pat. No. 5,998,178).

Examples of L-isoleucine-producing bacteria and parental strains which can be used to derive L-isoleucine-producing bacteria include, but are not limited to, *Escherichia* bacteria such as mutant strains having resistance to 6-dimethylaminopurine (JP 5-304969 A), mutant strains having resistance to an isoleucine analogue such as thiaisoleucine and isoleucine hydroxamate, and mutant strains additionally having resistance to DL-ethionine and/or arginine hydroxamate (JP 5-130882 A).

Examples of L-isoleucine-producing bacteria and parental strains which can be used to derive the L-isoleucine-producing bacteria include, but are not limited to, strains in which the activity or activities of one or more of the L-isoleucine biosynthetic enzymes are enhanced. Examples of such enzymes include, but not particularly limited to, threonine deaminase and acetohydroxate synthase (JP 2-458 A, EP0356739 A1, and U.S. Pat. No. 5,998,178).

<L-Leucine-Producing Bacteria>

Examples of L-leucine-producing bacteria and parental strains which can be used to derive L-leucine-producing bacteria include, but are not limited to, strains belonging to the genus *Escherichia* such as *E. coli* strains resistant to leucine (for example, the strain 57 (VKPM B-7386, U.S. Pat. No. 6,124,121)); *E. coli* strains resistant to leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

Examples of L-leucine-producing bacteria and parental strains which can be used to derive L-leucine-producing bacteria also include strains in which the expression of one or more genes involved in L-leucine biosynthesis is enhanced. Examples of such genes include genes of the leuABCD operon. As the leuA gene, for example, a mutant leuA gene encoding α-isopropylmalate synthase desensitized to feedback inhibition by L-leucine (U.S. Pat. No. 6,403,342 B1) can be preferably used.

In addition, examples of L-leucine-producing bacteria and parental strains which can be used to derive L-leucine-producing bacteria also include strains in which the expression of one or more genes encoding proteins which excrete L-amino acid from the bacterial cell is enhanced. Examples of such genes include the b2682 and b2683 genes (ygaZH genes) (EP1239041 A2).

<L-Lysine-Producing Bacteria>

Examples of L-lysine-producing bacteria and parental strains which can be used to derive L-lysine-producing bacteria include mutant strains belonging to the genus *Escherichia* and having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting bacteria belonging to the genus *Escherichia* to a conventional artificial mutagenesis treatment. Specific examples of bacterial strains useful for producing L-lysine include *E. coli* AJ11442 (FERM BP-1543, NRRL B-12185; see U.S. Pat. No. 4,346,170) and *E. coli* VL611. In these strains, feedback inhibition of aspartokinase by L-lysine is desensitized.

Examples of L-lysine-producing bacteria and parental strains which can be used to derive L-lysine-producing bacteria also include strains in which expression of one or more genes encoding an L-lysine biosynthetic enzyme is enhanced. Examples of such genes include, but are not limited to, genes encoding dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195 A1). It is preferable to enhance the activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase, among these enzymes. In addition, L-lysine-producing bacteria and parental strains which can be used to derive L-lysine-producing bacteria may have an increased level of expression of the gene involved in energy efficiency (cyo) (EP1170376 A1), the gene encoding nicotinamide nucleotide transhydrogenase (pntAB) (U.S. Pat. No. 5,830,716 A), the ybjE gene (WO2005/073390), or combinations thereof. Since aspartokinase III (lysC) is subjected to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Examples of the aspartokinase III desensitized to feedback inhibition by L-lysine include aspartokinase III derived from *Escherichia coli* and having one or more mutations such as replacing the methionine residue at position 318 with an isoleucine residue; replacing the glycine residue at position 323 with an aspartic acid residue; and replacing the threonine residue at position 352 with an isoleucine residue (U.S. Pat. Nos. 5,661,012 and 6,040,160). Furthermore, since dihydrodipicolinate synthase (dapA) is subjected to feedback inhibition by L-lysine, a mutant dapA gene encoding a dihydrodipicolinate synthase desensitized to feedback inhibition by L-lysine may be used for enhancing the activity of this enzyme. Examples of the dihydrodipicolinate synthase desensitized to feedback inhibition by L-lysine include dihydrodipicolinate synthase derived from *Escherichia coli* and having a mutation for replacing the histidine residue at position 118 with a tyrosine residue (U.S. Pat. No. 6,040,160).

L-Lysine-producing bacteria or parental strains which can be used to derive L-lysine-producing bacteria may have a reduced or no activity of an enzyme that catalyzes a reaction which causes a branching off from the L-amino acid biosynthesis pathway and results in the production of another compound. Also, L-lysine-producing bacteria or parental strains which can be used to derive L-lysine-producing bacteria may have a reduced or no activity of an enzyme that negatively acts on L-lysine synthesis or accumulation. Examples of such enzymes include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth. The lysine decarboxylase activity can be decreased or deleted by, for example, decreasing expression of both the cadA and ldcC genes encoding lysine decarboxylase. Expression of the both genes can be decreased by, for example, the method described in WO2006/078039.

Examples of L-lysine-producing bacteria and parental strains which can be used to derive L-lysine-producing bacteria also include the *E. coli* WC196 strain (FERM BP-5252, U.S. Pat. No. 5,827,698), the *E. coli* WC196ΔcadAΔldcC strain (FERM BP-11027), also named as WC196LC, and the *E. coli* WC196ΔcadAΔldcC/pCABD2 strain (WO2006/078039).

The WC196 strain was bred from the W3110 strain, which was derived from *E. coli* K-12, by conferring AEC resistance to the W3110 strain (U.S. Pat. No. 5,827,698). The WC196 strain was designated *E. coli* AJ13069, deposited at the National Institute of Bioscience and Human-Technology, Agency of Industrial Science and Technology (currently, NITE IPOD, #120, 2-5-8 Kazusakamatari, Kisarazu-shi, Chiba, 292-0818, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

The WC196ΔcadAΔldcC strain was constructed from the WC196 strain by disrupting the cadA and ldcC genes which encode lysine decarboxylase. The WC196ΔcadAΔldcC was designated AJ110692 and deposited at the National Institute of Bioscience and Human-Technology, Agency of Industrial Science and Technology, Ministry of International Trade and Industry (currently, NITE IPOD, #120, 2-5-8 Kazusakamatari, Kisarazu-shi, Chiba, 292-0818, Japan) on Oct. 7, 2008 as an international deposit under the accession number FERM BP-11027.

The WC196ΔcadAΔldcC/pCABD2 strain was constructed by introducing the plasmid pCABD2 containing lysine biosynthesis genes (U.S. Pat. No. 6,040,160) into the WC196ΔcadAΔldcC strain. The plasmid pCABD2 contains a mutant dapA gene derived from *E. coli* and encoding a dihydrodipicolinate synthase (DDPS) having a mutation for desensitization to feedback inhibition by L-lysine (H118Y), a mutant lysC gene derived from *E. coli* and encoding aspartokinase III having a mutation for desensitization to feedback inhibition by L-lysine (T3521), the dapB gene native to *E. coli* and encoding dihydrodipicolinate reductase, and the ddh gene native to *Brevibacterium lactofermentum* and encoding diaminopimelate dehydrogenase.

Examples of L-lysine-producing bacteria and parental strains which can be used to derive L-lysine-producing bacteria also include *E. coli* AJIK01 (NITE BP-01520). The AJIK01 strain was designated *E. coli* AJ111046, and deposited at the independent administrative agency, National Institute of Technology and Evaluation, Patent Microorganisms Depositary (NITE NPMD, #122, 2-5-8 Kazusakamatari, Kisarazu-shi, Chiba, 292-0818, Japan) on Jan. 29, 2013. Then, it was converted to an international deposit under the provisions of the Budapest Treaty on May 15, 2014, and assigned an accession number of NITE BP-01520.

<L-Methionine-Producing Bacteria>

Examples of L-methionine-producing bacteria and parent strains which can be used to derive L-methionine-producing bacteria include, but are not limited to, strains belonging to the genus *Escherichia* such as *E. coli* strains AJ11539 (NRRL B-12399), AJ11540 (NRRL B-12400), AJ11541 (NRRL B-12401), AJ11542 (NRRL B-12402) (Patent GB2075055); and *E. coli* strains 218 (VKPM B-8125) (RU2209248 C2) and 73 (VKPM B-8126) (RU2215782 C2) resistant to norleucine, the L-methionine analog, or the like. The strain *E. coli* 73 was deposited in the Russian National Collection of Industrial Microorganisms (VKPM; 1st Dorozhny proezd, 1, Moscow 117545, Russian Federation) on May 14, 2001 under the accession number VKPM B-8126. Then, it was converted to an international deposit under the provisions of the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as L-methionine-producing bacteria or parent strains. Another example of L-methionine-producing bacteria of the genus *Escherichia* and parent strains thereof that can be used to derive L-methionine-producing bacteria can be an *E. coli* strain that is deficient in a repressor of L-methionine biosynthesis system (MetJ) and has increased activity of intracellular homoserine transsuccinylase (MetA) (U.S. Pat. No. 7,611,873 B1), an *E. coli* strain in which activity of cobalamin-independent methionine synthase (MetE) is suppressed and activity of cobalamin-dependent methionine synthase (MetH) is increased (EP2861726 B1), an *E. coli* strain that has an ability to produce L-threonine and is transformed with vector(s) expressing threonine dehydratase (tdcB, ilvA) and, at least, O-succinylhomoserine lyase (metB), cystathionine β-lyase (metC), 5,10-methylenetetrahydrofolate reductase (metF) and serine hydroxymethyltransferase (glyA) (U.S. Pat. No. 7,790,424 B2), *E. coli* strain in which activity of transhydrogenase (pntAB) is enhanced (EP2633037 B1), and so forth.

<L-Ornithine-Producing Bacteria>

As L-ornithine is an intermediate of L-arginine biosynthetic pathway, examples of L-ornithine-producing bacteria and parent strains which can be used to derive L-ornithine-producing bacteria, include strains in which expression of one or more genes encoding an L-arginine biosynthetic enzyme is enhanced. Examples of such genes for L-ornithine production include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine acetyltransferase (argJ), and combinations thereof.

An L-ornithine-producing bacterium can be easily obtained from any L-arginine-producing bacterium, for example *E. coli* 382 stain (VKPM B-7926), by inactivation of ornithine carbamoyltransferase encoded by both argF and argI genes. Methods for inactivation of ornithine carbamoyltransferase are described herein.

<L-Phenylalanine-Producing Bacteria>

Examples of L-phenylalanine-producing bacteria and parental strains which can be used to derive L-phenylalanine-producing bacteria include, but are not limited to, strains belonging to the genus *Escherichia* such as *E. coli* AJ12739 (tyrA:Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952), *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named as AJ12604 (FERM BP-3579) (EP488424 B1). Furthermore, L-phenylalanine-producing bacteria and parental strains which can be used to derive L-phenylalanine-producing bacteria also include strains belonging to the genus *Escherichia* and having an enhanced activity of the protein encoded by the yedA gene or the yddG gene (U.S. Pat. Nos. 7,259,003 and 7,666,655).

<L-Proline-Producing Bacteria>

Examples of L-proline-producing bacteria and parental strains which can be used to derive L-proline-producing bacteria include, but are not limited to, strains belonging to the genus *Escherichia* such as *E. coli* 702ilvA (VKPM B-8012), which is deficient in the ilvA gene and is able to produce L-proline (EP1172433 A1). Examples of L-proline-producing bacteria and parental strains which can be used to derive L-proline-producing bacteria also include strains in which the expression of one or more genes involved in L-proline biosynthesis is enhanced. Examples of such genes which can be used in L-proline-producing bacteria include the proB gene encoding glutamate kinase with desensitized feedback inhibition by L-proline (DE3127361 A1). In addition, examples of L-proline-producing bacteria and parental strains which can be used to derive L-proline-producing bacteria also include strains in which the expression of one or more genes encoding proteins responsible for excreting L-amino acid from the bacterial cell is enhanced. Examples of such genes include the b2682 and b2683 genes (ygaZH genes) (EP1239041 A2).

Examples of bacteria belonging to the genus *Escherichia* that have an ability to produce L-proline include the following *E. coli* strains: NRRL B-12403 and NRRL B-12404 (GB Patent 2075056), VKPM B-8012 (Russian Patent No. 2207371 C2), plasmid mutants described in DE3127361 A1, plasmid mutants described by Bloom F. R. et al. in "The 15$^{th}$ Miami winter symposium", 1983, p.34, and the like.

<L-Threonine-Producing Bacteria>

Examples of L-threonine-producing bacteria and parental strains which can be used to derive L-threonine-producing bacteria also include strains in which the activity or activities of one or more kinds of the L-threonine biosynthetic enzymes are enhanced. Examples of such enzymes include, but are not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, it is preferable to enhance activity or activities of one or more kinds of enzymes such as aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine. Examples of such a strain in which threonine decomposition is suppressed include, for example, the *E. coli* TDH6 strain, which is deficient in the threonine dehydrogenase activity (Japanese Patent Laid-open (Kokai) No. 2001-346578).

The activities of the L-threonine biosynthesis enzymes are inhibited by the endproduct, L-threonine. Therefore, for constructing L-threonine-producing strains, it is preferred that the genes of the L-threonine biosynthesis enzymes are modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture broth and also suppressed by attenuation. Therefore, expression of the threonine operon can be enhanced by removing the leader sequence or the attenuator in the attenuation region (Lynn S. P. et al., *J. Mol. Biol.,* 1987, 194:59-69; WO02/26993, WO2005/049808, and WO2003/097839).

The native promoter of the threonine operon is present upstream of the threonine operon, and can be replaced with a non-native promoter (WO98/04715). Also, the threonine operon may be constructed so that the threonine biosynthesis genes are expressed under control of the repressor and promoter of λ-phage (EP0593792B). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

It is preferred that the expression amount of the threonine operon that is modified so as to be desensitized to feedback inhibition by L-threonine as described above is increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance include the rhtA gene (Livshits V. A. et al., *Res. Microbiol.,* 2003, 154:123-135), rhtB gene (EP0994190A), rhtC gene (EP1013765A), yfiK gene, and yeaS gene (EP1016710A). Examples of methods for imparting L-threonine resistance to a host include those described in EP0994190A and WO90/04636.

Examples of L-threonine-producing bacteria and parental strains which can be used to derive L-threonine-producing bacteria include, but are not limited to, strains belonging to the genus *Escherichia* such as *E. coli* TDH-6/pVIC40 (VKPM B-3996) (U.S. Pat. Nos. 5,175,107 and 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al. (1978) Genetika (Russian), 14: 947-956), *E. coli* VL643 and VL2055 (EP1149911 A2), *E. coli* VKPM B-5318 (EP0593792 A1), and the like.

The strain TDH-6 is deficient in the thrC gene, as well as being sucrose-assimilative, and the ilvA gene thereof has a leaky mutation. This strain also has a mutation in the rhtA gene, which mutation imparts resistance to high concentrations of threonine or homoserine. The strain VKPM B-3996, which contains the plasmid pVIC40, was obtained by introducing the plasmid pVIC40 into the TDH-6 strain. The plasmid pVIC40 was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain VKPM B-3996 was deposited on Nov. 19, 1987 in the All-Union Scientific Center of Antibiotics (Russian Federation, 117105 Moscow, Nagatinskaya Street 3-A) under the accession number RIA 1867. The strain VKPM B-3996 was also deposited in the Russian National Collection of Industrial Microorganisms (VKPM; 1$^{st}$ Dorozhny proezd, 1, Moscow 117545, Russian Federation) on Apr. 7, 1987 under the accession number VKPM B-3996.

The strain B-5318 is prototrophic with regard to isoleucine; and a temperature-sensitive lambda-phage C1 repressor and PR promoter replace the regulatory region of the threonine operon in plasmid pVIC40. The strain VKPM B-5318 was deposited in the Russian National Collection of Industrial Microorganisms (VKPM) on May 3, 1990 under the accession number VKPM B-5318.

L-Threonine-producing bacteria or parental strains which can be used to derive L-threonine-producing bacteria can be additionally modified to enhance expression of one or more of the following genes:

the mutant thrA gene which encodes aspartokinase homoserine dehydrogenase I resistant to feedback inhibition by threonine, the thrB gene which encodes homoserine kinase, the thrC gene which encodes threonine synthase, the rhtA gene which encodes a putative transmembrane protein of the threonine and homoserine efflux system, the asd gene which encodes aspartate-β-semialdehyde dehydrogenase, and the aspC gene which encodes aspartate aminotransferase (aspartate transaminase).

The thrA gene which encodes aspartokinase I and homoserine dehydrogenase I of *E. coli* has been elucidated (KEGG, Kyoto Encyclopedia of Genes and Genomes, entry No. b0002; GenBank, accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG, entry No. b0003; GenBank, accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG, entry No. b0004; GenBank, accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects the transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG, entry No. b0813; GenBank, accession No. NC_000913.2; nucleotide positions: 848,433 to 849,320, complement; Gene ID: 947045). The rhtA gene is located between the dps and ompXgenes on the chromosome of *E. coli* K-12 close to the glnHPQ operon, which encodes components of the glutamine transport system. The rhtA gene is identical to the ybiF gene (KEGG, entry No. b0813).

The asd gene which encodes aspartate-β-semialdehyde dehydrogenase of *E. coli* has been elucidated (KEGG, entry No. b3433; GenBank, accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG, entry No. b0928; GenBank, accession No. NC 000913.2; nucleotide positions: 983,742 to 984,932, complement; Gene ID: 945553). The aspC gene is located between the ycbL gene on the opposite strand and the ompF gene on the same strand on the chromosome of *E. coli* K-12.

<L-Tryptophan-Producing Bacteria>

Examples of L-tryptophan-producing bacteria and parental strains which can be used to derive the L-tryptophan-producing bacteria include, but are not limited to, strains belonging to the genus *Escherichia* such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373 B1), *E. coli* AGX17 (pGX44) (NRRL B-12263) and AGX6 (pGX50)aroP (NRRL B-12264) deficient in the enzyme tryptophanase (U.S. Pat. No. 4,371,614), *E. coli* AGX17/pGX50,pACKG4-pps having an enhanced phosphoenolpyruvate-producing ability (WO97/08333, U.S. Pat. No. 6,319,696 B1), and the like. Examples of L-tryptophan-producing bacteria and parental strains which can be used to derive the L-tryptophan-producing bacteria also include strains belonging to the genus *Escherichia* and having an enhanced activity of the protein encoded by the yedA gene or the yddG gene (U.S. Patent Application Nos. 2003148473 A1 and 2003157667 A1).

Examples of L-tryptophan-producing bacteria and parental strains which can be used to derive the L-tryptophan-producing bacteria also include strains in which one or more activities of anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, and hence, a mutation desensitizing the feedback inhibition may be introduced into these enzymes. Specific examples of strains having such a mutation include *E. coli* SV164, which harbors desensitized anthranilate synthase, and a transformant strain obtained by introducing into the *E. coli* SV164 the plasmid pGH5 (WO94/08031 A1), which contains a mutant serA gene encoding feedback-desensitized phosphoglycerate dehydrogenase.

Examples of L-tryptophan-producing bacteria and parental strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of a and subunits which are encoded by the trpA and trpB genes, respectively. In addition, L-tryptophan-producing ability may be improved by enhancing expression of the isocitrate lyase-malate synthase operon (WO2005/103275).

<L-Valine-Producing Bacteria>

Examples of L-valine-producing bacteria and parental strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of L-valine-producing bacteria and parental strains for deriving L-valine-producing bacteria also include mutant strains having a mutation in aminoacyl-tRNA synthetase (U.S. Pat. No. 5,658,766). Examples of such strains include *E. coli* VL1970, which has a mutation in the ileS gene encoding isoleucine tRNA synthetase. *E. coli* VL1970 was deposited in the Russian National Collection of Industrial Microorganisms (VKPM; 1st Dorozhny proezd, 1, Moscow 117545, Russian Federation) on Jun. 24, 1988 under the accession number VKPM B-4411.

Furthermore, mutant strains requiring lipoic acid for growth and/or lacking $H^+$-ATPase can also be used as L-valine-producing bacteria or parental strains (WO96/06926 A1).

Examples of L-valine-producing bacteria and parent strains for deriving L-valine-producing bacteria also include *E. coli* H81 strain (VKPM B-8066; see, for example, EP1942183 B1), *E. coli* NRRL B-12287 and NRRL B-12288 (U.S. Pat. No. 4,391,907), *E. coli* VKPM B-4411 (U.S. Pat. No. 5,658,766), *E. coli* VKPM B-7707 (EP1016710 A2), or the like.

The genes and proteins used for breeding L-amino acid-producing bacteria may have, for example, known nucleotide sequences and amino acid sequences of the genes and proteins exemplified above, respectively. Also, the genes and proteins used for breeding L-amino acid-producing bacteria may be variants of the genes and proteins exemplified above, such as variants of genes and proteins having known nucleotide sequences and amino acid sequences, respectively, so long as the original function thereof, such as respective enzymatic activities in cases of proteins, is maintained. As for variants of genes and proteins, the descriptions concerning variants of the PAP, IMP, and OMP proteins and genes encoding them described herein can be similarly applied.

The phrase "a bacterium has been modified to overexpress a gene encoding a periplasmic adaptor protein" can mean that the bacterium has been modified in such a way that in the modified bacterium the total amount and/or the total activity of the corresponding gene protein product such as a PAP is increased as compared with (i.e. higher than), or the expression level (i.e. expression amount) of a gene encoding a PAP is increased as compared with (i.e. higher than), that is observed for a non-modified strain, for example, a wild-type or parental strain. Examples of a non-modified strain that can serve as a reference for the above comparison can include a wild-type strain of a bacterium belonging to the family Enterobacteriaceae such as, for example, the *E. coli* W3110 strain (ATCC 27325), the *E. coli* MG1655 strain (ATCC 47076), the *P. ananatis* AJ13355 strain (FERM BP-6614), the *P. ananatis* SC17 strain (FERM BP-11091), and so forth.

That is, the phrase "a gene encoding a periplasmic adaptor protein is overexpressed" can mean that the total amount and/or the total activity of the corresponding gene protein product such as a PAP is increased as compared with (i.e. higher than) that is observed for a non-modified strain. The total amount and/or the total activity of the corresponding gene protein product such as a PAP can be increased by, for example, increasing (i.e. enhancing) the expression level of said gene, or increasing the activity per molecule (may be referred to as a specific activity) of the protein encoded by said gene, as compared with a non-modified strain, for example, a wild-type or parental strain. An increase in the total amount or the total activity of a protein can be measured as, for example, an increase in the amount or activity of the protein per cell, which may be an average amount or activity of the protein per cell. The bacterium can be modified so that the amount and/or the activity of the PAP per cell is increased to 150% or more, 200% or more, 300% or more, of the amount and/or the activity in a non-modified strain.

The phrase "a gene encoding a periplasmic adaptor protein is overexpressed" can also mean that the expression level (i.e. expression amount) of a gene encoding a PAP is increased as compared with (i.e. higher than) that is observed for a non-modified strain. Therefore, the phrase "a gene encoding a periplasmic adaptor protein is overexpressed" can be used interchangeably or equivalently to the phrase "expression of a gene encoding a periplasmic adaptor protein is enhanced or increased" or the phrase "the expression level of a gene encoding a periplasmic adaptor protein is enhanced or increased". An increase in the expression level of a gene can be measured as, for example, an increase in the expression level of the gene per cell, which may be an average expression level of the gene per cell. The phrase "the expression level of a gene" or "the expression amount of a gene" can mean, for example, the amount of an expression product of a gene, such as the amount of mRNA of the gene or the amount of the protein encoded by the gene. The bacterium may be modified so that the expression level of a gene encoding a periplasmic adaptor protein per cell is increased to, for example, 150% or more, 200% or more, or 300% or more, of the expression level of in a non-modified strain.

Examples of methods which can be used to enhance expression of a gene such as a gene encoding a periplasmic adaptor include, but are not limited to, methods of increasing the copy number of the gene, such as the copy number of the gene in the bacterial genome (i.e. in the chromosome) and/or in the autonomously replicating vector, such as a plasmid, harbored by the bacterium. The copy number of a gene can be increased by, for example, introducing the gene into the chromosome of the bacterium and/or introducing an autonomously replicating vector containing the gene into the bacterium. Such increasing of the copy number of a gene can be carried out according to genetic engineering methods known to the person of ordinary skill in the art.

Examples of the vectors that can be used for a bacterium belonging to the family Enterobacteriaceae can include, but are not limited to, conditionally-replicated vectors such as, for example, vectors having R6K (oriRγ) origin replication such as, for example, the pAH162 vector and the like, narrow-host-range plasmids such as pMW118/119, pBR322, pUC19 and the like, or broad-host-range plasmids such as RSF1010, RP4 and the like. The gene encoding a PAP can also be introduced into the chromosomal DNA of a bacterium by, for example, homologous recombination, Mu-driven integration, or the like. One copy, or two or more copies of the gene encoding a PAP may be introduced. For example, homologous recombination can be carried out using a nucleotide sequence the multiple copies of which are present in the chromosomal DNA as a target to introduce multiple copies of the gene encoding a PAP into the chromosomal DNA. Examples of a nucleotide sequences multiple copies of which are present in the chromosomal DNA can include, but are not limited to, repetitive DNA, and inverted repeats present at the end of a transposable element. In addition, it is possible to incorporate a gene into a transposon and allow it to be transferred to introduce multiple copies of the gene into the chromosomal DNA. A method for intrachromosomal amplification can be used to introduce multiple copies of a gene into the chromosomal DNA. By using Mu-driven transposition, more than 3 copies of the gene can be introduced into the chromosomal DNA of recipient strain in one step (Akhverdyan et al. (2007) Biotechnol. (Russian), 3:3-20).

A gene to be introduced into the bacterium as described herein can be ligated downstream from a promoter. The promoter is not particularly limited so long as the promoter that can function in the host bacterium is chosen, and it may be a promoter native to the host bacterium, or it may be a heterologous promoter. The phrase "a promoter that can function in a host bacterium" can refer to a promoter that possesses promoter activity in a host bacterium. Specific examples of a promoter that can function in a bacterium belonging to the family Enterobacteriaceae include, but are not limited to, potent promoters exemplified below.

Examples of methods which can be used to enhance expression of a gene such as a gene encoding a PAP also include methods of increasing the expression level of the gene by modification of an expression regulatory region of that gene. Modification of an expression regulatory region of a gene can be employed in combination with an increase in the copy number of the gene. An expression regulatory region of a gene can be modified by, for example, replacing the native expression regulatory region of the gene with native and/or modified foreign regulatory region(s). The phrase "an expression regulatory region" can be used interchangeably or equivalently to the phrase "an expression regulatory sequence". As the gene encoding a PAP may be organized in operon structure, the method which can be used to enhance expression of the gene also includes increasing the expression level of the operon having that gene by modification of an expression regulatory region of the operon, wherein the modification can be carried out by, for example, replacing the native expression regulatory region of the operon with native and/or modified foreign regulatory region(s). In this method, the expression of two or more genes, including the gene encoding the PAP, can be enhanced at the same time.

Expression regulatory regions can be exemplified by promoters, enhancers, operators, attenuators and termination signals, anti-termination signals, ribosome-binding sites (RBS) and other expression control elements (e.g., regions to which repressors or activators bind and/or binding sites for transcriptional and translational regulatory proteins, for example, in the transcribed mRNA). Such regulatory regions are described, for example, in known documents (e.g., Sambrook J., Fritsch E. F. and Maniatis T., "Molecular Cloning: A Laboratory Manual", $2^{nd}$ ed., Cold Spring Harbor Laboratory Press (1989); Pfleger et al., (2006) Nat. Biotechnol., 24: 1027-1032; Mutalik et al. (2013) Nat. Methods, 10: 354-360). Modifications of an expression regulatory region of a gene can be combined with increasing the copy number of the gene (see, for example, Akhverdyan et al. (2011) Appl. Microbiol. Biotechnol., 91: 857-871; Tyo et al. (2009) Nature Biotechnol., 27: 760-765).

The exemplary promoters suitable for enhancing expression of a gene encoding a PAP can be the potent promoters. The phrase "a potent promoter" can refer to a promoter that is stronger than the native promoter of a gene encoding a PAP. Examples of potent promoters that can function in a bacterium belonging to the family Enterobacteriaceae can include, but are not limited to, the lac promoter, the trp promoter, the trc promoter, the tac promoter, the tet promoter, the araBAD promoter, the rpoH promoter, the msrA promoter, the Pm 1 promoter (derived from the genus *Bifidobacterium*), Pnlp8 promoter (WO2012/137689), and the PR or the $P_L$ promoters of lambda (λ) phage. As a potent promoter, a highly active variant of an existing promoter may also be obtained by using various reporter genes. For example, by making the −35 and −10 regions in a promoter region closer to a consensus sequence, the strength of the promoter can be enhanced (WO0018935 A1). The strength of a promoter can be defined by the frequency of initiation acts of RNA synthesis. Examples of the method for evaluating the strength of a promoter and examples of strong promoters are described in the paper of Goldstein M. A. et al. (Prokaryotic promoters in biotechnology, *Biotechnol. Annu. Rev.,* 1995, 1:105-128) and so forth. Potent promoters providing a high level of gene expression in a bacterium belonging to the family Enterobacteriaceae can be used. Alternatively, the effect of a promoter can be enhanced by, for example, introducing a mutation into the promoter region of a gene encoding a PAP to obtain a stronger promoter function, thus resulting in the increased transcription level of a gene encoding a PAP located downstream of the promoter. Furthermore, it is known that substitution of several nucleotides in the Shine-Dalgarno ("SD") sequence, and/or in the spacer between the SD sequence and the start codon, and/or a sequence immediately upstream and/or downstream from the start codon in the ribosome-binding site greatly affects the translation efficiency of mRNA. Hence, these portions can be examples of expression regulatory regions of a gene. For example, a 20-fold range in the expression levels was found, depending on the nature of the three nucleotides preceding the start codon (Gold et al. (1981) Annu. Rev. Microbiol., 35: 365-403; Hui A. et al. (1984) EMBO J., 3: 623-629).

The hereinabove mentioned descriptions concerning overexpression of a gene encoding a PAP can be applied similarly to a gene encoding an IMP and a gene encoding an OMP, and any other genes such as, for example, the yibH gene and genes encoding L-amino acid biosynthesis pathway enzymes.

Methods which can be used to inactivate a gene include the methods for introducing gene modifications such that the modified gene encodes a completely inactive or non-functional protein as compared with the gene encoding a native protein, or the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter(s), enhancer(s), attenuator(s), ribosome-binding site(s), etc. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al. (2000) Proc. Natl. Acad. Sci. USA, 97(11): 5978-5983; Datsenko et al. (2000) Proc. Natl. Acad. Sci. USA, 97(12): 6640-6645; Zhang et al. (1998) Nature Genet., 20: 123-128) based on "Red/ET-driven integration" or "λRed/ET-mediated integration".

The copy number of a gene or the presence or absence of a gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the persons skilled in the art. These methods are described, for example, in Sambrook J., Fritsch E. F. and Maniatis T., "Molecular Cloning: A Laboratory Manual", 2$^{nd}$ ed., Cold Spring Harbor Laboratory Press (1989) or Green M. R. and Sambrook J. R. "Molecular Cloning: A Laboratory Manual", 4$^{th}$ ed., Cold Spring Harbor Laboratory Press (2012); Bernard R. Glick, Jack J. Pasternak and Cheryl L. Patten, "Molecular Biotechnology: principles and applications of recombinant DNA", 4$^{th}$ ed., Washington, DC, ASM Press (2009).

Any methods for manipulation with recombinant DNA can be used including conventional methods such as, for example, transformation, transfection, infection, conjugation, and mobilization. Transformation, transfection, infection, conjugation or mobilization of a bacterium with the DNA encoding a protein can impart to the bacterium the ability to synthesize the protein encoded by the DNA. Methods of transformation, transfection, infection, conjugation, and mobilization include any known methods. For example, a method of treating recipient cells with calcium chloride so as to increase permeability of the cells of *E. coli* K-12 to DNA has been reported for efficient DNA transformation and transfection (Mandel et al. (1970) J. Mol. Biol., 53: 159-162). Methods of specialized and/or generalized transduction were described (Morse et al. (1956) Genetics, 41(1): 142-156; Miller J. H., *Experiments in Molecular Genetics*. Cold Spring Harbor, N.Y. Cold Spring Harbor La. Press, 1972). Other methods for random and/or targeted integration of DNA into the host microorganism can be applied, for example, "Mu-driven integration/amplification" (Akhverdyan V. Z. et al. (2011)), "Red/ET-driven integration" or "λRed/ET-mediated integration" (Datsenko et al. (2000); Zhang et al. (1998) Nature Genet., 20:123-128). Moreover, for multiple insertions of desired genes in addition to Mu-driven replicative transposition (Akhverdyan V. Z. et al. (2011)) and chemically inducible chromosomal evolution based on recA-dependent homologous recombination resulted in an amplification of desired genes (Tyo et al. (2009), and other methods can be used that utilize different combinations of transposition, site-specific and/or homologous Red/ET-mediated recombinations, and/or P1-mediated generalized transduction (see, for example, Minaeva et al. (2008) BMC Biotechnology, 8: 63; Koma et al. (2012) Appl. Microbiol. Biotechnol., 93(2): 815-829).

The phrase "native to" in reference to a protein or a nucleic acid can mean that the protein or the nucleic acid is native to a particular species such as, for example, mammals, plants, insects, bacteria, and viruses. That is, a protein or a nucleic acid native to a particular species can mean the protein or the nucleic acid, respectively, that is present naturally in the species. A protein or a nucleic acid native to a particular species can be isolated from that species and sequenced using means known to the one of ordinary skill in the art. Moreover, as the amino acid sequence or the nucleotide sequence of a protein or nucleic acid, respectively, isolated from a species in which the protein or nucleic acid exists, can easy be determined, the phrase "native to" in reference to a protein or a nucleic acid can also refer to a protein or a nucleic acid that can be obtained using any means, for example, a genetic engineering technique, including recombinant DNA technology, or a chemical synthesis method, or the like, so long as the amino acid sequence of the protein or the nucleotide sequence of the nucleic acid thus obtained is identical, accordingly, to the amino acid sequence of the protein or the nucleotide sequence of the nucleic acid that is present naturally in, is expressed naturally in, and/or is produced naturally by the species. Examples of amino acid sequences native to particular species include, but are not limited to, peptides, oligopeptides, polypeptides, including proteins, specifically enzymes, and so forth. Examples of nucleotide sequences native to particular species include deoxyribonucleic acid (DNA) and ribonucleic acid (RNA), and specific examples of include, but are not limited to, expression regulatory sequences, including promoters, attenuators, terminators, and the like, genes, intergenic sequences, sequences encoding signal peptides, pro-moieties of proteins, and artificial amino acid sequences, and so forth. Specific examples of amino acid sequences and nucleotide sequences, and homologues thereof native to various species are described herein, and these examples include a YibH protein having the amino acid sequence shown in SEQ ID NO: 2, which is native to the bacterium of the species *E. coli*, which can be encoded by the yibH gene having the nucleotide sequence shown in SEQ ID NO: 1.

The phrase "non-modified", which can be used interchangeably or equivalently with the phrases "native", "natural", and "wild-type", in reference to a gene (for example, "a non-modified gene") and a protein (for example, "a non-modified protein"), can mean, respectively, a native gene and a native protein that are present naturally in, are expressed naturally in, and/or are produced naturally by an organism, specifically a non-modified strain of a bacterium. Examples of such an organism can include any organisms having the corresponding gene or protein, and specific examples thereof can include bacteria belonging to the family Enterobacteriaceae such as, for example, the *E. coli* W3110 strain, *E. coli* MG1655 strain, *P. ananatis* 13355 strain. A non-modified gene can encode a non-modified protein. [000180] The bacterium can have, in addition to the properties already mentioned, other specific properties such as various nutrient requirements, drug resistance, drug sensitivity, and drug dependence.

Method

The method as described herein can include a method for producing an L-amino acid using the bacterium as described herein. The method for producing an L-amino acid can include the steps of cultivating the bacterium as described herein in a culture medium to allow L-amino acid to be produced, excreted, secreted, and/or accumulated in the culture medium or in the bacterial cells, or both, and collecting the L-amino acid from the culture medium and/or the bacterial cells. The L-amino acid can be produced in a free form or as a salt thereof, or as a mixture thereof. For example, sodium, potassium, ammonium, and the like salts or an inner salt such as zwitterion of the L-amino acid can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to one skilled in the art. Also, L-amino acid can be produced in an adduct form thereof with, for example, another organic or inorganic compound. Specifically, a monochlorhydrate salt of an L-amino acid can be produced by the method such as monochlorhydrate salt of L-lysine (L-lysine×HCl) or monochlorhydrate salt of L-arginine (L-arginine×HCl).

The cultivation of the bacterium, and collection and, optionally, purification of the L-amino acid from the medium and the like may be performed in a manner similar to conventional fermentation methods wherein L-amino acid is produced using a microorganism. That is, the cultivation of the bacterium, and collection and purification of the L-amino acid from the medium and the like may be performed by applying the conditions that are suitable for the cultivation of the bacterium, and appropriate for the collection and purification of an L-amino acid, which conditions are well-known to persons of ordinary skill in the art.

The culture medium to be used is not particularly limited, so long as the medium contains, at least, a carbon source, and the bacterium as described herein can proliferate in it and produce L-amino acid. The culture medium for production of the L-amino acid can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolysates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, sodium thiosulphate, ammonium thiosulphate, sodium sulfide, ammonium sulfide, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. The medium can contain other various organic and inorganic components including, for example, vitamins such as vitamin B1, vitamin B2, vitamin B6, vitamin B12, nicotinic acid, and nicotinamide; required substances, for example, nucleic acids such as RNA, and amino acids; organic components containing these such as peptone, trypton, casamino acid, yeast extract, or soybean protein decomposition product; and the like, which may be present in appropriate, even if trace, amounts. Other than these, small amounts of calcium phosphate, iron ions, manganese ions, and the like may be added, if necessary. As the other various organic and inorganic components, one kind of component may be used, or two or more kinds of components may be used in combination. Furthermore, when an auxotrophic mutant strain that requires an amino acid or the like for growth thereof is used, it is preferable to supplement a required nutrient to the medium.

Cultivation can be performed under the conditions suitable for cultivating a bacterium chosen for the use in the method for producing an L-amino acid. For example, the cultivation can be performed under aerobic conditions for 16 to 72 h, or for 24 to 68 h; the culture temperature during cultivation can be controlled within 30 to 45° C., or within 30 to 37° C.; and the pH can be adjusted between 5 and 8, or between 6 and 7.5. The pH can be adjusted by using an inorganic or organic acidic or alkaline substance, as well as ammonia gas.

After cultivation, the L-amino acid can be collected from the culture medium. Specifically, the L-amino acid present outside of cells can be collected from the culture medium. Also, after cultivation, the L-amino acid can be collected from cells of the bacterium. Specifically, the cells can be disrupted, a supernatant can be obtained by removing solids such as the cells and the cell-disrupted suspension (so-called cell debris), and then the L-amino acid can be collected from the supernatant. Disruption of the cells can be performed by, for example, supersonic waves or the like. Removal of solids can be performed by, for example, centrifugation or membrane filtration. Collection of the L-amino acid from the culture medium or the supernatant etc. can be performed using, for example, a conventional technique such as concentration, crystallization, membrane treatment, ion-exchange chromatography, flash chromatography, thin-layer chromatography, high-performance liquid chromatography, and so forth. These methods may be independently used, or may be used in an appropriate combination.

EXAMPLES

The present invention will be more precisely explained below with reference to the following non-limiting examples.

Example 1. Construction of *E. coli* L-Histidine-Producing Strain EA92 Cat-$P_{tac}$-SD1-yibIH The native promoter of the yibIH operon was substituted with the Ptac promoter (Mashko et al. (2001) Biotechnologiya (Russian), 5: 3-20) using the method developed by Datsenko and Wanner (Proc. Natl. Acad. Sci. USA, 97(12), 6640-6645 (2000)) called "Red-driven integration". According to this procedure, the PCR primers P1 (SEQ ID NO: 19) and P2 (SEQ ID NO: 20), which are homologous to both a regulatory region of the yibIH operon and the gene conferring chloramphenicol resistance ($Cm^R$) in the template chromosome, were constructed. The chromosomal DNA of *E. coli* MG1655 cat-$P_{tac}$-lacZ strain (Mashko et al. (2001) Biotechnologiya (Russian), 5; 3-20) was used as a template in the PCR reaction. SD1 sequence was also included into primer P1. Conditions for PCR were as follows: denaturation for 5 minutes at 95° C.; profile for the last 30 cycles: 30 seconds at 95° C., 30 seconds at 55° C., 4 minutes at 72° C.; final step: 10 minutes at 72° C.

The amplified DNA fragment was about 1.8 kbp in size (SEQ ID NO: 21), it was purified by agarose gel electrophoresis and used for electroporation of the strain *E. coli* MG1655 (ATCC 47076) containing the plasmid pKD46 with a temperature-sensitive replication origin. The plasmid pKD46 (Datsenko et al. (2000) Proc. Natl. Acad. Sci. USA, 97(12): 6640-6645) includes a 2,154 nt (31088-33241) DNA fragment of phage λ (GenBank accession No. J02459), and contains genes of the λ Red homologous recombination system (γ, β, exo genes) under the control of arabinose-inducible $P_{araB}$ promoter. The plasmid pKD46 is necessary to integrate the PCR product into the chromosome of strain *E. coli* MG1655.

Electrocompetent cells were prepared as follows: *E. coli* MG1655/pKD46 was grown overnight at 30° C. in LB medium containing ampicillin (100 mg/L), and the culture was diluted 100 times with 5 mL of SOB medium (Sambrook et al, "Molecular Cloning A Laboratory Manual, Second Edition", Cold Spring Harbor Laboratory Press (1989)) with ampicillin and L-arabinose (1 mM). The obtained culture was grown with aeration at 30° C. to an $OD_{600}$ of approximately 0.6 and then made electrocompetent by concentrating 100-fold and washing three times with ice-cold deionized $H_2O$. Electroporation was performed using 70 μL of cells and approximately 100 ng of PCR product. Following electroporation, cells were incubated with 1 mL of SOC medium (Sambrook et al, "Molecular Cloning A Laboratory Manual, Second Edition", Cold Spring Harbor Laboratory Press (1989)) at 37° C. for 2.5 hours and then plated onto the plates containing the lysogenic broth (Sambrook and Russell, 2001 Ref.: Sambrook, J., Russell, D. W., 2001. Molecular Cloning: A Laboratory Manual (3rd ed.). Cold Spring Harbor Laboratory Press), agar 1.5% and chloramphenicol 40 mg/L and grown at 37° C. to select $Cm^R$ recombinants. Then, to eliminate the pKD46 plasmid, 2 passages on L-agar with chloramphenicol (Cm) at 42° C. were performed and the obtained colonies were tested for sensitivity to ampicillin (Amp).

Mutants containing the $P_{tac}$ promoter marked with Cm resistance gene upstream the yibIH operon were verified by PCR. Primers P3 (SEQ ID NO: 22) and P4 (SEQ ID NO: 23) were used in PCR for the verification. Conditions for PCR verification were the following: denaturation for 5 minutes at 95° C.; profile for the 30 cycles: 30 seconds at 95° C., 30 seconds at 56° C., 2 minutes 10 seconds at 72° C.; final step: 10 minutes at 72° C. PCR product, obtained in the reaction with the chromosomal DNA from parental yibIH strain *E. coli* MG1655 as a template, was 667 bp in length (SEQ ID NO: 24). PCR product, obtained in the reaction with the chromosomal DNA from mutant MG1655 cat-$P_{tac}$-SD1-yibIH strain as a template, was 2371 bp in length (SEQ ID NO: 25).

The strain MG1655 cat-$P_{tac}$-SD1-yibIH was used as a donor to transfer the cat-$P_{tac}$-SD1-yibIH expression cassette into an *E. coli* L-histidine-producing strain EA92 (see, below). The cassette was transferred by the method of general transduction using a bacteriophage P1 which was grown on *E. coli* MG1655 cat-$P_{tac}$-SD1-yibIH. Thus, the *E. coli* EA92 cat-$P_{tac}$-SD1-yibIH strain was constructed.

The *E. coli* EA92 strain was constructed as follows.

An *E. coli* EA92 strain was constructed on the basis of the *E. coli* EA83 L-histidine-producing strain (MG1655rph$^+$ ilvG15-[ΔpurR$P_{his}$-ΔhisL' hisG$^{E271K}$DCBHAFI]-[(IS5.11): (λ-attB)$P_{tac21}$-purA pitA$^-$]-[(λ-attB)$P_L$-purH]) (Malykh et al. (2018) Microb. Cell Fact., 17(1): 42). The EA83 strain was modified to overexpress aspC gene, to thereby construct the EA92 strain.

In detail, the upstream region of aspC gene was modified by the replacement of a native regulatory region with λ-phage $P_L$ promoter using λRed recombination system (Datsenko et al. (2000)). The primers P5 (SEQ ID NO: 26) and P6 (SEQ ID NO: 27) were used to construct a PCR fragment for λRed recombination that harbors an excisable cat marker and the nucleotide sequences homologous to regulatory region of aspC gene. The presence of $P_L$ promoter introduced into the chromosome was confirmed by PCR using the primers P7 (SEQ ID NO: 28) and P8 (SEQ ID NO: 29). Thus, the *E. coli* strain MG1655 cat-$P_L$-aspC was constructed. This strain was used as a donor to transfer the cat-$P_L$-aspC expression cassette into the chromosome of EA83 using the standard P1 transduction method (Moore (2011) Methods Mol. Biol., 765: 155-169). The excisable chloramphenicol resistance marker ($CmR^{ex}$) was eliminated from the *E. coli* chromosome using Xis/Int site-specific recombination system with the use of pMWts-λInt/Xis helper plasmid (Minaeva et al. (2008)). Thus, the *E. coli* EA92 strain was constructed.

Example 2. Construction of *E. coli* L-Histidine-Producing Strain EA92 Cat-$P_{tac}$-SD1-yibIH/pMIV-yeaS To construct the strain EA92 cat-$P_{tac}$-SD1-yibIH/pMIV-yeaS, the pMIV-yeaS plasmid (US20100209977A1, EP2218729 B1), which carries yeaS gene, was transformed into EA92 cat-$P_{tac}$-SD1-yibIH strain (Example 1) by means of the standard electroporation method. Thus, the *E. coli* EA92 cat-$P_{tac}$-SD1-yibIH/pMIV-yeaS strain was constructed. The control strain EA92/pMIV-yeaS was constructed using the same procedure and the strain EA92 as a host.

Example 3. Production of L-Histidine Using *E. coli* Strains

The strains EA92/pMIV-yeaS and EA92 cat-$P_{tac}$-SD1-yibIH/pMIV-yeaS (Example 2) were subjected to the production tests comparing capacity of the fermentative production of L-histidine. EA92/pMIV-yeaS and EA92 cat-$P_{tac}$-SD1-yibIH/pMIV-yeaS strains from stock tube (stored in 25% glycerol, 0.9% NaCl at −70° C.) were plated on L-agar (yeast extract—5 g/L, peptone—10 g/L, NaCl—5 g/L, agar—15 g/L) supplemented with antibiotics if necessary (Cm—40 mg/L, Amp—100 mg/L) and grown at 37° C. overnight. Cells from about 0.1 $cm^2$ of plate surface were inoculated into L-broth (tryptone—10 g/L, yeast extract—5 g/L, NaCl—5 g/L) medium (5 mL) and cultivated for 20 hours at 30° C. at 240 rpm. Then 0.1 mL of obtained culture were transferred to 2 mL of L-broth and grown at 30° C. at 240 rpm to OD (600 nm) about 0.6 to obtain seed culture. Then 0.1 mL of seed culture were inoculated into 2 mL of a fermentation medium shown in Table 1 in the test tubes (23 mm internal diameter; all test tubes were 200 mm long) to initiate cultivation. The cultivation was carried out at 32° C. with agitation 240 rpm for 65 hrs until glucose consumption.

TABLE 1

Composition of fermentation medium

| Component | Final concentration (g/L) |
|---|---|
| Glucose | 50.0 |
| Mameno* | 0.2 (as the amount of nitrogen) |
| L-aspartate | 1.0 |
| $(NH_4)_2SO_4$ | 18.0 |
| KCl | 1.0 |
| $KH_2PO_4$ | 0.5 |
| $MgSO_4$•$7H_2O$ | 0.4 |
| $FeSO_4$•$7H_2O$ | 0.02 |
| $MnSO_4$•$5H_2O$ | 0.02 |
| $ZnSO_4$•$7H_2O$ | 0.02 |
| Adenosine | 0.2 |
| Thiamine-HCl | 0.001 |

TABLE 1-continued

| Composition of fermentation medium | |
|---|---|
| Component | Final concentration (g/L) |
| Betaine | 2.0 |
| $CaCO_3$ | 60.0 |

*Mameno is the soybean meal hydrolysate (Ajinomoto Co., Inc.).

Glucose, $MgSO_4 \cdot 7H_2O$, betaine and $CaCO_3$ were sterilized separately. The pH was adjusted to 6.0 by 6 M KOH before sterilization.

After cultivation, accumulated L-histidine was measured using thin-layer chromatography (TLC). TLC plates (10×20 cm) were coated with 0.11 mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed with a mobile phase consisting of iso-propanol:aceton:25% aqueous ammonia:water=6:6:1.5:1 (v/v). A solution of ninhydrin (1%, w/v) in acetone was used as the visualizing reagent. After development, plates were dried and scanned with the Camag TLC Scanner 3 in absorbance mode with detection at 520 nm using winCATS software (version 1.4.2).

The results of three independent test tube fermentations (as average values) of two clones are shown in Table 2. As one can see from the Table 2, the *E. coli* EA92 cat-$P_{tac}$-SD1-yibIH/pMIV-yeaS strain caused a higher amount of accumulation of L-histidine as compared with the parent EA92/pMIV-yeaS strain.

TABLE 2

| Production of L-histidine. | | |
|---|---|---|
| Strain | $OD_{600}$ | His, g/L |
| *E. coli* EA92/pMIV-yeaS (control) | 9.3 | 3.2 |
| *E. coli* EA92 cat-$P_{tac}$-SD1-yibIH/pMIV-yeaS, clone 1 | 8.2 | 4.5 |
| *E. coli* EA92 cat-$P_{tac}$-SD1-yibIH/pMIV-yeaS, clone 2 | 8.9 | 4.2 |

(n = 3)

Example 4. Construction of pGL2-Ptac-SD1 Plasmid

To construct pGL2-$P_{tac}$-SD1 plasmid (FIG. 1), the pGL2 plasmid, which carries the ori of pSC101, the φ80-attP site of φ80 phage, and an excisable $Cm^R$ marker bracketed by λ-attL/attR sites (Hook C. D. et al. (2016) J. Microbiol. Methods, 130: 83-91), was used as a start material. A DNA fragment containing whole pGL2-$P_{tac}$ sequence was obtained by PCR from pGL2 plasmid as a template with primers P9 (SEQ ID NO: 30) and P10 (SEQ ID NO: 31). Primer P10 contained sequence of $P_{tac}$ promoter. Conditions for PCR were as follows: denaturation for 3 minutes at 95° C.; profile for the last 30 cycles: 20 seconds at 98° C., 15 seconds at 67° C., 3 minutes 20 seconds at 72° C.; final step: 5 minutes at 72° C. (KAPA HiFi HotStart ReadyMixPCR Kit, Roche). Obtained DNA fragment was digested with restriction enzyme NotI and was subjected to self-ligation to construct pGL2m-$P_{tac}$ plasmid.

Obtained pGL2-$P_{tac}$ plasmid was used as a starting material for pGL2-$P_{tac}$-SD1 construction. A DNA fragment containing the entire pGL2-$P_{tac}$-SD1 sequence was obtained by next round of PCR from pGL2-$P_{tac}$ plasmid as a template with primers P9 (SEQ ID NO: 30) and P11 (SEQ ID NO: 32). Primer P11 contained SD1 sequence. Conditions for PCR were as follows: denaturation for 3 minutes at 95° C.; profile for the last 30 cycles: 20 seconds at 98° C., 15 seconds at 68° C., 3 minutes 20 seconds at 72° C.; final step: 5 minutes at 72° C. (KAPA HiFi HotStart ReadyMixPCR Kit, Roche). Obtained DNA fragment was digested with restriction enzyme NotI and was subjected to self-ligation to construct pGL2m-$P_{tac}$-SD1 plasmid.

Example 5. Construction of pGL2-$P_{tac}$-SD1-yibH Plasmid

To construct the pGL2-$P_{tac}$-SD1-yibH plasmid (SEQ ID NO: 33, FIG. 2), the yibH gene (SEQ ID NO: 1) was in vivo cloned on pGL2-$P_{tac}$-SD1 plasmid (FIG. 1) by means of pKD46-mediated λRed-recombination. The pGL2-$P_{tac}$-SD1 was treated with NotI restriction enzyme and the resulting linear fragment was purified by electrophoresis in agarose gel and electroporated into the *E. coli* MG1655 strain containing the pKD46 plasmid (Datsenko et al. (2000), Proc. Natl. Acad. Sci. USA, 97(12): 6640-6645) having a temperature-sensitive replication origin. The resulting plasmid pGL2-$P_{tac}$-SD1-yibH was obtained from one of independently grown clones on the plate with chloramphenicol (Cm) as the selectable marker.

The presence of yibH gene on pGL2-$P_{tac}$-SD1-yibH plasmid was verified using PCR. The primers P12 (SEQ ID NO: 34) and P13 (SEQ ID NO: 35) were used for PCR verification from 5'-end of yibH gene. The primers P14 (SEQ ID NO: 36) and P15 (SEQ ID NO: 37) were used for PCR verification from 3'-end yibH gene. A DNA from the pGL2-$P_{tac}$-SD1-yibH plasmid (SEQ ID NO: 33, FIG. 2) was used as a template. Conditions for the PCR verification from 5'-end were as follows: denaturation for 3 minutes at 95° C.; profile for the 30 cycles: 30 seconds at 95° C., 30 seconds at 53° C., 30 seconds at 72° C.; final elongation: 5 minutes at 72° C. Conditions for the PCR verification from 3'-end were as follows: denaturation for 3 minutes at 95° C.; profile for the 30 cycles: 30 seconds at 95° C., 30 seconds at 56° C., 50 seconds at 72° C.; final elongation: 5 minutes at 72° C. The PCR products 1 and 2, obtained in the reaction using the DNA from the pGL2-$P_{tac}$-SD1-yibH plasmid as a template, were 272 bp (SEQ ID NO: 38) and 750 bp (SEQ ID NO: 39) in length, accordingly, as desired.

Example 6. Construction of the *E. coli* Strain MG1655 Cat-$P_{Ltac}$-tolC

To construct the cat-$P_{Ltac}$-tolC expression cassette, the upstream region of tolC gene was modified by replacement of the native regulatory region with the $\lambda P_{Ltac}$ promoter, which is a hybrid of $\lambda P_L$ and $\lambda P_{tac}$ promoters (US2015203881 A1). To construct the PCR fragment for λRed recombination with an excisable cat marker and flanking sequences homologous to the tolC regulatory region, the primers P16 (SEQ ID NO: 40) and P17 (SEQ ID NO: 41) were used.

The amplified DNA fragment was purified by agarose gel electrophoresis and used for electroporation of the strain *E. coli* MG1655 containing the plasmid pKD46 with a temperature-sensitive replication origin. Electrocompetent cells were prepared as described previously.

Mutants containing the $P_{Ltac}$ promoter marked with Cm resistance gene upstream the tolC gene were verified by PCR. Primers P18 (SEQ ID NO: 42) and P19 (SEQ ID NO: 43) were used in PCR for the verification. Conditions for PCR verification were the following: denaturation for 5 minutes at 95° C.; profile for the 30 cycles: 30 seconds at 95° C., 30 seconds at 56° C., 2.5 minutes at 72° C.; final step: 7 minutes at 72° C. PCR product, obtained in the reaction with the chromosomal DNA from mutant MG1655 cat-$P_{Ltac}$-tolC strain as a template, was about 2279 bp in length (SEQ ID NO: 44).

Example 7. Construction of the *E. coli* L-Valine-Producing Strain H81 $P_{Ltac}$-tolC IS5.8:tetA-tetR-2Ter-$P_{yeaS}$-yeaS/pGL2-$P_{tac}$-SD1-yibH At the first step, the cat-$P_{Ltac}$-tolC expression cassette (Example 6) harboring the overexpressed tolC gene was transferred into the *E. coli* valine-producing strain H81 by means of P1-transduction (Miller, J. H. (1972) "Experiments in Molecular Genetics", Cold Spring Harbor Lab. Press, Plainview, NY) to obtain the strain H81 cat-$P_{Ltac}$-tolC.

The strain H81 was deposited in the Russian National Collection of Industrial Microorganisms (VKPM; 1st Dorozhny proezd, 1, Moscow 117545, Russian Federation) on Jan. 30, 2001 under accession number VKPM B-8066, and transferred from the original deposit to international deposit under the Budapest Treaty on Feb. 1, 2002.

The $CmR^{ex}$ marker was eliminated from the *E. coli* H81 cat-$P_{Ltac}$-tolC chromosome using a Xis/Int site-specific recombination system using the pMWts-λInt/Xis helper plasmid (Minaeva et al. (2008)). Thus, the *E. coli* H81 $P_{Ltac}$-tolC strain was constructed.

At the second step, the IS5.8:tetA-tetR-2ter-$P_{yeaS}$-yeaS expression cassette (Example 8), harboring the overexpressed yeaS gene, was transferred into the *E. coli* L-valine-producing strain H81 $P_{Ltac}$-tolC by means of P1-transduction as described above. Thus, the *E. coli* strain H81 $P_{Ltac}$-tolC IS5.8:tetA-tetR-2Ter-$P_{yeaS}$-yeaS was obtained.

Finally, the plasmid pGL2-$P_{tac}$-SD1-yibH (SEQ ID NO: 33, FIG. 2), encoding the third component of tripartite efflux system, PAP YibH, was used for electrotransformation into the strain H81 $P_{Ltac}$-tolC IS5.8:tetA-tetR-2Ter-$P_{yeaS}$-yeaS. Electrocompetent cells were prepared as follows: H81 $P_{Ltac}$-tolC IS5.8:tetA-tetR-2Ter-$P_{yeaS}$-yeaS was grown overnight at 30° C. in LB-medium (Luria-Bertani broth, also referred to as lysogenic broth; Sambrook J. and Russell D. W., Molecular Cloning: A Laboratory Manual (3rd ed.), Cold Spring Harbor Laboratory Press, 2001) and the culture was diluted 100 times with 5 mL of LB-medium. The obtained culture was grown with aeration at 30° C. to an $OD_{600}$ of approximately 0.7 and then made electrocompetent by concentrating 100-fold and washing three times with ice-cold deionized $H_2O$. Electroporation was performed using 100 μL of cells and approximately 200 ng of plasmid.

Following electroporation, cells were incubated with 1 mL of SOC medium (Sambrook et al, "Molecular Cloning A Laboratory Manual, Second Edition", Cold Spring Harbor Laboratory Press (1989)) at 37° C. for 2.5 hours and then plated onto the plates containing the lysogenic broth (Sambrook and Russell, 2001 Ref.: Sambrook, J., Russell, D. W., 2001. Molecular Cloning: A Laboratory Manual (3rd ed.). Cold Spring Harbor Laboratory Press), agar 1.5% and chloramphenicol 50 mg/L and grown at 37° C. to select $Cm^R$ recombinants. Thus, the *E. coli* strain H81 $P_{Ltac}$-tolC IS5.8:tetA-tetR-2Ter-$P_{yeaS}$-yeaS/pGL2-$P_{tac}$-SD1-yibH having the $Cm^R$ marker on the plasmid was constructed.

The presence of the transferred cat-$P_{Ltac}$-tolC expression cassette harboring the overexpressed tolC gene in the *E. coli* H81 chromosome was verified by PCR using primers P18 (SEQ ID NO: 42) and P19 (SEQ ID NO: 43), and the chromosomal DNA from the *E. coli* H81 cat-$P_{Ltac}$-tolC strain as a template. Conditions for PCR were as follows: denaturation for 3 minutes at 95° C.; profile for the 25 cycles: 30 seconds at 95° C., 2 minutes 30 seconds at 58° C., 1 minute at 72° C.; final elongation: 1 minute at 72° C. The length of the obtained PCR fragment was 2279 bp as desired.

The elimination of the $CmR^{ex}$ marker from the *E. coli* H81 cat-$P_{Ltac}$-tolC-$Cm^R$ chromosome was verified by PCR. The primers P18 and P19, and the chromosomal DNA from the *E. coli* H81 $P_{Ltac}$-tolC strain as a template were used for the verification. Conditions for PCR were as follows: denaturation for 3 minutes at 95° C.; profile for the 25 cycles: 30 seconds at 95° C., 2 minutes 30 seconds at 58° C., 1 minute at 72° C.; final elongation: 1 minute at 72° C. The length of the obtained PCR fragment meets expectations.

The presence of the transferred IS5.8:tetA-tetR-2Ter-$P_{yeaS}$-yeaS expression cassette in the *E. coli* H81 chromosome was verified by PCR using primers P20 (SEQ ID NO: 45) and P21 (SEQ ID NO: 46), and the chromosomal DNA from the *E. coli* H81 $P_{Ltac}$-tolC-IS5.8:tetA-tetR-2Ter-$P_{yeaS}$-yeaS strain as a template. Conditions for PCR were as follows: denaturation for 3 minutes at 95° C.; profile for the 30 cycles: 30 seconds at 95° C., 30 seconds at 51° C., 1.5 minutes at 72° C.; final elongation: 7 minutes at 72° C. The length of the obtained PCR fragment was 1597 bp as desired.

Figure 3:
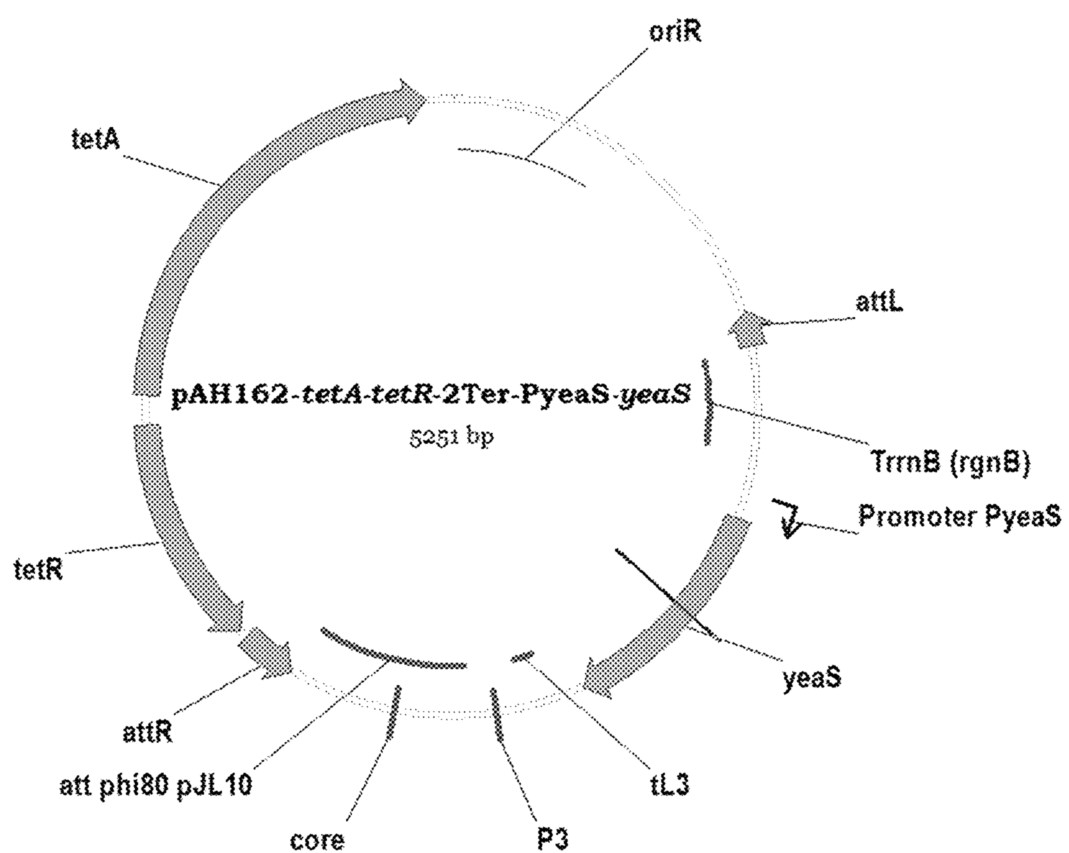
FIG. 3 illustrates the pAH162-tetA-tetR-2Ter-$P_{yeaS}$-yeaS plasmid.

Example 8. Construction of *E. coli* MG1655 IS5.8:tetA-tetR-2Ter-$P_{yeaS}$-yeaS Strain At the first step, a pAH162-tetA-tetR-2Ter-$P_{yeaS}$-yeaS integrative plasmid (SEQ ID NO: 47, FIG. 3) was constructed. The yeaS gene having its native regulation elements was amplified from *E. coli* MG1655 K-12 chromosome by using primers P22 (SEQ ID NO: 48) and P23 (SEQ ID NO: 49). The chromosome of the wild-type *E. coli* MG1655 strain (ATCC 47076), which originates from the prototype wild-type K-12 strain, was used as a template. Conditions for PCR were as follows: denaturation for 3 minutes at 95° C.; profile for the last 30 cycles: 20 seconds at 95° C., 30 seconds at 55° C., 1 minute at 72° C.; final step: 5 minutes at 72° C. (Pfu DNA Polymerase, Promega). The length of the obtained PCR fragment was 808 bp as desired.

The $P_{yeaS}$-yeaS DNA fragment was blunted and ligated with the pAH162-tetA-tetR-2Ter (Minaeva N. I. et al., 2008) which was preliminarily treated with SmaI restrictase. Thus, the pAH162-tetA-tetR-2Ter-$P_{yeaS}$-yeaS integrative plasmid (SEQ ID NO: 47, FIG. 3) was obtained.

The presence of $P_{yeaS}$-yeaS fragment on the resulting pAH162-tetA-tetR-2Ter-$P_{yeaS}$-yeaS integrative plasmid was verified using PCR with the primers P24 (SEQ ID NO: 50) and P25 (SEQ ID NO: 51). A DNA from the pAH162-tetA-tetR-2Ter-$P_{yeaS}$-yeaS plasmid (SEQ ID NO: 47, FIG. 3) was used as a template. Conditions for the PCR were as follows: denaturation for 3 minutes at 95° C.; profile for the 30 cycles: 30 seconds at 95° C., 30 seconds at 51° C., 1 minute at 72° C.; final elongation: 7 minutes at 72° C. The PCR product (SEQ ID NO: 52), obtained in the reaction using the DNA from the pAH162-tetA-tetR-2Ter-$P_{yeaS}$-yeaS plasmid as a template, was 1012 bp in length as desired.

At the next step, the pAH162-tetA-tetR-2Ter-$P_{yeaS}$-yeaS plasmid was used for φ80-Int-mediated integration of $P_{yeaS}$-yeaS DNA fragment into the artificial φ80-attB site of the chromosome of *E. coli* MG1655 Δ(φ80-attB) IS5.8:φ80-attB strain (Haldimann et al. (2001) J. Bacteriol., 183(21): 6384-6393; Minaeva et al. (2008) BMC Biotechnol., 8: 63). The pAH123 plasmid (Haldimann A. and Wanner B. L., 2001; GenBank, accession No.: AY048726), which contains the thermoinducible φ80-int gene, was used to provide φ80-Int-mediated integration. A vector part of the integrated recombinant plasmid, including oriRγ and tetracycline resistance marker gene bracketed by attLIR sites of phage λ (Sanger F. et al. (1982) J. Mol. Biol., 162: 729-773), was eliminated from the *E. coli* chromosome using Xis/Int site-specific recombination system with the use of pMWts-λInt/Xis helper plasmid (Minaeva et al. (2008)).

The presence of the integrated pAH162-tetA-tetR-2Ter-$P_{yeaS}$-yeaS DNA plasmid in artificial φ80-attB site of the *E. coli* MG1655 Δ(φ80-attB) IS5.8:φ80-attB chromosome was verified by PCR using primers P20 (SEQ ID NO: 45) and P21 (SEQ ID NO: 46), and the chromosomal DNA from the *E. coli* MG1655 IS5.8:tetA-tetR-2Ter-$P_{yeaS}$-yeaS strain as a template. Conditions for PCR were as follows: denaturation for 3 minutes at 95° C.; profile for the 30 cycles: 30 seconds at 95° C., 30 seconds at 51° C., 1.5 minutes at 72° C.; final elongation: 7 minutes at 72° C. The PCR product, obtained in the reaction using the chromosomal DNA from the *E. coli* MG1655 IS5.8:$P_{yeaS}$-yeaS strain as a template, was 1597 bp in length as desired.

Example 9. Production of L-Valine Using *E. coli* Strains

*E. coli* strains H81 $P_{Ltac}$-tolC IS5.8:tetA-tetR-2Ter-$P_{yeaS}$-yeaS and H81 $P_{Ltac}$-tolC IS5.8:tetA-tetR-2Ter-$P_{yeaS}$-yeaS/pGL2-$P_{tac}$-SD1-yibH were separately cultivated at 30° C. for 18 hours in a nutrient broth. The obtained cultures (0.2 mL each) were inoculated into 2 mL of a fermentation medium shown in Table 3 in a 20×200-mm test tubes, and cultivated at 30° C. for 60 hours on a rotary shaker at 250 rpm until glucose consumption.

After the cultivation, the amount of L-valine which accumulated in the medium was measured by TLC.

TABLE 3

Composition of fermentation medium

| Component | Final concentration (g/L) |
|---|---|
| Glucose | 60.0 |
| $(NH_4)_2SO_4$ | 18.0 |
| $KH_2PO_4$ | 1.8 |
| $MgSO_4$•$7H_2O$ | 1.0 |
| LB-medium | 0.4 |
| Thiamine•HCl | 0.2 |
| $CaCO_3$ | 24.0 |

$CaCO_3$ was dry-heat sterilized at 180° C. for 2 h. The pH is adjusted to 7.0.

The results of eight independent test tube fermentations (as average values) are shown in Table 4. As one can see from the Table 4, the modified *E. coli* H81 $P_{Ltac}$-tolC IS5.8:tetA-tetR-2Ter-$P_{yeaS}$-yeaS/pGL2-Ptac-SD1-yibH strain was able to accumulate a higher amount of L-valine as compared with the control *E. coli* H81 $P_{Ltac}$-tolC IS5.8:tetA-tetR-2Ter-$P_{yeaS}$-yeaS strain.

TABLE 4

Production of L-valine.

| Strain | $OD_{600}$ | Val, g/L |
|---|---|---|
| *E. coli* H81 $P_{Ltac}$-tolC IS5.8::tetA-tetR-2Ter-$P_{yeaS}$-yeaS (control) | 12.4 | 20.4 |
| *E. coli* H81 $P_{Ltac}$-tolC IS5.8::tetA-tetR-2Ter-$P_{yeaS}$-yeaS/pGL2-$P_{tac}$-SD1-yibH | 17.5 | 25.5 |

(n = 8)

Example 10. Construction of *P. ananatis* L-Cysteine-Producing Strain EYP $P_{nlp8}$-tolC (s) pGL2-$P_{tac}$-SD1-yibH A *P. ananatis* EYP197(s) strain was constructed as described in RU2458981 C2 or WO2012/137689. That is, *P. ananatis* strain EYP197(s) was constructed from *P. ananatis* SC17 (FERM BP-11091) by introducing cysE5 and yeaS genes and replacing the native promoter of cysPTWA gene cluster with Pnlp8 promoter.

A promoter region of 200 nucleotides in length of the tolC gene in the strain EYP197 (s) was substituted with the $P_{nlp8}$ promoter. PCR was carried out using the plasmid DNA pMW-Km-Pnlp8 (see RU2458981 C2) as a template and primers P26 (SEQ ID NO: 53) and P27 (SEQ ID NO: 54). Conditions for PCR were as follows: denaturation step for 3 minutes at 95° C.; profile for two first cycles: 1 minute at 95° C., 30 seconds at 59° C., 60 seconds at 72° C.; profile for the last 30 cycles: 30 seconds at 92° C., 30 seconds at 59° C., 60 seconds at 72° C.; final step: 5 minutes at 72° C. The amplified DNA fragment was about 1,6 kbp in length, and it was purified using agarose gel electrophoresis. The obtained fragment was used to transform *P. ananatis* SC17 strain (U.S. Pat. No. 6,596,517 B2) by electroporation. The resulting transformants were plated on plates with LB agar containing kanamycin (20 mg/L), and the plates were incubated at 34° C. overnight until individual colonies were visible. The desired transformants were identified by PCR analysis using primers P28 (SEQ ID NO: 55) and P29 (SEQ ID NO: 56). Thus, the *P. ananatis* SC17-$P_{nlp8}$-tolC strain was constructed.

To transfer the tolC gene with the $P_{nlp8}$ promoter into the strain EYP197 (s), a chromosomal DNA was isolated from the strain SC17-$P_{nlp8}$-tolC. 10 μg of the chromosomal DNA was used to transform *P. ananatis* EYP197 (s) by electroporation. The resulting transformants were plated on plates with LB agar containing kanamycin (20 mg/L), and the plates were incubated at 34° C. overnight until individual colonies were visible. The desired transformants were identified by PCR analysis using primers P28 (SEQ ID NO: 55) and P29 (SEQ ID NO: 56). Thus, the *P. ananatis* EYP $P_{nlp8}$-tolC strain was constructed.

The *P. ananatis* EYP $P_{nlp8}$-tolC strain was cured from the kanamycin resistance gene (kan) and transformed with the plasmid RSF-int-xis (US20100297716 A1) using electroporation. The resulting transformants were plated on plates with LB agar containing tetracycline (10 mg/L), and the plates were incubated at 30° C. overnight until individual colonies were visible. The desired transformants were identified by selecting variants which were sensitive to kanamycin (40 mg/L). Thus, the *P. ananatis* EYP $P_{nlp8}$-tolC (s) strain was constructed.

Figure 2:
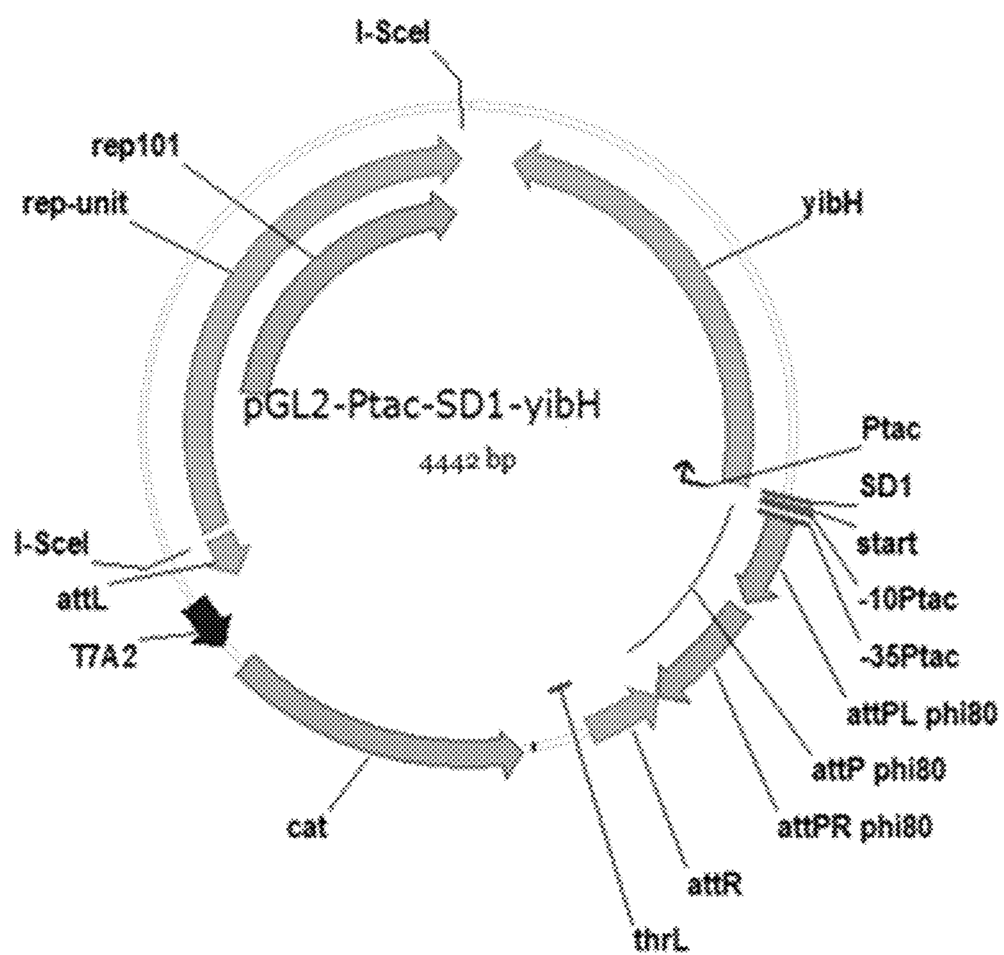
FIG. 2 illustrates the pGL2-$P_{tac}$-SD1-yibH plasmid.

The strain EYP $P_{nlp8}$-tolC (s) was transformed by plasmid pGL2-$P_{tac}$-SD1-yibH (SEQ ID NO: 33, FIG. 2). Thus, the *P. ananatis* EYP $P_{nlp8}$-tolC (s) pGL2-$P_{tac}$-SD1-yibH strain was constructed.

Example 11. Production of L-Cysteine Using *P. ananatis* Strains

The *P. ananatis* EYP $P_{nlp8}$-tolC (s) and EYP $P_{nlp8}$-tolC (s) pGL2-$P_{tac}$-SD1-yibH strains were each cultivated at 32° C. for 18 hours in LB liquid culture medium. Then, 0.2 mL of the obtained cultures were inoculated into 2 mL of a fermentation medium shown in Table 5 in 20×200-mm test tubes and cultivated at 32° C. for 24 hours on a rotary shaker at 250 rpm until glucose was consumed.

TABLE 5

Composition of fermentation medium

| Component | Final concentration (g/L) |
|---|---|
| Glucose | 40.0 |
| $(NH_4)_2S_2O_3$ | 12.0 |
| $KH_2PO_4$ | 1.5 |
| $MgSO_4$•$6H_2O$ | 0.825 |
| Thiamine•HCl | 0.1 |
| $CaCO_3$ | 25.0 |
| LB medium | 4% (v/v) |

The fermentation medium was sterilized at 116° C. for 30 min, except that glucose, $(NH_4)_2S_2O_3$ and $CaCO_3$ were sterilized separately as follows: glucose at 110° C. for 30 min, $(NH_4)_2S_2O_3$ by means of filtering through 0.2 µm-membrane, and $CaCO_3$ at 116° C. for 30 min. The pH was adjusted to 7.0 by KOH solution.

After cultivation, the amount of L-cysteine which accumulated in the medium was determined by the method described by Gaitonde M. K. (Biochem J.; 104(2):627-33 (1967)) with some modifications as follows: 150 µL of each sample was mixed with 150 µL of 1 M $H_2SO_4$ and incubated for 5 minutes at 20° C. Then, 700 µl $H_2O$ was added to the mixture, 150 µL of the obtained mixture was transferred into the new vial and 800 µL of solution A (1 M Tris pH 8.0, 5 mM dithiothreitol (DTT)) was added. The obtained mixture was incubated for 5 minutes at 20° C., rotated for 10 minutes at 13000 rpm, and 100 µL of the mixture was transferred into a 20×200-mm test tube. Then, 400 µL $H_2O$, 500 µL ice acetic acid, and 500 µL of solution B (0.63 g ninhydrin, 10 mL ice acetic acid, 10 mL 36% HCl) were added, and the mixture was incubated for 10 minutes in a boiling water bath. Then 4.5 mL ethanol was added and the $OD_{560}$ was determined. The concentration of cysteine was calculated using the formula: C (Cys, g/L)=11.3×$OD_{560}$.

The results of six independent test tube fermentations are shown in Table 6. As one can be seen from the Table 6, the modified *P. ananatis* EYP $P_{nlp8}$-tolC (s) pGL2-$P_{tac}$-SD1-yibH strain was able to accumulate a higher amount of L-cysteine as compared with the control *P. ananatis* EYP $P_{nlp8}$-tolC (s) strain.

TABLE 6

Production of L-cysteine.

| Strain | Cys, g/L | % |
|---|---|---|
| *P. ananatis* EYP $P_{nlp8}$-tolC (s) (control) | 0.16 | 100 |
| *P. ananatis* EYP $P_{nlp8}$-tolC (s) pGL2-$P_{tac}$-SD1-yibH | 0.18 | 112 |

(n = 6)

Example 12. Construction of *E. coli* L-Tryptophan-Producing Strain IB119 $P_{tac3000}$-tolC $P_{tac3000}$-yibIH The native promoter of the tolC gene was substituted with the $P_{tac3000}$ promoter (Katashkina et al. (2005) Mol. Biol. (Mosk.), 39(5): 823-831) using the method developed by Datsenko and Wanner (Proc. Natl. Acad. Sci. USA, 97(12), 6640-6645 (2000)) called "Red-driven integration". According to this procedure, the PCR primers P30 (SEQ ID NO: 59), which is homologous to the 5'-part of tolC gene and the $P_{tac3000}$ promoter having a half of $O_{lac}$, and P31 (SEQ ID NO: 60), which is homologous to the regulatory region of the tolC gene and the gene conferring chloramphenicol resistance ($Cm^R$) in the template chromosome, were constructed. The chromosomal DNA of *E. coli* MG1655 cat-$P_{tac3000}$-lacZ strain (Katashkina et al. (2005) Mol. Biol. (Mosk.), 39(5): 823-831) was used as a template in the PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final step: 5 min at 72° C. The resulting 1782 bp DNA fragment was purified by "Silica Bead DNA Gel Extraction Kit" (Thermo Scientific) and used for electroporation of the strain MG1655 containing the plasmid pKD46. $Cm^R$ recombinants were selected, and the introduction of $P_{tac3000}$ promoter was confirmed by PCR using primers P32 (SEQ ID NO: 61) and P33 (SEQ ID NO: 62). Conditions for PCR were as follows: denaturation for 5 min at 94° C.; profile for 25 cycles: 30 sec at 94° C., 30 sec at 59° C., 90 sec at 72° C.; final elongation for 5 min at 72° C. DNA fragment obtained in the reaction with DNA of the cells of the parent strain MG1655 as a template, was 383 bp in length. DNA fragment obtained in the reaction with DNA of the cells of the strain MG1655 cat-$P_{tac3000}$-tolC as a template, was 2001 bp in length.

The resulting strain MG1655 cat-$P_{tac3000}$-tolC was used as a donor to transfer the cat-$P_{tac3000}$-tolC expression cassette into the *E. coli* strain D3119 by the method of P1-transduction (Sambrook J. et al., "Molecular Cloning A Laboratory Manual, 2nd Edition", Cold Spring Harbor Laboratory Press (1989)). Construction of the *E. coli* IB119 strain is described below. $Cm^R$ recombinants were selected, and the introduction of $P_{tac3000}$ promoter was verified by PCR as described above. After that, λ-Int/Xis-mediated excision of $Cm^R$ marker was performed. Excision was confirmed by PCR as described above. DNA fragment obtained in the reaction with DNA of the cells of the parent strain IB119 cat-$P_{tac3000}$-tolC used as a template, was 2001 bp in length. DNA fragment obtained in the reaction with DNA of the cells of the strain IB119 attB-$P_{tac3000}$-tolC as a template, was 395 bp in length. As a result, the strain IB119 attB-$P_{tac3000}$-tolC was constructed.

The native promoter of the yibIH operon was substituted with the $P_{tac3000}$ promoter (Katashkina et al. (2005) Mol. Biol. (Mosk.), 39(5): 823-831) using the method of Red-dependent integration described above. According to this procedure, the PCR primers P34 (SEQ ID NO: 63), which is homologous to the 5'-part of yibIH operon and the $P_{tac3000}$ promoter having a half of $O_{lac}$, and P35 (SEQ ID NO: 64), which is homologous to the regulatory region of the yibIH operon and the gene conferring chloramphenicol resistance ($Cm^R$) in the template chromosome, were constructed. The chromosomal DNA of *E. coli* MG1655 cat-$P_{tac3000}$-lacZ strain (Katashkina et al. (2005) Mol. Biol. (Mosk.), 39(5): 823-831) was used as a template in the PCR reaction.

Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final step: 5 min at 72° C. The resulting 1782 bp DNA fragment was purified by "Silica Bead DNA Gel Extraction Kit" (Thermo Scientific) and used for electroporation of the strain MG1655 containing the plasmid pKD46. $Cm^R$ recombinants were selected, and the introduction of $P_{tac3000}$ promoter was confirmed by PCR using primers P36 (SEQ ID NO: 65) and P37 (SEQ ID NO: 66). Conditions for PCR were as follows: denaturation for 5 min at 94° C.; profile for 25 cycles: 30 sec at 94° C., 30 sec at 59° C., 1 min at 72° C.; final elongation for 5 min at 72° C. DNA fragment obtained in the reaction with DNA of the cells of the parent strain MG1655 as a template, was 369 bp in length. DNA fragment obtained in the reaction with DNA of the cells of the strain MG1655 cat-$P_{tac3000}$-yibIH as a template, was 2070 bp in length.

The resulting strain MG1655 cat-$P_{tac3000}$-yibIH was used as a donor to transfer the cat-$P_{tac3000}$-yibIH expression cassette into the strain IB119 attB-$P_{tac3000}$-tolC by the method of P1-transduction. $Cm^R$ recombinants were selected, and the introduction of $P_{tac3000}$ promoter was verified by PCR as described above. Thus, the strain IB119 attB-$P_{tac3000}$-tolC cat-$P_{tac3000}$-yibIH was constructed.

The *E. coli* IB119 strain was constructed from the *E. coli* MG1655 ($rph^{wt}$ ilvG-15) strain (Biryukova et al. (2010) Genetika (Russian), 46: 349-355) as follows.

An *E. coli* IB100 strain, the construction of which is described below, had the MG1655 ($rph^{wt}$ ilvG-15) ΔtrpR ΔtnaA ΔtyrR Δ(tyrA-pheA) genotype. All deletions were obtained in the chromosome of MG1655 strain (ATCC 47076) by the method of Red-dependent integration described above. According to this procedure, the PCR primers P38 (SEQ ID NO: 67) and P39 (SEQ ID NO: 68), which are homologous to both region adjacent to the trpR gene and the region adjacent to the cat gene conferring chloramphenicol resistance in the template plasmid, were constructed. The plasmid pMW118-attL-cat-attR (Katashkina et al. (2005) Mol. Biol. (Mosk.), 39(5): 823-831) was used as a template in PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final elongation for 5 min at 72° C. The obtained 1709 bp DNA fragment was purified by "Silica Bead DNA Gel Extraction Kit" (Thermo Scientific) and used for electroporation of the *E. coli* strain MG1655 containing the plasmid pKD46. $Cm^R$ recombinants were selected, and the deletion of the trpR gene marked with $Cm^R$ gene in the selected mutants was verified by PCR using primers P40 (SEQ ID NO: 69) and P41 (SEQ ID NO: 70). Conditions for PCR verification were as follows: denaturation for 3 min at 95° C.; profile for the 25 cycles: 30 sec at 95° C., 30 sec at 55° C., 90 sec at 72° C.; final elongation for 5 min at 72° C. Thus, the strain MG1655 ΔtrpR:cat was constructed.

The strain MG1655 ΔtrpR:cat was used as a donor for P1-transduction of the trpR gene deletion into the strain MG1655 ($rph^{wt}$ ilvG-15) (Biryukova et al. (2010) Genetika (Russian), 46: 349-355). $Cm^R$ recombinants were selected, and the trpR gene deletion in the selected mutants was verified by PCR as described above. After that, λ-Int/Xis-mediated excision of $Cm^R$ marker from the strain MG1655 ($rph^{wt}$ ilvG-15) ΔtrpR:cat was performed, and the excision was confirmed by PCR as described above. As a result, the strain MG1655 ($rph^{wt}$ ilvG-15) ΔtrpR:attB was constructed.

Other deletions were obtained independently in the same way using primers P42 (SEQ ID NO: 71) and P43 (SEQ ID NO: 72) for tnaA gene deletion, P44 (SEQ ID NO: 73) and P45 (SEQ ID NO: 74) for tyrR gene deletion, and P46 (SEQ ID NO: 75) and P47 (SEQ ID NO: 76) for tyrA-pheA genes deletion. Obtained DNA fragments were purified by "Silica Bead DNA Gel Extraction Kit" (Thermo Scientific) and used for electroporation of the *E. coli* strain MG1655 containing the plasmid pKD46. $Cm^R$ recombinants were selected, and the deletions of the tnaA, tyrR, and tyrA-pheA genes marked with $Cm^R$ gene in the selected mutants were verified by PCR using primers P48 (SEQ ID NO: 77) and P49 (SEQ ID NO: 78), P50 (SEQ ID NO: 79) and P51 (SEQ ID NO: 80), and P52 (SEQ ID NO: 81) and P53 (SEQ ID NO: 82) respectively. Thus, the strains MG1655 ΔtnaA:cat, MG1655 ΔtyrR:cat, and MG1655 Δ(tyrA-pheA):cat were constructed. These three strains were used as donors for sequential P1-transduction of the tnaA, tyrR and tyrA-pheA gene deletions into the strain MG1655 ($rph^{wt}$ ilvG-15) ΔtrpR:attB with subsequent marker excision. Excision was confirmed by PCR as described above. As a result, the strain MG1655 ($rph^{wt}$ ilvG-15) ΔtrpR:attB ΔtnaA:attB ΔtyrR:attB Δ(tyrA-pheA):attB designated as IB100 was constructed.

The *E. coli* strain IB103 was constructed by modification of wild-type trp-operon of IB100 strain with trp(L'-'B)E5 (SEQ ID NO: 83), wherein a part of trpL gene and all attenuators are removed by the translation coupling region between trpB and trpA genes (EP2093291 B1), and trpE gene has a mutation such that the Glu39 is substituted by Thr (trpE5) which confers the resistance to high concentration of tryptophan.

The *E. coli* strain AB3257[$P_{tac\text{-}ideal}$-aroG4-(rpID'-attR-cat-attL-trpE')-serA5] (EP2093291 B1), which is a modified strain obtained from the *E. coli* strain AB3257 (CGSC strain #3257), was used as a donor to transfer the mini-Mu: $P_{tac\text{-}ideal}$-aroG4-(rpID'-attR-cat-attL-trpE')-serA5 expression cassette into the strain IB103 by the method of P1-transduction with subsequent marker excision by the method of Red-dependent integration described above. The resulting cassette mini-Mu:$P_{tac\text{-}ideal}$-aroG4-(rpID'-attB-trpE')-serA5 contains a $P_{tac\text{-}ideal}$ promoter ($O_{lac\text{-}ideal}$-$P_{tac}$/$O_{lac}$) (Mashko et al. (2001) Biotekhnologiya (Russian), 5:3-20), mutation in aroG gene (aroG4) (Kikuchi et al. (1997) Appl. Environ. Microbiol., 63(2): 761-762) which confers on 2-dehydro-3-deoxyphosphoheptonate aldolase (DAHP synthase) insensitivity to feedback inhibition by phenylalanine, and mutation in serA gene (serA5) (U.S. Pat. No. 6,180,373 B1) which confers on D-3-phosphoglycerate dehydrogenase insensitivity to feedback inhibition by serine. To optimize expression of serA5 gene, the translation coupling between aroG4 and serA5 genes was provided (EP2093291 B1). Thus, the strain IB105 was constructed.

The *E. coli* strain IB111 was constructed by modifying the IB105 strain with ΔpykA, ΔpykF, and ΔiclR. All deletions were constructed in the chromosome of MG1655 strain (ATCC 47076) by the method of Red-dependent integration described above. According to this procedure, the PCR primers P54 (SEQ ID NO: 84) and P55 (SEQ ID NO: 85) for pykA gene deletion, P56 (SEQ ID NO: 86) and P57 (SEQ ID NO: 87) for pykF gene deletion, and P58 (SEQ ID NO: 88) and P59 (SEQ ID NO: 89) for iclR gene deletion were constructed. The plasmid pMW118-attL-cat-attR was used as a template in PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final elongation for 5 min at 72° C.

Obtained DNA fragments were purified by "Silica Bead DNA Gel Extraction Kit" (Thermo Scientific) and used for electroporation of the *E. coli* strain MG1655 containing the plasmid pKD46. $Cm^R$ recombinants were selected, and the deletions of the pykA, pykF, iclR genes marked with $Cm^R$ gene in the selected mutants were verified by PCR using primers P60 (SEQ ID NO: 90) and P61 (SEQ ID NO: 91), P62 (SEQ ID NO: 92) and P63 (SEQ ID NO: 93), and P64 (SEQ ID NO: 94) and P65 (SEQ ID NO: 95) respectively. Thus, the strains MG1655 ΔpykA:cat, MG1655 ΔpykF:cat, and MG1655 ΔiclR:cat were constructed. These three strains were used as donors for sequential P1-transduction of the pykA, pykF and iclR gene deletions into the strain IB105 with subsequent marker excision. Excision was confirmed by PCR as described above. As a result, the strain IB105 ΔpykA:attB ΔpykF:attB ΔiclR:attB designated as IB111 was constructed.

The *E. coli* strain VD1 (U.S. Pat. No. 7,179,623 B2), which is a modified strain obtained from the *E. coli* strain MG1655, was used as a donor to transfer the mini-Mu:Pscr-scrKYABR expression cassette into the strain IB111 by the method of P1-transduction with subsequent marker excision by the method of Red-dependent integration described above. The cassette contains PTS-dependent sucrose consumption pathway (scr) derived from sucrose transposon Tn2555 (Doroshenko et al. (1988) Mol. Biol. (Mosk.), 22: 645-658). Thus, the strain IB117 was constructed.

To ensure a high level of constitutive expression of an aromatic amino acid exporter gene (yddG), the regulatory region of the $P_{tac5000}$ promoter (Katashkina et al. (2005) Mol. Biol. (Mosk.), 39(5): 823-831), marked with the cat gene, was introduced upstream the yddG gene by the method of Red-dependent integration described above. According to this procedure, the PCR primers P66 (SEQ ID NO: 96), which is homologous to the 5'-part of yddG gene and the $P_{tac5000}$ promoter, and P67 (SEQ ID NO: 97), which is homologous to the region adjacent to the yddG gene and the region adjacent to the cat gene and the $P_{tac5000}$ promoter in the template chromosome were constructed. The chromosome of the strain MG1655 cat-$P_{tac5000}$-lacZ (Katashkina et al. (2005) Mol. Biol. (Mosk.), 39(5): 823-831) was used as a template in PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final step: 5 min at 72° C. The resulting 1792 bp DNA fragment was purified by "Silica Bead DNA Gel Extraction Kit" (Thermo Scientific) and used for electroporation of the strain MG1655 containing the plasmid pKD46. $Cm^R$ recombinants were selected, and the introduction of $P_{tac5000}$ promoter was confirmed by PCR using primers P68 (SEQ ID NO: 98) and P69 (SEQ ID NO: 99). Conditions for PCR were as follows: denaturation for 5 min at 94° C.; profile for 25 cycles: 30 sec at 94° C., 30 sec at 59° C., 90 sec at 72° C.; final elongation for 5 min at 72° C. DNA fragment obtained in the reaction with DNA of the cells of the parent strain MG1655 as a template, was 198 bp in length. DNA fragment obtained in the reaction with DNA of the cells of the strain MG1655 cat-$P_{tac5000}$-yddG as a template, was 1918 bp in length.

The resulting strain MG1655 cat-$P_{tac5000}$-yddG was used as a donor to transfer the cat-$P_{tac5000}$-yddG expression cassette into the strain D3117. The cassette was transferred by the method of P1-transduction. $Cm^R$ recombinants were selected and the introduction of $P_{tac5000}$ promoter was verified by PCR as described above. After that, λ-Int/Xis-mediated excision of $Cm^R$ marker was performed. Excision was confirmed by PCR as described above. DNA fragment obtained in the reaction with DNA of the cells of the parent strain D3117 cat-$P_{tac5000}$-yddG used as a template, was 1918 bp in length. DNA fragment obtained in the reaction with DNA of the cells of the strain IB117 attB-$P_{tac5000}$-yddG used as a template, was 312 bp in length. As a result, the strain IB117 attB-$P_{tac5000}$-yddG designated as IB119 was constructed.

Example 13. Production of L-Tryptophan Using *E. coli* Strains

The *E. coli* strains IB119 and IB119 attB-$P_{tac3000}$-tolC cat-$P_{tac3000}$-yibIH (Example 12) were subjected to the production tests comparing capacity of the fermentative production of L-tryptophan. The strains were plated on L-agar (yeast extract—5 g/L, peptone—10 g/L, NaCl—5 g/L, agar—15 g/L) supplemented with antibiotics if necessary (Cm—30 mg/L, Amp—100 mg/L) and grown at 37° C. overnight.

Cells were inoculated into 3 mL of L-broth medium (tryptone—10 g/L, yeast extract—5 g/L, NaCl—5 g/L) and cultivated for 3 hours at 34° C. at 240 rpm. Then, 0.3 mL of seed culture were inoculated into 3 mL of a fermentation medium in 20×200-mm test tubes and cultivated at 30° C. for 42 hours on a rotary shaker at 240 rpm. The fermentation medium components are listed in Table 7, but should be sterilized in separate groups (A, B, C, D, E, F, G, and H), as shown, to avoid adverse interactions during sterilization.

TABLE 7

Composition of fermentation medium for fermentation of L-tryptophan-producing *E. coli* strains.

| Solutions | Components | Final concentration, g/L |
|---|---|---|
| A | $KH_2PO_4$ | 0.228 |
| | NaCl | 0.146 |
| | $(NH_4)_2SO_4$ | 15.0 |
| | L-Methionine | 0.86 |
| | L-Phenylalanine | 0.1 |
| | L-Tyrosine | 0.1 |
| | Mameno* (as the amount of nitrogen) | 0.05 |
| | $CaCl_2$•$2H_2O$ | 0.004 |
| B | Glucose | 50.0 |
| C | $MgSO_4$•$7H_2O$ | 0.3 |
| D | $FeSO_4$•$7H_2O$ | 0.005 |
| | Sodium citrate | 0.6 |
| E | $Na_2MoO_4$•$2H_2O$ | 0.00015 |
| | $H_3BO_3$ | 0.0025 |
| | $CoCl_2$•$6H_2O$ | 0.0007 |
| | $CuSO_4$•$5H_2O$ | 0.00025 |
| | $MnCl_2$•$4H_2O$ | 0.0016 |
| | $ZnSO_4$•$7H_2O$ | 0.0003 |
| F | Thiamine•HCl | 0.003 |
| G | $CaCO_3$ | 30.0 |
| H | Pyridoxine | 0.03 |

The pH of solution A was adjusted to 7.1 with $NH_4OH$.

*Mameno is the soybean meal hydrolysate (Ajinomoto Co., Inc.).

After cultivation, accumulated L-tryptophan was measured using thin-layer chromatography (TLC). TLC plates (10×15 cm) coated with 0.11 mm layers of Sorbfil silica gel containing non-fluorescent indicator (Sorbpolymer, Krasnodar, Russian Federation) were used. Samples were applied to the plates with the Camag Linomat 5 sample applicator. The Sorbfil plates were developed with a mobile phase consisting of propan-2-ol:ethylacetate:25% aqueous ammonia:water=40:40:7:16 (v/v). A solution of ninhydrin (2%, w/v) in acetone was used as a visualizing reagent. After development, plates were dried and scanned with the Camag TLC Scanner 3 in absorbance mode with detection at 520 nm using winCATS software (version 1.4.2).

The results of twelve independent test tube fermentations (as average values) are shown in Table 8. As one can see from the Table 8, the modified *E. coli* D3119 attB-$P_{tac3000}$- tolC cat-$P_{tac3000}$-yibIH was able to accumulate a higher amount of L-tryptophan as compared with the control IB119 strain.

TABLE 8

Production of L-tryptophan

| Strain | $OD_{600}$ | Trp, g/L |
|---|---|---|
| *E. coli* IB119 (control) | 17.0 | 11.8 |
| *E. coli* IB119 attB-$P_{tac3000}$-tolC cat-$P_{tac3000}$-yibIH | 17.5 | 12.4 |

(n = 12)

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

INDUSTRIAL APPLICABILITY

The method as described herein is useful for the production of L-amino acids by fermentation of a bacterium.

We claim:

1. A method for producing an L-amino acid comprising:

(i) cultivating in a culture medium an L-amino acid-producing bacterium belonging to the family Enterobacteriaceae to produce and accumulate the L-amino acid in the culture medium, cells of the bacterium, or both, and (ii) collecting the L-amino acid from the culture medium, the cells, or both, wherein said bacterium has been modified to overexpress a gene encoding a periplasmic adaptor protein;

wherein said gene is selected from the group consisting of:

(A) yibHI gene;

(B) a gene comprising the nucleotide sequence of SEQ ID NO: 1;

(C) a gene comprising a nucleotide sequence that is able to hybridize under stringent conditions with a nucleotide sequence complementary to the sequence of SEQ ID NO: 1; wherein the stringent conditions are washing 2 times with a salt solution of 0.1×SSC, 0.1% SDS at 60° C.; and wherein if the gene is overexpressed in the bacterium, the amount of the L-amino acid produced by the bacterium is increased as compared to that in a bacterium not modified to overexpress a gene encoding a periplasmic adaptor protein;

(D) a gene having an identity of not less than 90% with respect to the entire nucleotide sequence of SEQ ID NO: 1; and wherein if the gene is overexpressed in the bacterium, the amount of the L-amino acid produced by the bacterium is increased as compared to that in a bacterium not modified to overexpress a gene encoding a periplasmic adaptor protein;

(E) a gene comprising the variant nucleotide sequence of SEQ ID NO: 1, wherein the variant nucleotide sequence is due to the degeneracy of the genetic code;

(F) a gene encoding a protein comprising the amino acid sequence of SEQ ID NO: 2; and wherein if the gene is overexpressed in the bacterium, the amount of the L-amino acid produced by the bacterium is increased as compared to that in a bacterium not modified to overexpress a gene encoding a periplasmic adaptor protein;

(G) a gene encoding a protein comprising the amino acid sequence of SEQ ID NO: 2, but wherein said amino acid sequence includes substitution, deletion, insertion, and/or addition of one to ten amino acid residues; and wherein if the gene is overexpressed in the bacterium, the amount of the L-amino acid produced by the bacterium is increased as compared to that in a bacterium not modified to overexpress a gene encoding a periplasmic adaptor protein; and (H) a gene encoding a protein comprising the amino acid sequence having an identity of not less than 90% with respect to the entire amino acid sequence SEQ ID NO: 2; and wherein if the gene is overexpressed in the bacterium, the amount of the L-amino acid produced by the bacterium is increased as compared to that in a bacterium not modified to overexpress a gene encoding a periplasmic adaptor protein.

2. The method according to claim 1, wherein said gene is overexpressed by increasing the copy number of the gene, by modifying an expression regulatory region of the gene, or both; so that the expression of said gene is increased as compared with a bacterium not modified to overexpress a gene encoding a periplasmic adaptor protein.

3. The method according to claim 1, wherein said bacterium belongs to the genus *Escherichia* or *Pantoea*.

4. The method according to claim 3, wherein said bacterium is *Escherichia coli* or *Pantoea ananatis*.

5. The method according to claim 1, wherein said L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

6. The method according to claim 1, wherein said bacterium has been modified further to overexpress a gene encoding an inner membrane protein, a gene encoding an outer membrane protein, or both.

7. The method according to claim 6, wherein said gene encoding an inner membrane protein is selected from the group consisting of rhtA, rhtB, rhtC, leuE, eamA, argO, eamB, ygaZH, yddG, cydDC, yjeH, alaE, yahN, and lysO; and wherein said gene encoding an outer membrane protein is selected from the group consisting of mdtP, tolC, and mdtQ.

8. The method according to claim 7, wherein said gene encoding an inner membrane protein is selected from the group consisting of leuE and yddG, and said gene encoding an outer membrane protein is tolC.

9. The method according to claim 1, wherein said bacterium has been modified further to overexpress a yibI gene.

10. The method according to claim 5, wherein said L-amino acid is selected from the group consisting of L-histidine, L-cysteine, L-valine, and L-tryptophan.

11. The method according to claim 10, wherein said L-amino acid is selected from the group consisting of L-histidine and L-tryptophan.

* * * * *

SEQUENCE LISTING

```
<160> NUMBER OF SEQ ID NOS: 99

<210> SEQ ID NO 1
<211> LENGTH: 1137
<212> TYPE: DNA
<213> ORGANISM: Escherichia coli

<400> SEQUENCE: 1

atggatctat tgattgtttt aacttacgtg gcgctggcgt gggcggtctt taaaatcttc      60

cgcattccgg taaatcagtg gacgctggcg acggcggcgc tgggaggcgt gtttctggtg     120

agtggtttga ttttgttgat gaactacaac cacccttaca cttttaccgc gcaaaaggca     180

gtgatagcga tccctatcac gccacaggtg acgggaattg ttactgaagt cactgacaag     240

aataatcagc ttattcaaaa gggcgaggtg ctttttaagc tcgacccggt tcgttaccag     300

gcgcgagttg acagacttca ggctgacctg atgacggcga cgcataatat aaagacgctg     360

cgtgcgcagc tcactgaagc gcaggccaac accacccagg tttcagcgga gcgcgaccgt     420

ctgtttaaaa attatcaacg ttacttgaaa ggcagccagg cggcggtgaa tccgttctcg     480

gaacgtgaca tcgacgatgc gcggcaaaat ttcctcgcgc aggatgcgct ggtgaaaggc     540

tcggtggcgg agcaggcgca gatccagagc cagctcgaca gtatggttaa cggcgagcaa     600

tcgcagattg tgagcttaag agcgcaactt actgaagcaa aatataacct tgagcagact     660

gtcattcgcg cgccgagcaa tggctacgtt actcaggtac tgatccgccc aggtacatac     720

gcagctgcct tgccgctgcg tccggtgatg gtcttcatcc ccgagcaaaa acggcaaatt     780

gtcgcccaat ttcggcaaaa ctcgctgtta cgtctgaaac ctggcgatga tgcggaagtg     840

gtgtttaacg cgctacctgg gcaggtgttt cacggcaaac tgactagtat tttacctgtc     900

gtgccaggcg gttcttatca ggcgcagggg gtattgcaat cattaacggt cgtgcccggc     960

acggacggtg tgctgggaac cattgaactg gaccctaacg atgatatcga tgccttaccc    1020

gacggcatct acgcccaggt ggcggtttac tccgaccatt tcagccatgt ttcggtgatg    1080

cggaaagtgc tgctaagaat gaccagctgg atgcattatc tttatttgga tcattga       1137


<210> SEQ ID NO 2
<211> LENGTH: 378
<212> TYPE: PRT
<213> ORGANISM: Escherichia coli

<400> SEQUENCE: 2

Met Asp Leu Leu Ile Val Leu Thr Tyr Val Ala Leu Ala Trp Ala Val
1               5                   10                  15

Phe Lys Ile Phe Arg Ile Pro Val Asn Gln Trp Thr Leu Ala Thr Ala
            20                  25                  30
```

```
Ala Leu Gly Gly Val Phe Leu Val Ser Gly Leu Ile Leu Leu Met Asn
        35                  40                  45

Tyr Asn His Pro Tyr Thr Phe Thr Ala Gln Lys Ala Val Ile Ala Ile
    50                  55                  60

Pro Ile Thr Pro Gln Val Thr Gly Ile Val Thr Glu Val Thr Asp Lys
65                  70                  75                  80

Asn Asn Gln Leu Ile Gln Lys Gly Glu Val Leu Phe Lys Leu Asp Pro
                85                  90                  95

Val Arg Tyr Gln Ala Arg Val Asp Arg Leu Gln Ala Asp Leu Met Thr
            100                 105                 110

Ala Thr His Asn Ile Lys Thr Leu Arg Ala Gln Leu Thr Glu Ala Gln
        115                 120                 125

Ala Asn Thr Thr Gln Val Ser Ala Glu Arg Asp Arg Leu Phe Lys Asn
    130                 135                 140

Tyr Gln Arg Tyr Leu Lys Gly Ser Gln Ala Ala Val Asn Pro Phe Ser
145                 150                 155                 160

Glu Arg Asp Ile Asp Asp Ala Arg Gln Asn Phe Leu Ala Gln Asp Ala
                165                 170                 175

Leu Val Lys Gly Ser Val Ala Glu Gln Ala Gln Ile Gln Ser Gln Leu
            180                 185                 190

Asp Ser Met Val Asn Gly Glu Gln Ser Gln Ile Val Ser Leu Arg Ala
        195                 200                 205

Gln Leu Thr Glu Ala Lys Tyr Asn Leu Glu Gln Thr Val Ile Arg Ala
    210                 215                 220

Pro Ser Asn Gly Tyr Val Thr Gln Val Leu Ile Arg Pro Gly Thr Tyr
225                 230                 235                 240

Ala Ala Ala Leu Pro Leu Arg Pro Val Met Val Phe Ile Pro Glu Gln
                245                 250                 255

Lys Arg Gln Ile Val Ala Gln Phe Arg Gln Asn Ser Leu Leu Arg Leu
            260                 265                 270

Lys Pro Gly Asp Asp Ala Glu Val Val Phe Asn Ala Leu Pro Gly Gln
        275                 280                 285

Val Phe His Gly Lys Leu Thr Ser Ile Leu Pro Val Val Pro Gly Gly
    290                 295                 300

Ser Tyr Gln Ala Gln Gly Val Leu Gln Ser Leu Thr Val Val Pro Gly
305                 310                 315                 320

Thr Asp Gly Val Leu Gly Thr Ile Glu Leu Asp Pro Asn Asp Asp Ile
                325                 330                 335

Asp Ala Leu Pro Asp Gly Ile Tyr Ala Gln Val Ala Val Tyr Ser Asp
            340                 345                 350

His Phe Ser His Val Ser Val Met Arg Lys Val Leu Leu Arg Met Thr
        355                 360                 365

Ser Trp Met His Tyr Leu Tyr Leu Asp His
    370                 375
```

<210> SEQ ID NO 3
<211> LENGTH: 1194
<212> TYPE: DNA
<213> ORGANISM: Escherichia coli

<400> SEQUENCE: 3

```
atgaacaaaa acagagggtt tacgcctctg gcggtcgttc tgatgctctc aggcagctta      60

gccctaacag gatgtgacga caaacaggcc caacaaggtg gccagcagat gcccgccgtt     120

ggcgtagtaa cagtcaaaac tgaacctctg cagatcacaa ccgagcttcc gggtcgcacc     180
```

```
agtgcctacc ggatcgcaga agttcgtcct caagttagcg ggattatcct gaagcgtaat    240

ttcaaagaag gtagcgacat cgaagcaggt gtctctctct atcagattga tcctgcgacc    300

tatcaggcga catacgacag tgcgaaaggt gatctggcga aagcccaggc tgcagccaat    360

atcgcgcaat tgacggtgaa tcgttatcag aaactgctcg gtactcagta catcagtaag    420

caagagtacg atcaggctct ggctgatgcg caacaggcga atgctgcggt aactgcggcg    480

aaagctgccg ttgaaactgc gcggatcaat ctggcttaca ccaaagtcac ctctccgatt    540

agcggtcgca ttggtaagtc gaacgtgacg gaaggcgcat tggtacagaa cggtcaggcg    600

actgcgctgg caaccgtgca gcaacttgat ccgatctacg ttgatgtgac ccagtccagc    660

aacgacttcc tgcgcctgaa acaggaactg gcgaatggca cgctgaaaca agagaacggc    720

aaagccaaag tgtcactgat caccagtgac ggcattaagt tcccgcagga cggtacgctg    780

gaattctctg acgttaccgt tgatcagacc actgggtcta tcaccctacg cgctatcttc    840

ccgaacccgg atcacactct gctgccgggt atgttcgtgc gcgcacgtct ggaagaaggg    900

cttaatccaa acgctatttt agtcccgcaa cagggcgtaa cccgtacgcc gcgtggcgat    960

gccaccgtac tggtagttgg cgcggatgac aaagtggaaa cccgtccgat cgttgcaagc   1020

caggctattg gcgataagtg gctggtgaca gaaggtctga aagcaggcga tcgcgtagta   1080

ataagtgggc tgcagaaagt gcgtcctggt gtccaggtaa aagcacaaga agttaccgct   1140

gataataacc agcaagccgc aagcggtgct cagcctgaac agtccaagtc ttaa         1194


<210> SEQ ID NO 4
<211> LENGTH: 397
<212> TYPE: PRT
<213> ORGANISM: Escherichia coli

<400> SEQUENCE: 4

Met Asn Lys Asn Arg Gly Phe Thr Pro Leu Ala Val Val Leu Met Leu
1               5                   10                  15

Ser Gly Ser Leu Ala Leu Thr Gly Cys Asp Asp Lys Gln Ala Gln Gln
            20                  25                  30

Gly Gly Gln Gln Met Pro Ala Val Gly Val Val Thr Val Lys Thr Glu
        35                  40                  45

Pro Leu Gln Ile Thr Thr Glu Leu Pro Gly Arg Thr Ser Ala Tyr Arg
    50                  55                  60

Ile Ala Glu Val Arg Pro Gln Val Ser Gly Ile Ile Leu Lys Arg Asn
65                  70                  75                  80

Phe Lys Glu Gly Ser Asp Ile Glu Ala Gly Val Ser Leu Tyr Gln Ile
                85                  90                  95

Asp Pro Ala Thr Tyr Gln Ala Thr Tyr Asp Ser Ala Lys Gly Asp Leu
            100                 105                 110

Ala Lys Ala Gln Ala Ala Ala Asn Ile Ala Gln Leu Thr Val Asn Arg
        115                 120                 125

Tyr Gln Lys Leu Leu Gly Thr Gln Tyr Ile Ser Lys Gln Glu Tyr Asp
    130                 135                 140

Gln Ala Leu Ala Asp Ala Gln Gln Ala Asn Ala Ala Val Thr Ala Ala
145                 150                 155                 160

Lys Ala Ala Val Glu Thr Ala Arg Ile Asn Leu Ala Tyr Thr Lys Val
                165                 170                 175

Thr Ser Pro Ile Ser Gly Arg Ile Gly Lys Ser Asn Val Thr Glu Gly
            180                 185                 190
```

```
Ala Leu Val Gln Asn Gly Gln Ala Thr Ala Leu Ala Thr Val Gln Gln
        195                 200                 205

Leu Asp Pro Ile Tyr Val Asp Val Thr Gln Ser Ser Asn Asp Phe Leu
    210                 215                 220

Arg Leu Lys Gln Glu Leu Ala Asn Gly Thr Leu Lys Gln Glu Asn Gly
225                 230                 235                 240

Lys Ala Lys Val Ser Leu Ile Thr Ser Asp Gly Ile Lys Phe Pro Gln
                245                 250                 255

Asp Gly Thr Leu Glu Phe Ser Asp Val Thr Val Asp Gln Thr Thr Gly
            260                 265                 270

Ser Ile Thr Leu Arg Ala Ile Phe Pro Asn Pro Asp His Thr Leu Leu
        275                 280                 285

Pro Gly Met Phe Val Arg Ala Arg Leu Glu Glu Gly Leu Asn Pro Asn
    290                 295                 300

Ala Ile Leu Val Pro Gln Gln Gly Val Thr Arg Thr Pro Arg Gly Asp
305                 310                 315                 320

Ala Thr Val Leu Val Val Gly Ala Asp Asp Lys Val Glu Thr Arg Pro
                325                 330                 335

Ile Val Ala Ser Gln Ala Ile Gly Asp Lys Trp Leu Val Thr Glu Gly
            340                 345                 350

Leu Lys Ala Gly Asp Arg Val Val Ile Ser Gly Leu Gln Lys Val Arg
        355                 360                 365

Pro Gly Val Gln Val Lys Ala Gln Glu Val Thr Ala Asp Asn Asn Gln
    370                 375                 380

Gln Ala Ala Ser Gly Ala Gln Pro Glu Gln Ser Lys Ser
385                 390                 395


<210> SEQ ID NO 5
<211> LENGTH: 1125
<212> TYPE: DNA
<213> ORGANISM: Aquifex aeolicus

<400> SEQUENCE: 5

atgaaaaagt acataggcgt ttttacggtt gtggctttaa ttgtgggctt tgggatttac      60

gcctttttct tcataaaaca cagaattgag tatgccataa caaacgcagt cttcgttaag     120

gcggacgagc tttcttatct gtccttcaga gtaagcggaa aggttattga agtttacaaa     180

gacctcggag attacgtaaa aaggggggaa gcccttgcaa aactggatcc gacttattac     240

gaacttgaga aaagaacact tgagaaaaaa atgagcgccc tccttgaaaa gaaaaaagcc     300

cttgagataa aaattcagaa gctggaaaag ggacttcata taagcctgag tgctaaaaaa     360

ctaaaagttg agagtttaaa aaagaaaagg gaagccctac gggaaaaact ccttcaagtg     420

gaagagaaaa taaaactcgt taaacttgac tgggaacgct acaaatccct cttccaaaaa     480

ggacttatcc cgagaaggaa gtttgaagaa gtagacacga acctgaaagt tttacttcac     540

gagagggaat accttgaaaa gagcatacag gaaattaata cggagataaa aagggcaaag     600

aaaggcattg aaaatgcaag gaatgagttt aaaacaatag aggaactaaa aaaggaactc     660

tcctcccttg aggaagaaat aaagagcctg aaagagagga taaaaaccgc agagcagaag     720

ataaaagaca cggttttgat tgcacctttt gacggagtag ttgcaaagag gttcataagc     780

aggggagacg ttgttagggc gggacagccg gcctttgccc ttgtaaaccc tgaaagcttt     840

tacgtagagg ttttactcga agagacgaaa ctcaaaggcg tgaaggtggg aaataaagct     900

tacgtgagac ttgacgctta ccctgacatc ctttttgaag gagttgttga ggagatttcc     960
```

```
cccgcttccg cagcgacttt tgccttagtc cccagagatg tatccgcggg agaattcaca   1020

aaagttgttc agaggatacc cgtaaagata aagattacga aaggggattt aagccttctg   1080

agagtgggaa tgggcggtga ggttgagata aggagaacga gatga                   1125


<210> SEQ ID NO 6
<211> LENGTH: 374
<212> TYPE: PRT
<213> ORGANISM: Aquifex aeolicus

<400> SEQUENCE: 6

Met Lys Lys Tyr Ile Gly Val Phe Thr Val Val Ala Leu Ile Val Gly
1               5                   10                  15

Phe Gly Ile Tyr Ala Phe Phe Phe Ile Lys His Arg Ile Glu Tyr Ala
            20                  25                  30

Ile Thr Asn Ala Val Phe Val Lys Ala Asp Glu Leu Ser Tyr Leu Ser
        35                  40                  45

Phe Arg Val Ser Gly Lys Val Ile Glu Val Tyr Lys Asp Leu Gly Asp
    50                  55                  60

Tyr Val Lys Arg Gly Glu Ala Leu Ala Lys Leu Asp Pro Thr Tyr Tyr
65                  70                  75                  80

Glu Leu Glu Lys Arg Thr Leu Glu Lys Lys Met Ser Ala Leu Leu Glu
                85                  90                  95

Lys Lys Lys Ala Leu Glu Ile Lys Ile Gln Lys Leu Glu Lys Gly Leu
            100                 105                 110

His Ile Ser Leu Ser Ala Lys Lys Leu Lys Val Glu Ser Leu Lys Lys
        115                 120                 125

Lys Arg Glu Ala Leu Arg Glu Lys Leu Leu Gln Val Glu Glu Lys Ile
    130                 135                 140

Lys Leu Val Lys Leu Asp Trp Glu Arg Tyr Lys Ser Leu Phe Gln Lys
145                 150                 155                 160

Gly Leu Ile Pro Arg Arg Lys Phe Glu Glu Val Asp Thr Asn Leu Lys
                165                 170                 175

Val Leu Leu His Glu Arg Glu Tyr Leu Glu Lys Ser Ile Gln Glu Ile
            180                 185                 190

Asn Thr Glu Ile Lys Arg Ala Lys Lys Gly Ile Glu Asn Ala Arg Asn
        195                 200                 205

Glu Phe Lys Thr Ile Glu Glu Leu Lys Lys Glu Leu Ser Ser Leu Glu
    210                 215                 220

Glu Glu Ile Lys Ser Leu Lys Glu Arg Ile Lys Thr Ala Glu Gln Lys
225                 230                 235                 240

Ile Lys Asp Thr Val Leu Ile Ala Pro Phe Asp Gly Val Val Ala Lys
                245                 250                 255

Arg Phe Ile Ser Arg Gly Asp Val Val Arg Ala Gly Gln Pro Ala Phe
            260                 265                 270

Ala Leu Val Asn Pro Glu Ser Phe Tyr Val Glu Val Leu Leu Glu Glu
        275                 280                 285

Thr Lys Leu Lys Gly Val Lys Val Gly Asn Lys Ala Tyr Val Arg Leu
    290                 295                 300

Asp Ala Tyr Pro Asp Ile Leu Phe Glu Gly Val Val Glu Glu Ile Ser
305                 310                 315                 320

Pro Ala Ser Ala Ala Thr Phe Ala Leu Val Pro Arg Asp Val Ser Ala
                325                 330                 335

Gly Glu Phe Thr Lys Val Val Gln Arg Ile Pro Val Lys Ile Lys Ile
            340                 345                 350
```

```
Thr Lys Gly Asp Leu Ser Leu Leu Arg Val Gly Met Gly Gly Glu Val
        355                 360                 365

Glu Ile Arg Arg Thr Arg
    370


<210> SEQ ID NO 7
<211> LENGTH: 1158
<212> TYPE: DNA
<213> ORGANISM: Cupriavidus metallidurans

<400> SEQUENCE: 7

atgaaaaaca agccagcctt tcccgggcgc gttgtctact ggcttgccgc ggcggtcata     60

ctgggtctcg gcggtgctgg tgtctggacg atgcgcgcca aggccgaaca gaagcgcgcg    120

gacccgcccg tcgccctgcg tcatgaaggc gagcgcctgg tagtcccggc cgagtcgcca    180

ttgcgccgca ccttggccgt cgcgcccgcc acgcgcgaaa ccgtggctgc accgttcaat    240

ctgccggcca tgatcgaagc cgatccggcc aagctcgtga aagtgctgcc gccgctggcc    300

ggccgtatcg tcagcctgaa caagcagctt ggcgacgagg tcaaggctgg cgacgtgctg    360

ttcacgatcg attcggccga tctcgcgcag gccaacagcg acgccgccaa ggcccgcgcg    420

gccatgacaa tggcacgccg caacctggat cgtcagcggg aactggacaa gtcagagatc    480

gccgcaaagc gcgacttcga gcaggcccag agcgactatg accaggccgc cagcgaatcc    540

cagcgcgccg atgcgcgtct ggcgcaactt ggcgccaagg gtggcggcac gttgcaggcg    600

ggcggcggcc acatcctggc cgtgcgatcg ccgatcaacg ggcgcgtggt cgatctcaat    660

gccgcgaccg gcgcgtattg gaacgacacc acggcctccc tgatgaccgt tgccgatctc    720

tcgcacgtgt ttgtcacggc caacgcgcag gaaaaggatc tgggccacgt gtatgtcggc    780

cagtcggcca ccgtcaagtt cgacgcctat gacgatccgc aaccgggcaa ggtgcgctat    840

gtcgggcaga tccttgatgc ggacacgcgc acgaccaagg tgcgcatggt gttcgacaac    900

cccgacggac ggctccgtcc cggcatgttc gcgcaggcta ccttcctgtc ccagccgcat    960

gaaggcatcg tcgtgccgat gtcggccatc gtgcagagcg gcttctacac ccgcgcattc   1020

gtcgaagtgg cgccgtggca gttcgagccc cgtgtgatca agctcggcgc gcaaatcggc   1080

gaccgtatgg aagtgaagtc gggcctgtcc gcgggagacc gcgtggtggt gaaggaaggg   1140

gtgctgctga atgattga                                                 1158


<210> SEQ ID NO 8
<211> LENGTH: 385
<212> TYPE: PRT
<213> ORGANISM: Cupriavidus metallidurans

<400> SEQUENCE: 8

Met Lys Asn Lys Pro Ala Phe Pro Gly Arg Val Val Tyr Trp Leu Ala
1               5                   10                  15

Ala Ala Val Ile Leu Gly Leu Gly Gly Ala Gly Val Trp Thr Met Arg
            20                  25                  30

Ala Lys Ala Glu Gln Lys Arg Ala Asp Pro Pro Val Ala Leu Arg His
        35                  40                  45

Glu Gly Glu Arg Leu Val Val Pro Ala Glu Ser Pro Leu Arg Arg Thr
    50                  55                  60

Leu Ala Val Ala Pro Ala Thr Arg Glu Thr Val Ala Ala Pro Phe Asn
65                  70                  75                  80

Leu Pro Ala Met Ile Glu Ala Asp Pro Ala Lys Leu Val Lys Val Leu
```

```
                85                  90                  95

Pro Pro Leu Ala Gly Arg Ile Val Ser Leu Asn Lys Gln Leu Gly Asp
            100                 105                 110

Glu Val Lys Ala Gly Asp Val Leu Phe Thr Ile Asp Ser Ala Asp Leu
        115                 120                 125

Ala Gln Ala Asn Ser Asp Ala Ala Lys Ala Arg Ala Ala Met Thr Met
    130                 135                 140

Ala Arg Arg Asn Leu Asp Arg Gln Arg Glu Leu Asp Lys Ser Glu Ile
145                 150                 155                 160

Ala Ala Lys Arg Asp Phe Glu Gln Ala Gln Ser Asp Tyr Asp Gln Ala
                165                 170                 175

Ala Ser Glu Ser Gln Arg Ala Asp Ala Arg Leu Ala Gln Leu Gly Ala
            180                 185                 190

Lys Gly Gly Gly Thr Leu Gln Ala Gly Gly Gly His Ile Leu Ala Val
        195                 200                 205

Arg Ser Pro Ile Asn Gly Arg Val Val Asp Leu Asn Ala Ala Thr Gly
    210                 215                 220

Ala Tyr Trp Asn Asp Thr Thr Ala Ser Leu Met Thr Val Ala Asp Leu
225                 230                 235                 240

Ser His Val Phe Val Thr Ala Asn Ala Gln Glu Lys Asp Leu Gly His
                245                 250                 255

Val Tyr Val Gly Gln Ser Ala Thr Val Lys Phe Asp Ala Tyr Asp Asp
            260                 265                 270

Pro Gln Pro Gly Lys Val Arg Tyr Val Gly Gln Ile Leu Asp Ala Asp
        275                 280                 285

Thr Arg Thr Thr Lys Val Arg Met Val Phe Asp Asn Pro Asp Gly Arg
    290                 295                 300

Leu Arg Pro Gly Met Phe Ala Gln Ala Thr Phe Leu Ser Gln Pro His
305                 310                 315                 320

Glu Gly Ile Val Val Pro Met Ser Ala Ile Val Gln Ser Gly Phe Tyr
                325                 330                 335

Thr Arg Ala Phe Val Glu Val Ala Pro Trp Gln Phe Glu Pro Arg Val
            340                 345                 350

Ile Lys Leu Gly Ala Gln Ile Gly Asp Arg Met Glu Val Lys Ser Gly
        355                 360                 365

Leu Ser Ala Gly Asp Arg Val Val Val Lys Glu Gly Val Leu Leu Asn
    370                 375                 380

Asp
385


<210> SEQ ID NO 9
<211> LENGTH: 1164
<212> TYPE: DNA
<213> ORGANISM: Escherichia coli

<400> SEQUENCE: 9

gtggaacaga ttaattcaaa taaaaaacat tctaacagaa gaaaatactt ttctttattg      60

gcggtagttt tatttattgc gttttcaggt gcctatgcct attggtcaat ggaattagaa     120

gacatgatta gtacagatga cgcctatgtc acggggaatg cagatccaat ttctgcacaa     180

gtctcaggta gtgtcactgt cgttaatcat aaagatacga actacgttcg acaaggtgac     240

attttagttt cactggataa aactgatgcc actatcgcac tcaataaagc taaaaataat     300

ctggcaaata ttgttcggca aacgaataaa ctatacttac aggataaaca atacagtgcc     360
```

```
gaagtcgctt cagcacgtat tcagtatcaa caatctttag aagattataa ccgtcgagtg    420

ccgttagcga agcagggggt tatttcaaaa gaaacgctgg agcataccaa agatacgtta    480

ataagtagca aagcggcatt gaatgccgct atccaggctt ataaagcgaa taaagcttta    540

gtaatgaaca caccattaaa ccgtcagcca caagtcgttg aagcggcgga tgcaactaaa    600

gaagcctggt tggcgcttaa acgtacggat attaagagtc cggttaccgg ctatattgcc    660

cagagaagtg ttcaggtcgg cgaaacagtg agccccggac aatcgttaat ggctgtcgta    720

ccggcacgtc aaatgtgggt taatgccaac tttaaagaaa cacaactcac ggatgtacgg    780

attggtcaat cggtcaatat tatcagcgat ctttatggtg aaaatgttgt gtttcatggt    840

cgggtgacag ggatcaatat gggaaccggc aatgcgttct ccttattacc tgcacaaaat    900

gcgacaggga actggatcaa aatcgttcag cgtgtaccgg ttgaagtttc tcttgatcca    960

aaagaactca tggaacaccc cttgcgtatt ggtttatcga tgacagcaac tattgatacg   1020

aagaacgaag acattgccga gatgcctgag ctggcttcaa ccgtgacctc catgccggct   1080

tataccagta aggctttagt tatcgatacc agtccgatag aaaaagaaat tagcaacatt   1140

atttcgcata atggacaact ttaa                                          1164


<210> SEQ ID NO 10
<211> LENGTH: 387
<212> TYPE: PRT
<213> ORGANISM: Escherichia coli

<400> SEQUENCE: 10

Met Glu Gln Ile Asn Ser Asn Lys Lys His Ser Asn Arg Arg Lys Tyr
1               5                   10                  15

Phe Ser Leu Leu Ala Val Val Leu Phe Ile Ala Phe Ser Gly Ala Tyr
            20                  25                  30

Ala Tyr Trp Ser Met Glu Leu Glu Asp Met Ile Ser Thr Asp Asp Ala
        35                  40                  45

Tyr Val Thr Gly Asn Ala Asp Pro Ile Ser Ala Gln Val Ser Gly Ser
    50                  55                  60

Val Thr Val Val Asn His Lys Asp Thr Asn Tyr Val Arg Gln Gly Asp
65                  70                  75                  80

Ile Leu Val Ser Leu Asp Lys Thr Asp Ala Thr Ile Ala Leu Asn Lys
                85                  90                  95

Ala Lys Asn Asn Leu Ala Asn Ile Val Arg Gln Thr Asn Lys Leu Tyr
            100                 105                 110

Leu Gln Asp Lys Gln Tyr Ser Ala Glu Val Ala Ser Ala Arg Ile Gln
        115                 120                 125

Tyr Gln Gln Ser Leu Glu Asp Tyr Asn Arg Arg Val Pro Leu Ala Lys
    130                 135                 140

Gln Gly Val Ile Ser Lys Glu Thr Leu Glu His Thr Lys Asp Thr Leu
145                 150                 155                 160

Ile Ser Ser Lys Ala Ala Leu Asn Ala Ala Ile Gln Ala Tyr Lys Ala
                165                 170                 175

Asn Lys Ala Leu Val Met Asn Thr Pro Leu Asn Arg Gln Pro Gln Val
            180                 185                 190

Val Glu Ala Ala Asp Ala Thr Lys Glu Ala Trp Leu Ala Leu Lys Arg
        195                 200                 205

Thr Asp Ile Lys Ser Pro Val Thr Gly Tyr Ile Ala Gln Arg Ser Val
    210                 215                 220

Gln Val Gly Glu Thr Val Ser Pro Gly Gln Ser Leu Met Ala Val Val
```

```
225                 230                 235                 240

Pro Ala Arg Gln Met Trp Val Asn Ala Asn Phe Lys Glu Thr Gln Leu
                245                 250                 255

Thr Asp Val Arg Ile Gly Gln Ser Val Asn Ile Ile Ser Asp Leu Tyr
            260                 265                 270

Gly Glu Asn Val Val Phe His Gly Arg Val Thr Gly Ile Asn Met Gly
        275                 280                 285

Thr Gly Asn Ala Phe Ser Leu Leu Pro Ala Gln Asn Ala Thr Gly Asn
    290                 295                 300

Trp Ile Lys Ile Val Gln Arg Val Pro Val Glu Val Ser Leu Asp Pro
305                 310                 315                 320

Lys Glu Leu Met Glu His Pro Leu Arg Ile Gly Leu Ser Met Thr Ala
                325                 330                 335

Thr Ile Asp Thr Lys Asn Glu Asp Ile Ala Glu Met Pro Glu Leu Ala
            340                 345                 350

Ser Thr Val Thr Ser Met Pro Ala Tyr Thr Ser Lys Ala Leu Val Ile
        355                 360                 365

Asp Thr Ser Pro Ile Glu Lys Glu Ile Ser Asn Ile Ile Ser His Asn
    370                 375                 380

Gly Gln Leu
385


<210> SEQ ID NO 11
<211> LENGTH: 1248
<212> TYPE: DNA
<213> ORGANISM: Escherichia coli

<400> SEQUENCE: 11

atgaaaggta gttataaatc ccgttgggta atcgtaatcg tggtggttat cgccgccatc     60

gccgcattct ggttctggca aggccgcaat gactcccgga gtgcagcccc aggggcgacg    120

aaacaagcgc agcaatcgcc agcgggtggt cgacgtggta tgcgttccgg cccattagcc    180

ccggttcagg cggcgaccgc cgtagaacag gcagttccgc gttacctcac cgggcttggc    240

accattaccg ccgctaatac cgttacggtg cgcagccgcg tggacggcca actgatagcg    300

ttacatttcc aggaaggcca gcaggtcaaa gcaggcgatt tactggcaga aattgacccc    360

agccagttca aagttgcatt agcacaagcc cagggccaac tggcaaaaga taaagccacg    420

cttgccaacg cccgccgtga cctggcgcgt tatcaacaac tggcaaaaac caatctcgtt    480

tcccgccagg agctggatgc ccaacaggcg ctggtcagtg aaaccgaagg caccattaag    540

gctgatgaag caagcgttgc cagcgcgcag ctgcaactcg actggagccg gattaccgca    600

ccagtcgatg gtcgcgttgg tctcaagcag gttgatgttg gtaaccaaat ctccagtggt    660

gataccaccg ggatcgtggt gatcacccag acgcatccta tcgatttagt ctttaccctg    720

ccggaaagcg atatcgctac cgtagtgcag gcgcagaaag ccggaaaacc gctggtggta    780

gaagcctggg atcgcaccaa ctcgaagaaa ttaagtgaag gcacgctgtt aagtctagat    840

aaccaaatcg atgccactac cggtacgatt aaagtgaaag cacgctttaa taatcaggat    900

gatgcgctgt ttcccaatca gtttgttaac gcgcgcatgt tagtcgacac cgaacaaaac    960

gccgtagtga tcccaacagc cgccctgcaa atgggcaatg aaggccattt tgtctgggtg   1020

ctgaatagcg aaaacaaggt cagcaaacat ctggtgacgc cgggcattca ggacagtcag   1080

aaagtggtga tccgtgcagg tatttctgcg ggcgatcgcg tggtgacaga cggcattgat   1140

cgcctgaccg aaggggcgaa agtggaagtg gtggaagccc agagcgccac tactccggaa   1200
```

gagaaagcca ccagccgcga atacgcgaaa aaaggagcac gctcctga 1248

<210> SEQ ID NO 12
<211> LENGTH: 415
<212> TYPE: PRT
<213> ORGANISM: Escherichia coli

<400> SEQUENCE: 12

Met Lys Gly Ser Tyr Lys Ser Arg Trp Val Ile Val Ile Val Val Val
1 5 10 15

Ile Ala Ala Ile Ala Ala Phe Trp Phe Trp Gln Gly Arg Asn Asp Ser
20 25 30

Arg Ser Ala Ala Pro Gly Ala Thr Lys Gln Ala Gln Gln Ser Pro Ala
35 40 45

Gly Gly Arg Arg Gly Met Arg Ser Gly Pro Leu Ala Pro Val Gln Ala
50 55 60

Ala Thr Ala Val Glu Gln Ala Val Pro Arg Tyr Leu Thr Gly Leu Gly
65 70 75 80

Thr Ile Thr Ala Ala Asn Thr Val Thr Val Arg Ser Arg Val Asp Gly
85 90 95

Gln Leu Ile Ala Leu His Phe Gln Glu Gly Gln Gln Val Lys Ala Gly
100 105 110

Asp Leu Leu Ala Glu Ile Asp Pro Ser Gln Phe Lys Val Ala Leu Ala
115 120 125

Gln Ala Gln Gly Gln Leu Ala Lys Asp Lys Ala Thr Leu Ala Asn Ala
130 135 140

Arg Arg Asp Leu Ala Arg Tyr Gln Gln Leu Ala Lys Thr Asn Leu Val
145 150 155 160

Ser Arg Gln Glu Leu Asp Ala Gln Gln Ala Leu Val Ser Glu Thr Glu
165 170 175

Gly Thr Ile Lys Ala Asp Glu Ala Ser Val Ala Ser Ala Gln Leu Gln
180 185 190

Leu Asp Trp Ser Arg Ile Thr Ala Pro Val Asp Gly Arg Val Gly Leu
195 200 205

Lys Gln Val Asp Val Gly Asn Gln Ile Ser Ser Gly Asp Thr Thr Gly
210 215 220

Ile Val Val Ile Thr Gln Thr His Pro Ile Asp Leu Val Phe Thr Leu
225 230 235 240

Pro Glu Ser Asp Ile Ala Thr Val Val Gln Ala Gln Lys Ala Gly Lys
245 250 255

Pro Leu Val Val Glu Ala Trp Asp Arg Thr Asn Ser Lys Lys Leu Ser
260 265 270

Glu Gly Thr Leu Leu Ser Leu Asp Asn Gln Ile Asp Ala Thr Thr Gly
275 280 285

Thr Ile Lys Val Lys Ala Arg Phe Asn Asn Gln Asp Asp Ala Leu Phe
290 295 300

Pro Asn Gln Phe Val Asn Ala Arg Met Leu Val Asp Thr Glu Gln Asn
305 310 315 320

Ala Val Val Ile Pro Thr Ala Ala Leu Gln Met Gly Asn Glu Gly His
325 330 335

Phe Val Trp Val Leu Asn Ser Glu Asn Lys Val Ser Lys His Leu Val
340 345 350

Thr Pro Gly Ile Gln Asp Ser Gln Lys Val Val Ile Arg Ala Gly Ile
355 360 365

```
Ser Ala Gly Asp Arg Val Val Thr Asp Gly Ile Asp Arg Leu Thr Glu
    370                 375                 380

Gly Ala Lys Val Glu Val Val Glu Ala Gln Ser Ala Thr Thr Pro Glu
385                 390                 395                 400

Glu Lys Ala Thr Ser Arg Glu Tyr Ala Lys Lys Gly Ala Arg Ser
                405                 410                 415


<210> SEQ ID NO 13
<211> LENGTH: 1152
<212> TYPE: DNA
<213> ORGANISM: Pseudomonas aeruginosa

<400> SEQUENCE: 13

atgcaacgaa cgccagccat gcgtgtactg gttccggccc tgctggtcgc gatttcggcc      60

ctttccgggt gcggaaaaag cgaggcgccg ccgccggcgc aaacgccgga ggtcgggatc     120

gtgaccctgg aagcgcagac ggtgaccctg aataccgagc tgccgggccg gaccaatgcg     180

ttccgcatcg ccgaggtgcg tccccaggtg aacggcatca tcctcaagcg cctgttcaag     240

gaaggcagcg acgtcaaggc cgggcagcag ctctaccaga tcgaccccgc cacctacgag     300

gccgactacc agagcgccca ggccaacctg gcttcgaccc aggaacaggc ccagcgctac     360

aagctgctgg tcgccgacca ggccgtgagc aagcagcagt acgccgacgc caatgccgcc     420

tacctgcagt ccaaggcggc ggtggagcag gcgcggatca acctgcgcta caccaaggtg     480

ctgtcgccga tctccggccg catcggccgt tccgcggtga ccgaaggcgc cctggtgacc     540

aacggccagg ccaacgcgat ggccaccgtg caacagctcg acccgatcta cgtcgacgtc     600

acccagccgt ccaccgccct gctgcgcctg cgccgcgaac tggccagcgg ccagttggag     660

cgcgccggcg acaacgcggc gaaggtctcc ctgaagctgg aggacggtag ccaatacccg     720

ctggaaggtc gcctcgaatt ctccgaggtt tccgtcgacg aaggcaccgg ctcggtcacc     780

atccgcgccg tgttccccaa cccgaacaac gagctgctgc ccggcatgtt cgttcacgcg     840

cagttgcagg aaggcgtcaa gcagaaggcc atcctcgctc cgcagcaagg cgtgacccgc     900

gacctcaagg gccaggctac cgcgctggtg gtgaacgcgc agaacaaggt cgagctgcgg     960

gtgatcaagg ccgaccgggt gatcggcgac aagtggctgg ttaccgaagg cctgaacgcc    1020

ggcgacaaga tcattaccga aggcctgcag ttcgtgcagc cgggtgtcga ggtgaagacc    1080

gtgccggcga agaatgtcgc gtccgcgcag aaggccgacg ccgctccggc gaaaaccgac    1140

agcaagggct ga                                                        1152


<210> SEQ ID NO 14
<211> LENGTH: 383
<212> TYPE: PRT
<213> ORGANISM: Pseudomonas aeruginosa

<400> SEQUENCE: 14

Met Gln Arg Thr Pro Ala Met Arg Val Leu Val Pro Ala Leu Leu Val
1               5                   10                  15

Ala Ile Ser Ala Leu Ser Gly Cys Gly Lys Ser Glu Ala Pro Pro Pro
            20                  25                  30

Ala Gln Thr Pro Glu Val Gly Ile Val Thr Leu Glu Ala Gln Thr Val
        35                  40                  45

Thr Leu Asn Thr Glu Leu Pro Gly Arg Thr Asn Ala Phe Arg Ile Ala
    50                  55                  60

Glu Val Arg Pro Gln Val Asn Gly Ile Ile Leu Lys Arg Leu Phe Lys
```

-continued

```
65                  70                  75                  80

Glu Gly Ser Asp Val Lys Ala Gly Gln Gln Leu Tyr Gln Ile Asp Pro
                85                  90                  95

Ala Thr Tyr Glu Ala Asp Tyr Gln Ser Ala Gln Ala Asn Leu Ala Ser
            100                 105                 110

Thr Gln Glu Gln Ala Gln Arg Tyr Lys Leu Leu Val Ala Asp Gln Ala
        115                 120                 125

Val Ser Lys Gln Gln Tyr Ala Asp Ala Asn Ala Ala Tyr Leu Gln Ser
    130                 135                 140

Lys Ala Ala Val Glu Gln Ala Arg Ile Asn Leu Arg Tyr Thr Lys Val
145                 150                 155                 160

Leu Ser Pro Ile Ser Gly Arg Ile Gly Arg Ser Ala Val Thr Glu Gly
                165                 170                 175

Ala Leu Val Thr Asn Gly Gln Ala Asn Ala Met Ala Thr Val Gln Gln
            180                 185                 190

Leu Asp Pro Ile Tyr Val Asp Val Thr Gln Pro Ser Thr Ala Leu Leu
        195                 200                 205

Arg Leu Arg Arg Glu Leu Ala Ser Gly Gln Leu Glu Arg Ala Gly Asp
    210                 215                 220

Asn Ala Ala Lys Val Ser Leu Lys Leu Glu Asp Gly Ser Gln Tyr Pro
225                 230                 235                 240

Leu Glu Gly Arg Leu Glu Phe Ser Glu Val Ser Val Asp Glu Gly Thr
                245                 250                 255

Gly Ser Val Thr Ile Arg Ala Val Phe Pro Asn Pro Asn Asn Glu Leu
            260                 265                 270

Leu Pro Gly Met Phe Val His Ala Gln Leu Gln Glu Gly Val Lys Gln
        275                 280                 285

Lys Ala Ile Leu Ala Pro Gln Gln Gly Val Thr Arg Asp Leu Lys Gly
    290                 295                 300

Gln Ala Thr Ala Leu Val Val Asn Ala Gln Asn Lys Val Glu Leu Arg
305                 310                 315                 320

Val Ile Lys Ala Asp Arg Val Ile Gly Asp Lys Trp Leu Val Thr Glu
                325                 330                 335

Gly Leu Asn Ala Gly Asp Lys Ile Ile Thr Glu Gly Leu Gln Phe Val
            340                 345                 350

Gln Pro Gly Val Glu Val Lys Thr Val Pro Ala Lys Asn Val Ala Ser
        355                 360                 365

Ala Gln Lys Ala Asp Ala Ala Pro Ala Lys Thr Asp Ser Lys Gly
    370                 375                 380
```

<210> SEQ ID NO 15
<211> LENGTH: 1116
<212> TYPE: DNA
<213> ORGANISM: Escherichia coli

<400> SEQUENCE: 15

```
atgaaaaagc ggaaaaccgt gaagaagcgt tacgttattg cgctggtgat agtcatcgcc     60

ggactgatta cgttatggag aattcttaac gcacccgtgc cgacttatca gacgctgatt    120

gtgcgccccg gtgatttaca gcaaagcgtg ctggcgaccg gaaagctgga cgcgctgcgt    180

aaggttgatg tgggcgcgca ggtcagcggt cagttgaaaa ctctgtcggt ggcgattggc    240

gataaagtaa aaaaagacca gcttttaggg gttattgatc ctgaacaggc tgaaaaccag    300

attaaggagg tcgaagcaac gctgatggag ctacgtgcgc agcggcagca ggcggaagcg    360
```

```
gagctgaaac tggcgcgggt gacgtattcc cgtcagcaac gtctggcaca aacgaaggct    420

gtttcacagc aggatctcga caccgccgcg acggagatgg ctgtgaaaca ggcgcaaatt    480

ggcaccattg acgcgcaaat caagcgcaat caggcttctc tcgatacggc taaaaccaat    540

ctcgattaca ctcgcatcgt tgccccgatg gccggggaag tcacgcaaat caccactctg    600

caaggccaga cggtgattgc cgcacaacaa gcaccgaaca ttctgacgct ggcagatatg    660

agcgccatgc tggtaaaagc gcaggtttct gaagcggatg taatccacct gaagccgggg    720

caaaaagcct ggtttacggt gcttggcgat ccactgacgc gctacgaggg gcaaatcaag    780

gatgtactac cgacgccgga aaaggttaac gacgctattt tctattacgc ccgttttgaa    840

gtccccaacc ccaatggttt gctgcggctg gatatgactg cgcaagtgca tattcagctc    900

accgatgtga aaaatgtgct gacgatccct ctgtcggcgt taggcgatcc ggttggcgat    960

aatcgttata aagtcaaatt gttgcgtaat ggtgaaacac gcgagcgtga agtgacgatt   1020

ggcgcacgta acgataccga tgttgagatt gtcaaagggc ttgaagcggg cgatgaagtg   1080

gtgattggtg aggccaaacc aggagctgca caatga                             1116
```

<210> SEQ ID NO 16
<211> LENGTH: 371
<212> TYPE: PRT
<213> ORGANISM: Escherichia coli

<400> SEQUENCE: 16

```
Met Lys Lys Arg Lys Thr Val Lys Lys Arg Tyr Val Ile Ala Leu Val
1               5                   10                  15

Ile Val Ile Ala Gly Leu Ile Thr Leu Trp Arg Ile Leu Asn Ala Pro
            20                  25                  30

Val Pro Thr Tyr Gln Thr Leu Ile Val Arg Pro Gly Asp Leu Gln Gln
        35                  40                  45

Ser Val Leu Ala Thr Gly Lys Leu Asp Ala Leu Arg Lys Val Asp Val
    50                  55                  60

Gly Ala Gln Val Ser Gly Gln Leu Lys Thr Leu Ser Val Ala Ile Gly
65                  70                  75                  80

Asp Lys Val Lys Lys Asp Gln Leu Leu Gly Val Ile Asp Pro Glu Gln
                85                  90                  95

Ala Glu Asn Gln Ile Lys Glu Val Glu Ala Thr Leu Met Glu Leu Arg
            100                 105                 110

Ala Gln Arg Gln Gln Ala Glu Ala Glu Leu Lys Leu Ala Arg Val Thr
        115                 120                 125

Tyr Ser Arg Gln Gln Arg Leu Ala Gln Thr Lys Ala Val Ser Gln Gln
    130                 135                 140

Asp Leu Asp Thr Ala Ala Thr Glu Met Ala Val Lys Gln Ala Gln Ile
145                 150                 155                 160

Gly Thr Ile Asp Ala Gln Ile Lys Arg Asn Gln Ala Ser Leu Asp Thr
                165                 170                 175

Ala Lys Thr Asn Leu Asp Tyr Thr Arg Ile Val Ala Pro Met Ala Gly
            180                 185                 190

Glu Val Thr Gln Ile Thr Thr Leu Gln Gly Gln Thr Val Ile Ala Ala
        195                 200                 205

Gln Gln Ala Pro Asn Ile Leu Thr Leu Ala Asp Met Ser Ala Met Leu
    210                 215                 220

Val Lys Ala Gln Val Ser Glu Ala Asp Val Ile His Leu Lys Pro Gly
225                 230                 235                 240
```

```
Gln Lys Ala Trp Phe Thr Val Leu Gly Asp Pro Leu Thr Arg Tyr Glu
                245                 250                 255

Gly Gln Ile Lys Asp Val Leu Pro Thr Pro Glu Lys Val Asn Asp Ala
            260                 265                 270

Ile Phe Tyr Tyr Ala Arg Phe Glu Val Pro Asn Pro Asn Gly Leu Leu
        275                 280                 285

Arg Leu Asp Met Thr Ala Gln Val His Ile Gln Leu Thr Asp Val Lys
    290                 295                 300

Asn Val Leu Thr Ile Pro Leu Ser Ala Leu Gly Asp Pro Val Gly Asp
305                 310                 315                 320

Asn Arg Tyr Lys Val Lys Leu Leu Arg Asn Gly Glu Thr Arg Glu Arg
                325                 330                 335

Glu Val Thr Ile Gly Ala Arg Asn Asp Thr Asp Val Glu Ile Val Lys
            340                 345                 350

Gly Leu Glu Ala Gly Asp Glu Val Val Ile Gly Glu Ala Lys Pro Gly
        355                 360                 365

Ala Ala Gln
    370


<210> SEQ ID NO 17
<211> LENGTH: 1158
<212> TYPE: DNA
<213> ORGANISM: Escherichia coli

<400> SEQUENCE: 17

atgaacagaa gaagaaagct gttaataccg ttgttattct gcggcgcgat gctcaccgcc      60

tgcgatgaca aatcggcgga aaacgccgcc gccatgacgc ctgaggtcgg tgtcgtcaca     120

ctctcccccg gttcggtcaa tgtgttgagc gaattgcccg gtagaaccgt tccttatgaa     180

gttgccgaga tacgtcccca ggtgggcggt attatcatta aacgcaactt tatcgaaggc     240

gataaagtga accagggcga ttcgctgtat cagattgatc ctgcaccttt acaggccgag     300

ctaaactccg ccaaaggctc gctggcgaaa gcgctctcta ccgccagcaa tgcccgcatc     360

acctttaacc gccaggcatc gttgctgaag accaactacg ttagccgtca ggattacgac     420

accgcgcgca cccagttgaa tgaagcagaa gccaatgtca ccgtcgccaa agcggctgtt     480

gaacaggcga cgatcaatct gcaatacgcg aatgtcacct cgccgattac gggcgtcagc     540

gggaaatcgt cggtgaccgt cggcgcactc gttaccgcta atcaggcaga ttcgctggtt     600

accgtacaac gtctggaccc gatttatgtc gatctcacgc agtcggtgca agatttctta     660

cgcatgaaag aagaggtcgc cagtgggcaa atcaaacagg ttcagggcag tacgccagta     720

cagctcaatc tggaaaatgg taaacgctac agccagaccg gcacgctgaa attctccgac     780

ccgacagtgg atgaaaccac gggctccgtg acgttacggg cgattttccc caacccaaat     840

ggtgacttgc tgcctggcat gtacgtcacg gcattagtgg atgaaggtag ccgccagaat     900

gtattactgg tgccgcagga aggcgtcacc cacaacgccc agggtaaagc aacggcgctc     960

attctggata aagacgatgt cgtgcagcta cgcgaaattg aagccagcaa agccatcggc    1020

gaccagtggg tcgtcacctc tggcttgcag gctggcgatc gggtgatcgt ttccggtttg    1080

caacgcattc gtccgggtat caaagcacga gcaatttcct ccagccagga aaacgccagc    1140

accgaatcga aacaataa                                                  1158


<210> SEQ ID NO 18
<211> LENGTH: 385
<212> TYPE: PRT
```

<213> ORGANISM: Escherichia coli

<400> SEQUENCE: 18

```
Met Asn Arg Arg Arg Lys Leu Leu Ile Pro Leu Leu Phe Cys Gly Ala
1               5                   10                  15

Met Leu Thr Ala Cys Asp Asp Lys Ser Ala Glu Asn Ala Ala Ala Met
            20                  25                  30

Thr Pro Glu Val Gly Val Val Thr Leu Ser Pro Gly Ser Val Asn Val
        35                  40                  45

Leu Ser Glu Leu Pro Gly Arg Thr Val Pro Tyr Glu Val Ala Glu Ile
    50                  55                  60

Arg Pro Gln Val Gly Gly Ile Ile Ile Lys Arg Asn Phe Ile Glu Gly
65                  70                  75                  80

Asp Lys Val Asn Gln Gly Asp Ser Leu Tyr Gln Ile Asp Pro Ala Pro
                85                  90                  95

Leu Gln Ala Glu Leu Asn Ser Ala Lys Gly Ser Leu Ala Lys Ala Leu
            100                 105                 110

Ser Thr Ala Ser Asn Ala Arg Ile Thr Phe Asn Arg Gln Ala Ser Leu
        115                 120                 125

Leu Lys Thr Asn Tyr Val Ser Arg Gln Asp Tyr Asp Thr Ala Arg Thr
    130                 135                 140

Gln Leu Asn Glu Ala Glu Ala Asn Val Thr Val Ala Lys Ala Ala Val
145                 150                 155                 160

Glu Gln Ala Thr Ile Asn Leu Gln Tyr Ala Asn Val Thr Ser Pro Ile
                165                 170                 175

Thr Gly Val Ser Gly Lys Ser Ser Val Thr Val Gly Ala Leu Val Thr
            180                 185                 190

Ala Asn Gln Ala Asp Ser Leu Val Thr Val Gln Arg Leu Asp Pro Ile
        195                 200                 205

Tyr Val Asp Leu Thr Gln Ser Val Gln Asp Phe Leu Arg Met Lys Glu
    210                 215                 220

Glu Val Ala Ser Gly Gln Ile Lys Gln Val Gln Gly Ser Thr Pro Val
225                 230                 235                 240

Gln Leu Asn Leu Glu Asn Gly Lys Arg Tyr Ser Gln Thr Gly Thr Leu
                245                 250                 255

Lys Phe Ser Asp Pro Thr Val Asp Glu Thr Thr Gly Ser Val Thr Leu
            260                 265                 270

Arg Ala Ile Phe Pro Asn Pro Asn Gly Asp Leu Leu Pro Gly Met Tyr
        275                 280                 285

Val Thr Ala Leu Val Asp Glu Gly Ser Arg Gln Asn Val Leu Leu Val
    290                 295                 300

Pro Gln Glu Gly Val Thr His Asn Ala Gln Gly Lys Ala Thr Ala Leu
305                 310                 315                 320

Ile Leu Asp Lys Asp Asp Val Val Gln Leu Arg Glu Ile Glu Ala Ser
                325                 330                 335

Lys Ala Ile Gly Asp Gln Trp Val Val Thr Ser Gly Leu Gln Ala Gly
            340                 345                 350

Asp Arg Val Ile Val Ser Gly Leu Gln Arg Ile Arg Pro Gly Ile Lys
        355                 360                 365

Ala Arg Ala Ile Ser Ser Ser Gln Glu Asn Ala Ser Thr Glu Ser Lys
    370                 375                 380

Gln
385
```

<210> SEQ ID NO 19
<211> LENGTH: 64
<212> TYPE: DNA
<213> ORGANISM: Artificial Sequence
<220> FEATURE:
<223> OTHER INFORMATION: primer P1

<400> SEQUENCE: 19
tcccaacgcg aaatagttta gaaacatatc tgcctcctcc ttccgctcac aattccacac 60
atta 64

<210> SEQ ID NO 20
<211> LENGTH: 64
<212> TYPE: DNA
<213> ORGANISM: Artificial Sequence
<220> FEATURE:
<223> OTHER INFORMATION: primer P2

<400> SEQUENCE: 20
tgccagccca aaaacaacac tgataaacgt gaatcccgct caagttagta taaaaaagct 60
gaac 64

<210> SEQ ID NO 21
<211> LENGTH: 1776
<212> TYPE: DNA
<213> ORGANISM: Artificial Sequence
<220> FEATURE:
<223> OTHER INFORMATION: PCR product

<400> SEQUENCE: 21
tgccagccca aaaacaacac tgataaacgt gaatcccgct caagttagta taaaaaagct 60
gaacgagaaa cgtaaaatga tataaatatc aatatattaa attagatttt gcataaaaaa 120
cagactacat aatactgtaa aacacaacat atgcagtcac tatgaatcaa ctacttagat 180
ggtattagtg acctgtaaca gactgcagtg gtcgaaaaaa aaagcccgca ctgtcaggtg 240
cgggcttttt tctgtgttaa gcttcgacga atttctgcca ttcatccgct tattatcact 300
tattcaggcg tagcaccagg cgtttaaggg caccaataac tgccttaaaa aaattacgcc 360
ccgccctgcc actcatcgca gtactgttgt aattcattaa gcattctgcc gacatggaag 420
ccatcacaga cggcatgatg aacctgaatc gccagcggca tcagcacctt gtcgccttgc 480
gtataatatt tgcccatggt gaaaacgggg gcgaagaagt tgtccatatt ggccacgttt 540
aaatcaaaac tggtgaaact cacccaggga ttggctgaga cgaaaaacat attctcaata 600
aaccctttag ggaaataggc caggttttca ccgtaacacg ccacatcttg cgaatatatg 660
tgtagaaact gccggaaatc gtcgtggtat tcactccaga gcgatgaaaa cgtttcagtt 720
tgctcatgga aaacggtgta acaagggtga acactatccc atatcaccag ctcaccgtct 780
ttcattgcca tacggaattc cggatgagca ttcatcaggc gggcaagaat gtgaataaag 840
gccggataaa acttgtgctt atttttcttt acggtcttta aaaaggccgt aatatccagc 900
tgaacggtct ggttataggt acattgagca actgactgaa atgcctcaaa atgttcttta 960
cgatgccatt gggatatatc aacggtggta tatccagtga tttttttctc cattttagct 1020
tccttagctc ctgaaaatct cggatccggc caagctagct tggctctagc tagagcgccc 1080
ggttgacgct gctagtgtta cctagcgatt tgtatcttac tgcatgttac ttcatgttgt 1140
caatacctgt ttttcgtgcg acttatcagg ctgtctactt atccggagat ccacaggacg 1200
ggtgtggtcg ccatgatcgc gtagtcgata gtggctccaa gtagcgaagc gagcaggact 1260
gggcggcggc caaagcggtc ggacagtgct ccgagaacgg gtgcgcatag aaattgcatc 1320
aacgcatata gcgctagcag cacgccatag tgactggcga tgctgtcgga atggacgata 1380
tcccgcaaga ggcccggcag taccggcata accaagccta tgcctacagc atccagggtg 1440
acggtgccga ggatgacgat gagcgcattg ttagatttca tacacggtgc ctgactgcgt 1500
tagcaattta actgtgataa actaccgcat taaagcttat cgatgataag ctgtcaaaca 1560
tgagaattcg aaatcaaata atgattttat tttgactgat agtgacctgt tcgttgcaac 1620
aaattgataa gcaatgcttt tttataatgc caacttagta taaaaaagca ggcttcaaga 1680
tctccctgtt gacaattaat catcggctcg tataatgtgt ggaattgtga gcggaaggag 1740
gaggcagata tgtttctaaa ctatttcgcg ttggga 1776

<210> SEQ ID NO 22
<211> LENGTH: 23
<212> TYPE: DNA
<213> ORGANISM: Artificial Sequence
<220> FEATURE:
<223> OTHER INFORMATION: primer P3

<400> SEQUENCE: 22
cgataaacgc gccgatattt ggc 23

<210> SEQ ID NO 23
<211> LENGTH: 24
<212> TYPE: DNA
<213> ORGANISM: Artificial Sequence
<220> FEATURE:
<223> OTHER INFORMATION: primer P4

<400> SEQUENCE: 23
gaaagacgaa gatcagcact ccca 24

<210> SEQ ID NO 24
<211> LENGTH: 667
<212> TYPE: DNA
<213> ORGANISM: Artificial Sequence
<220> FEATURE:
<223> OTHER INFORMATION: PCR product

<400> SEQUENCE: 24
cgataaacgc gccgatattt ggcatcacca tgttgctgag gaaacgacca aagctttgca 60
ctttgatctt aatatcggat gacataaaaa caccccttct tatgtttgct gtcgcgcagg 120
ctggaagccc gaggtttttt gttaatgtgg cggcagaggt agccggacct tgtagatact 180
gcgaaatctg gcactgaatc ggttaactgt ccagtcgacg gccttttgtg tgatatcaat 240
cacataaata tagggggtag agaggtaatt gacgtgacgt tcatcacaaa acgcttgtgt 300
aaaaaagcaa caaggcggcg attttcgcta aaaatggcat ttaaatgtga gtagtgtcac 360
atttttgttt tgatggtttg ttgaatcttt gtgatctgaa tcacaagata ttttcttacg 420
gcgttcacct gatgtgatct acagcatgtt atgccttcgt catacaatcg ttatgtaact 480
aagcaactca tcacctctaa aaattattct ttggtgttat ggcgagaatc gcgaacccgg 540
attattgtca aaatatcagc ctgactccct tctggctgcc agcccaaaaa caacactgat 600
aaacgtgaat ccgaggcaga tatgtttcta aactatttcg cgttgggagt gctgatcttc 660
gtctttc 667

<210> SEQ ID NO 25

<211> LENGTH: 2371
<212> TYPE: DNA
<213> ORGANISM: Artificial Sequence
<220> FEATURE:
<223> OTHER INFORMATION: PCR product

<400> SEQUENCE: 25

```
cgataaacgc gccgatattt ggcatcacca tgttgctgag gaaacgacca aagctttgca     60
ctttgatctt aatatcggat gacataaaaa cacccttct tatgtttgct gtcgcgcagg    120
ctggaagccc gaggtttttt gttaatgtgg cggcagaggt agccggacct tgtagatact    180
gcgaaatctg gcactgaatc ggttaactgt ccagtcgacg gcctttgtg tgatatcaat    240
cacataaata tagggggtag agaggtaatt gacgtgacgt tcatcacaaa acgcttgtgt    300
aaaaaagcaa caaggcggcg attttcgcta aaaatggcat ttaaatgtga gtagtgtcac    360
atttttgttt tgatggtttg ttgaatcttt gtgatctgaa tcacaagata ttttcttacg    420
gcgttcacct gatgtgatct acagcatgtt atgccttcgt catacaatcg ttatgtaact    480
aagcaactca tcacctctaa aaattattct ttggtgttat ggcgagaatc gcgaacccgg    540
attattgtca aaatatcagc ctgactccct tctggctgcc agcccaaaaa caacactgat    600
aaacgtgaat cccgctcaag ttagtataaa aaagctgaac gagaaacgta aaatgatata    660
aatatcaata tattaaatta gattttgcat aaaaaacaga ctacataata ctgtaaaaca    720
caacatatgc agtcactatg aatcaactac ttagatggta ttagtgacct gtaacagact    780
gcagtggtcg aaaaaaaaag cccgcactgt caggtgcggg ctttttctg tgttaagctt    840
cgacgaattt ctgccattca tccgcttatt atcacttatt caggcgtagc accaggcgtt    900
taagggcacc aataactgcc ttaaaaaaat tacgccccgc cctgccactc atcgcagtac    960
tgttgtaatt cattaagcat tctgccgaca tggaagccat cacagacggc atgatgaacc   1020
tgaatcgcca gcggcatcag caccttgtcg ccttgcgtat aatatttgcc catggtgaaa   1080
acgggggcga agaagttgtc catattggcc acgtttaaat caaaactggt gaaactcacc   1140
cagggattgg ctgagacgaa aaacatattc tcaataaacc ctttagggaa ataggccagg   1200
ttttcaccgt aacacgccac atcttgcgaa tatatgtgta gaaactgccg gaaatcgtcg   1260
tggtattcac tccagagcga tgaaaacgtt tcagtttgct catggaaaac ggtgtaacaa   1320
gggtgaacac tatcccatat caccagctca ccgtctttca ttgccatacg gaattccgga   1380
tgagcattca tcaggcgggc aagaatgtga ataaaggccg gataaaactt gtgcttattt   1440
ttctttacgg tctttaaaaa ggccgtaata tccagctgaa cggtctggtt ataggtacat   1500
tgagcaactg actgaaatgc ctcaaaatgt tctttacgat gccattggga tatatcaacg   1560
gtggtatatc cagtgatttt tttctccatt ttagcttcct tagctcctga aaatctcgga   1620
tccggccaag ctagcttggc tctagctaga gcgcccggtt gacgctgcta gtgttaccta   1680
gcgatttgta tcttactgca tgttacttca tgttgtcaat acctgttttt cgtgcgactt   1740
atcaggctgt ctacttatcc ggagatccac aggacgggtg tggtcgccat gatcgcgtag   1800
tcgatagtgg ctccaagtag cgaagcgagc aggactgggc ggcggccaaa gcggtcggac   1860
agtgctccga gaacgggtgc gcatagaaat tgcatcaacg catatagcgc tagcagcacg   1920
ccatagtgac tggcgatgct gtcggaatgg acgatatccc gcaagaggcc cggcagtacc   1980
ggcataacca agcctatgcc tacagcatcc agggtgacgg tgccgaggat gacgatgagc   2040
gcattgttag atttcataca cggtgcctga ctgcgttagc aatttaactg tgataaacta   2100
ccgcattaaa gcttatcgat gataagctgt caaacatgag aattcgaaat caaataatga   2160
```

ttttattttg actgatagtg acctgttcgt tgcaacaaat tgataagcaa tgctttttta 2220
taatgccaac ttagtataaa aaagcaggct tcaagatctc cctgttgaca attaatcatc 2280
ggctcgtata atgtgtggaa ttgtgagcgg aaggaggagg cagatatgtt tctaaactat 2340
ttcgcgttgg gagtgctgat cttcgtcttt c 2371

<210> SEQ ID NO 26
<211> LENGTH: 63
<212> TYPE: DNA
<213> ORGANISM: Artificial Sequence
<220> FEATURE:
<223> OTHER INFORMATION: primer P5

<400> SEQUENCE: 26
tcttgcaaaa acagcctgcg ttttcatcag taatagcgct caagttagta taaaaaagcg 60
aac 63

<210> SEQ ID NO 27
<211> LENGTH: 66
<212> TYPE: DNA
<213> ORGANISM: Artificial Sequence
<220> FEATURE:
<223> OTHER INFORMATION: primer P6

<400> SEQUENCE: 27
agcggcggta atgttctcaa acatgacgag gtttccttag ctgtttcctt ctagacggcc 60
aatgct 66

<210> SEQ ID NO 28
<211> LENGTH: 22
<212> TYPE: DNA
<213> ORGANISM: Artificial Sequence
<220> FEATURE:
<223> OTHER INFORMATION: primer P7

<400> SEQUENCE: 28
cgtttaccag ttctaatagc ac 22

<210> SEQ ID NO 29
<211> LENGTH: 21
<212> TYPE: DNA
<213> ORGANISM: Artificial Sequence
<220> FEATURE:
<223> OTHER INFORMATION: primer P8

<400> SEQUENCE: 29
tttatagaca ccaatcccga g 21

<210> SEQ ID NO 30
<211> LENGTH: 28
<212> TYPE: DNA
<213> ORGANISM: Artificial Sequence
<220> FEATURE:
<223> OTHER INFORMATION: primer P9

<400> SEQUENCE: 30
tagcggccgc gccgatgtca cagtgcct 28

<210> SEQ ID NO 31
<211> LENGTH: 65
<212> TYPE: DNA
<213> ORGANISM: Artificial Sequence
<220> FEATURE:

<223> OTHER INFORMATION: primer P10

<400> SEQUENCE: 31
tagcggccgc tccacacatt atacgagccg atgattaatt gtcaaggtga atcacgacaa 60
agcgt 65

<210> SEQ ID NO 32
<211> LENGTH: 47
<212> TYPE: DNA
<213> ORGANISM: Artificial Sequence
<220> FEATURE:
<223> OTHER INFORMATION: primer P11

<400> SEQUENCE: 32
tagcggccgc ctccttccgc tcacaattcc acacattata cgagccg 47

<210> SEQ ID NO 33
<211> LENGTH: 4442
<212> TYPE: DNA
<213> ORGANISM: Artificial Sequence
<220> FEATURE:
<223> OTHER INFORMATION: plasmid pGL2-Ptac-SD1-yibH

<400> SEQUENCE: 33
aggcactgtg acatcggcta aagaaaaatc atcgaagcta atgaagtaat atgcaaaaat 60
aattagtcct tacaaggagc aaagttccat aatctccccc ctccccctca atgatccaaa 120
taaagataat gcatccagct ggtcattctt agcagcactt tccgcatcac cgaaacatgg 180
ctgaaatggt cggagtaaac cgccacctgg gcgtagatgc cgtcgggtaa ggcatcgata 240
tcatcgttag ggtccagttc aatggttccc agcacaccgt ccgtgccggg cacgaccgtt 300
aatgattgca ataccccctg cgcctgataa gaaccgcctg gcacgacagg taaaatacta 360
gtcagtttgc cgtgaaacac ctgcccaggt agcgcgttaa acaccacttc cgcatcatcg 420
ccaggtttca gacgtaacag cgagttttgc cgaaattggg cgacaatttg ccgtttttgc 480
tcggggatga agaccatcac cggacgcagc ggcaaggcag ctgcgtatgt acctgggcgg 540
atcagtacct gagtaacgta gccattgctc ggcgcgcgaa tgacagtctg ctcaaggtta 600
tattttgctt cagtaagttg cgctcttaag ctcacaatct gcgattgctc gccgttaacc 660
atactgtcga gctggctctg gatctgcgcc tgctccgcca ccgagccttt caccagcgca 720
tcctgcgcga ggaaattttg ccgcgcatcg tcgatgtcac gttccgagaa cggattcacc 780
gccgcctggc tgcctttcaa gtaacgttga taatttttaa acagacggtc gcgctccgct 840
gaaacctggg tggtgttggc ctgcgcttca gtgagctgcg cacgcagcgt ctttatatta 900
tgcgtcgccg tcatcaggtc agcctgaagt ctgtcaactc gcgcctggta acgaaccggg 960
tcgagcttaa aaagcacctc gcccttttga ataagctgat tattcttgtc agtgacttca 1020
gtaacaattc ccgtcacctg tggcgtgata gggatcgcta tcactgcctt ttgcgcggta 1080
aaagtgtaag ggtggttgta gttcatcaac aaaatcaaac cactcaccag aaacacgcct 1140
cccagcgccg ccgtcgccag cgtccactga tttaccggaa tgcggaagat tttaaagacc 1200
gcccacgcca gcgccacgta agttaaaaca atcaatagat ccataattag atctccttcc 1260
gctcacaatt ccacacatta tacgagccga tgattaattg tcaaggtgaa tcacgacaaa 1320
gcgtatcaaa aacgtatgga gtagggctct aaactctgta taaaaagttt ccagctagct 1380
gataacggga aagaaacaga gaagggcaca aatattgtgt actttaatgt gccctttaat 1440
ttattgattg gtggttgaat tgtccgtaac tttttgattt aagtgcaaat ttctaataaa 1500

```
ttagaacact ttcttaaatt gtcatttggc atattacgaa caattccgcg taaaaacgtt   1560
ctgttacgct aaacccttat ccagcaggct ttcaaggatg taaaccataa cactctgcga   1620
actagtgtta cattgcgtgt agctttgagt gggcaacttt gtgtacactt ttgtgtaccc   1680
aaaaacaaaa atgtgtaccc attcaatgat caccgacaca aagctcagga aggcgctcgg   1740
caagaaaaga gatgatatcg agattatttc tgattcgcac gcgctcaagt tagtataaaa   1800
aagctgaacg agaaacgtaa aatgatataa atatcaatat attaaattag attttgcata   1860
aaaaacagac tacataatac tgtaaaacac aacatatgca gtcactatga atcaactact   1920
tagatggtat tagtgacctg taacagactg cagtggtcga aaaaaaaagc ccgcactgtc   1980
aggtgcgggc tttttctgt gttaagcttc gacgaatttc tgccattcat ccgcttatta    2040
tcacttattc aggcgtagca ccaggcgttt aagggcacca ataactgcct taaaaaaatt   2100
acgccccgcc ctgccactca tcgcagtact gttgtaattc attaagcatt ctgccgacat   2160
ggaagccatc acagacggca tgatgaacct gaatcgccag cggcatcagc accttgtcgc   2220
cttgcgtata atatttgccc atggtgaaaa cgggggcgaa gaagttgtcc atattggcca   2280
cgtttaaatc aaaactggtg aaactcaccc agggattggc tgagacgaaa aacatattct   2340
caataaaccc tttagggaaa taggccaggt tttcaccgta acacgccaca tcttgcgaat   2400
atatgtgtag aaactgccgg aaatcgtcgt ggtattcact ccagagcgat gaaaacgttt   2460
cagtttgctc atggaaaacg gtgtaacaag ggtgaacact atcccatatc accagctcac   2520
cgtctttcat tgccatacgg aattccggat gagcattcat caggcgggca agaatgtgaa   2580
taaaggccgg ataaaacttg tgcttatttt tctttacggt ctttaaaaag gccgtaatat   2640
ccagctgaac ggtctggtta taggtacatt gagcaactga ctgaaatgcc tcaaaatgtt   2700
ctttacgatg ccattgggat atatcaacgg tggtatatcc agtgattttt ttctccattt   2760
tagcttcctt agctcctgaa aatctcggat ccggccaagc tagcttggct ctagctagag   2820
cgcccggttg acgctgctag tgttacctag cgatttgtat cttactgcat gttacttcat   2880
gttgtcaata cctgttttc gtgcgactta tcaggctgtc tacttatccg gaattcgaaa    2940
tcaaataatg attttatttt gactgatagt gacctgttcg ttgcaacaaa ttgataagca   3000
atgctttttt ataatgccaa cttagtataa aaaagcaggc ttcaattacc ctgttatccc   3060
taagatctag cttgcgaggg tgctacttaa gcctttaggg ttttaaggtc tgttttgtag   3120
aggagcaaac agcgtttgcg acatcctttt gtaatactgc ggaactgact aaagtagtga   3180
gttatacaca gggctgggat ctattctttt tatctttttt tattctttct ttattctata   3240
aattataacc acttgaatat aaacaaaaaa aacacacaaa ggtctagcgg aatttacaga   3300
gggtctagca gaatttacaa gttttccagc aaaggtctag cagaatttac agatacccac   3360
aactcaaagg aaaaggacta gtaattatca ttgactagcc catctcaatt ggtatagtga   3420
ttaaaatcac ctagaccaat tgagatgtat gtctgaatta gttgttttca aagcaaatga   3480
actagcgatt agtcgctatg acttaacgga gcatgaaacc aagctaattt tatgctgtgt   3540
ggcactactc aaccccacga ttgaaaaccc tacaaggaaa gaacggacgg tatcgttcac   3600
ttataaccaa tacgctcaga tgatgaacat cagtagggaa aatgcttatg gtgtattagc   3660
taaagcaacc agagagctga tgacgagaac tgtggaaatc aggaatcctt tggttaaagg   3720
ctttgagatt ttccagtgga caaactatgc caagttctca agcgaaaaat tagaattagt   3780
ttttagtgaa gagatattgc cttatctttt ccagttaaaa aaattcataa aatataatct   3840
```

-continued

```
ggaacatgtt aagtcttttg aaaacaaata ctctatgagg atttatgagt ggttattaaa   3900

agaactaaca caaaagaaaa ctcacaaggc aaatatagag attagccttg atgaatttaa   3960

gttcatgtta atgcttgaaa ataactacca tgagtttaaa aggcttaacc aatgggtttt   4020

gaaaccaata agtaaagatt taaacactta cagcaatatg aaattggtgg ttgataagcg   4080

aggccgcccg actgatacgt tgattttcca agttgaacta gatagacaaa tggatctcgt   4140

aaccgaactt gagaacaacc agataaaaat gaatggtgac aaaataccaa caaccattac   4200

atcagattcc tacctacgta acggactaag aaaaacacta cacgatgctt taactgcaaa   4260

aattcagctc accagttttg aggcaaaatt tttgagtgac atgcaaagta agcatgatct   4320

caatggttcg ttctcatggc tcacgcaaaa acaacgaacc acactagaga acatactggc   4380

taaatacgga aggatctgag gttcttatgg ctcttgtatc tatcattacc ctgttatccc   4440

ta                                                                  4442


<210> SEQ ID NO 34
<211> LENGTH: 21
<212> TYPE: DNA
<213> ORGANISM: Artificial Sequence
<220> FEATURE:
<223> OTHER INFORMATION: primer P12

<400> SEQUENCE: 34

agtgtaaggg tggttgtagt t                                               21


<210> SEQ ID NO 35
<211> LENGTH: 19
<212> TYPE: DNA
<213> ORGANISM: Artificial Sequence
<220> FEATURE:
<223> OTHER INFORMATION: primer P13

<400> SEQUENCE: 35

gtttagagcc ctactccat                                                  19


<210> SEQ ID NO 36
<211> LENGTH: 19
<212> TYPE: DNA
<213> ORGANISM: Artificial Sequence
<220> FEATURE:
<223> OTHER INFORMATION: primer P14

<400> SEQUENCE: 36

cggaaggatc tgaggttct                                                  19


<210> SEQ ID NO 37
<211> LENGTH: 20
<212> TYPE: DNA
<213> ORGANISM: Artificial Sequence
<220> FEATURE:
<223> OTHER INFORMATION: primer P15

<400> SEQUENCE: 37

agcaggcgca gatccagagc                                                 20


<210> SEQ ID NO 38
<211> LENGTH: 272
<212> TYPE: DNA
<213> ORGANISM: Artificial Sequence
<220> FEATURE:
<223> OTHER INFORMATION: PCR product

<400> SEQUENCE: 38
```

```
agtgtaaggg tggttgtagt tcatcaacaa aatcaaacca ctcaccagaa acacgcctcc      60

cagcgccgcc gtcgccagcg tccactgatt taccggaatg cggaagattt taaagaccgc     120

ccacgccagc gccacgtaag ttaaaacaat caatagatcc ataattagat ctccttccgc     180

tcacaattcc acacattata cgagccgatg attaattgtc aaggtgaatc acgacaaagc     240

gtatcaaaaa cgtatggagt agggctctaa ac                                   272
```

<210> SEQ ID NO 39
<211> LENGTH: 750
<212> TYPE: DNA
<213> ORGANISM: Artificial Sequence
<220> FEATURE:
<223> OTHER INFORMATION: PCR product

<400> SEQUENCE: 39

```
cggaaggatc tgaggttctt atggctcttg tatctatcat taccctgtta tccctaaggc      60

actgtgacat cggctaaaga aaaatcatcg aagctaatga agtaatatgc aaaaataatt     120

agtccttaca aggagcaaag ttccataatc tccccctcc ccctcaatga tccaaataaa     180

gataatgcat ccagctggtc attcttagca gcactttccg catcaccgaa acatggctga     240

aatggtcgga gtaaaccgcc acctgggcgt agatgccgtc gggtaaggca tcgatatcat     300

cgttagggtc cagttcaatg gttcccagca caccgtccgt gccgggcacg accgttaatg     360

attgcaatac cccctgcgcc tgataagaac cgcctggcac gacaggtaaa atactagtca     420

gtttgccgtg aaacacctgc ccaggtagcg cgttaaacac cacttccgca tcatcgccag     480

gtttcagacg taacagcgag ttttgccgaa attgggcgac aatttgccgt ttttgctcgg     540

ggatgaagac catcaccgga cgcagcggca aggcagctgc gtatgtacct gggcggatca     600

gtacctgagt aacgtagcca ttgctcggcg cgcgaatgac agtctgctca aggttatatt     660

ttgcttcagt aagttgcgct cttaagctca caatctgcga ttgctcgccg ttaaccatac     720

tgtcgagctg gctctggatc tgcgcctgct                                      750
```

<210> SEQ ID NO 40
<211> LENGTH: 70
<212> TYPE: DNA
<213> ORGANISM: Artificial Sequence
<220> FEATURE:
<223> OTHER INFORMATION: primer P16

<400> SEQUENCE: 40

```
cgtataatgt gtggaattgt gataaggagg tgatatgcaa atgaagaaat tgctccccat      60

tcttatcggc                                                             70
```

<210> SEQ ID NO 41
<211> LENGTH: 60
<212> TYPE: DNA
<213> ORGANISM: Artificial Sequence
<220> FEATURE:
<223> OTHER INFORMATION: primer P17

<400> SEQUENCE: 41

```
agtttgatcg cgctaaatac tgcttcacca caaggacgct caagttagta taaaaaagct      60
```

<210> SEQ ID NO 42
<211> LENGTH: 19
<212> TYPE: DNA
<213> ORGANISM: Artificial Sequence
<220> FEATURE:

<223> OTHER INFORMATION: primer P18

<400> SEQUENCE: 42
cctggctcaa cgaactgaa 19

<210> SEQ ID NO 43
<211> LENGTH: 20
<212> TYPE: DNA
<213> ORGANISM: Artificial Sequence
<220> FEATURE:
<223> OTHER INFORMATION: primer P19

<400> SEQUENCE: 43
tctgctcaat cagcacaact 20

<210> SEQ ID NO 44
<211> LENGTH: 2279
<212> TYPE: DNA
<213> ORGANISM: Artificial Sequence
<220> FEATURE:
<223> OTHER INFORMATION: PCR product

<400> SEQUENCE: 44
tctgctcaat cagcacaact tcatcacgca ctgggtcaaa gggtagcaag actgcggcgt 60
gaccgcgctc aaaaatttcc cgccgcacct catgactcat ttgcccgttg aatagacgat 120
gacgaaatct ataaagatct aatgaaaaaa agccgcgata aagtgtttct cgtgcaataa 180
tttctacatc gtttttgcca aatgtaacgg gcaggttgtc tggcttaagc attgttaatg 240
tcctggcact aatagtgaat taaatgtgaa tttcagcgac gtttgactgc cgtttgagca 300
gtcatgtgtt aaattgaggc acattaacgc cctatggcac gtaacgccaa ccttttgcgg 360
tagcggcttc tgctagaatc cgcaataatt ttacagtttg atcgcgctaa atactgcttc 420
accacaagga cgctcaagtt agtataaaaa agctgaacga gaaacgtaaa atgatataaa 480
tatcaatata ttaaattaga ttttgcataa aaaacagact acataatact gtaaaacaca 540
acatatgcag tcactatgaa tcaactactt agatggtatt agtgacctgt aacagactgc 600
agtggtcgaa aaaaaaagcc cgcactgtca ggtgcgggct tttttctgtg ttaagcttcg 660
acgaatttct gccattcatc cgcttattat cacttattca ggcgtagcac caggcgttta 720
agggcaccaa taactgcctt aaaaaaatta cgccccgccc tgccactcat cgcagtactg 780
ttgtaattca ttaagcattc tgccgacatg gaagccatca cagacggcat gatgaacctg 840
aatcgccagc ggcatcagca ccttgtcgcc ttgcgtataa tatttgccca tggtgaaaac 900
gggggcgaag aagttgtcca tattggccac gtttaaatca aaactggtga aactcaccca 960
gggattggct gagacgaaaa acatattctc aataaaccct ttagggaaat aggccaggtt 1020
ttcaccgtaa cacgccacat cttgcgaata tatgtgtaga aactgccgga aatcgtcgtg 1080
gtattcactc cagagcgatg aaaacgtttc agtttgctca tggaaaacgg tgtaacaagg 1140
gtgaacacta tcccatatca ccagctcacc gtctttcatt gccatacgga attccggatg 1200
agcattcatc aggcgggcaa gaatgtgaat aaaggccgga taaaacttgt gcttattttt 1260
ctttacggtc tttaaaaagg ccgtaatatc cagctgaacg gtctggttat aggtacattg 1320
agcaactgac tgaaatgcct caaaatgttc tttacgatgc cattgggata tatcaacggt 1380
ggtatatcca gtgatttttt tctccatttt agcttcctta gctcctgaaa atctcggatc 1440
cgatatctag ctagagcgcc cggttgacgc tgctagtgtt acctagcgat ttgtatctta 1500
ctgcatgtta cttcatgttg tcaatacctg tttttcgtgc gacttatcag gctgtctact 1560

```
tatccggaga tccacaggac gggtgtggtc gccatgatcg cgtagtcgat agtggctcca   1620

agtagcgaag cgagcaggac tgggcggcgg ccaaagcggt cggacagtgc tccgagaacg   1680

ggtgcgcata gaaattgcat caacgcatat agcgctagca gcacgccata gtgactggcg   1740

atgctgtcgg aatggacgat atcccgcaag aggcccggca gtaccggcat aaccaagcct   1800

atgcctacag catccagggt gacggtgccg aggatgacga tgagcgcatt gttagatttc   1860

atacacggtg cctgactgcg ttagcaattt aactgtgata aactaccgca ttaaagctta   1920

tcgatgataa gctgtcaaac atgagaattc gaaatcaaat aatgatttta ttttgactga   1980

tagtgacctg ttcgttgcaa caaattgata agcaatgctt ttttataatg ccaacttagt   2040

ataaaaaagc aggcttcaag atctctcacc taccaaacaa tgccccccctg caaaaaataa   2100

attcataaaa aacatacaga taaccatctg cggtgataaa ttatctctgg cggtgttgac   2160

aattaatcat cggctcgtat aatgtgtgga attgtgataa ggaggtgata tgcaaatgaa   2220

gaaattgctc cccattctta tcggcctgag cctttctggg ttcagttcgt tgagccagg    2279
```

<210> SEQ ID NO 45
<211> LENGTH: 22
<212> TYPE: DNA
<213> ORGANISM: Artificial Sequence
<220> FEATURE:
<223> OTHER INFORMATION: primer P20

<400> SEQUENCE: 45

```
cctccctttt cgatagcgac aa                                               22
```

<210> SEQ ID NO 46
<211> LENGTH: 21
<212> TYPE: DNA
<213> ORGANISM: Artificial Sequence
<220> FEATURE:
<223> OTHER INFORMATION: primer P21

<400> SEQUENCE: 46

```
ctcctttcta agccgctaca g                                                21
```

<210> SEQ ID NO 47
<211> LENGTH: 5251
<212> TYPE: DNA
<213> ORGANISM: Artificial Sequence
<220> FEATURE:
<223> OTHER INFORMATION: plasmid pAH162-tetA-tetR-2Ter-PyeaS-yeaS

<400> SEQUENCE: 47

```
gacgtcctaa ttcccatgtc agccgttaag tgttcctgtg tcactgaaaa ttgctttgag     60

aggctctaag ggcttctcag tgcgttacat ccctggcttg ttgtccacaa ccgttaaacc    120

ttaaaagctt taaaagcctt atatattctt tttttctta taaaacttaa aaccttagag    180

gctatttaag ttgctgattt atattaattt tattgttcaa acatgagagc ttagtacgtg    240

aaacatgaga gcttagtacg ttagccatga gagcttagta cgttagccat gagggtttag    300

ttcgttaaac atgagagctt agtacgttaa acatgagagc ttagtacgtg aaacatgaga    360

gcttagtacg tactatcaac aggttgaact gctgatcttc agatcctcta cgccggacgc    420

atcgtggccg gatcttgcgg ccgcaaaaat taaaaatgaa gttttggagg cctcatttgg    480

tgacgaaata actaagcact tgtctcctgt ttactcccct gagcttgagg ggtcaacatg    540

aaggtcattg atagcaggat aataatacag taaaacgcta aaccaataat ccaaatccag    600
```

```
ccatcccaaa ttggtagtga atgattataa ataacagtaa acagtaatgg gccaataaca    660

ccggttgcat tggtaaggct caccaataat ccctgtaaag caccttgctc atgactcttt    720

gtttggatag acatcactcc ctgtaatgca ggtaaagcga tcccaccacc agccaataaa    780

attaaaacag ggaaatctaa ccaaccttca gatataaacg ctaaaaaggc aaatgcacta    840

ctatctgcaa taaattcgag cagtactgcc gtttttttcgc cccatttagt ggctattctt    900

cctgccacaa aggcttggaa tactgagtgt aaaagaccaa gacccgctaa tgaaaagcca    960

accatcatgc tattccatcc aaaacgattt tcggtaaata gcacccacac cgttgcggga   1020

atttggccta tcaattcgaa atcaaataat gattttattt tgactgatag tgacctgttc   1080

gttgcaacaa attgataagc aatgcttttt tataatgcca acttagtata aaaaagcagg   1140

cttcagagcg atggcccccg atggtagtgt ggggtctccc catgcgagag tagggaactg   1200

ccaggcatca aataaaacga aaggctcagt cgaaagactg ggcctttcgt tttatctgtt   1260

gtttgtcggt gaacgctctc ctgagtagga caaatccgcc gggagcggat ttgaacgttg   1320

cgaagcaacg gcccggaggg tggcgggcag gacgcccgcc ataaactgcc aggcatcaaa   1380

ttaagcagaa ggccatcctg acggatggcc tttttgcgtg gccagtgcca agcttgcatg   1440

cctgcaggtc gactctagag gatcccccgt tcactggagc atgcctgatt aatgattcaa   1500

ttatcgggtt gatatcaggt taaaacctga ttttctcctt tctaagccgc tacagattgg   1560

ttagcatatt cacctttaat cgcgcatgat cgaaagataa ttaaagaggt taatgtgttc   1620

gctgaatacg gggttctgaa ttactggacc tatctggttg ggccattttt tattgtgttg   1680

gtgccagggc caaataccct gtttgtactc aaaaatagcg tcagtagcgg tatgaaaggc   1740

ggttatcttg cggcctgcgg tgtatttatt ggcgatgcgg tattgatgtt tctggcatgg   1800

gctggagtgg cgacattaat taagaccacc ccgatattat tcaacattgt acgttatctt   1860

ggtgcgtttt atttgctcta tctggggagt aaaattcttt acgcgaccct gaagggtaaa   1920

aatagcgagg ccaaatccga tgagccccaa tacggtgcta tttttaaacg cgcgttaatt   1980

ttgagcctga ctaatccgaa agccattttg ttctatgtgt cgtttttcgt acagtttatc   2040

gatgttaatg ccccacatac gggaatttca ttctttattc tggcggcgac gctggaactg   2100

gtgagtttct gctatttgag cttcctgatt atatctggtg cttttgtcac gcagtacata   2160

cgtaccaaaa agaaactggc taaagttggc aactcactga ttggtttgat gttcgtgggt   2220

ttcgctgccc gactggcgac gctgcaatcc tgacggggta ccgagctcga attctcatgt   2280

ttgacagctt atcactgatc agtgaattaa tggcgatgac gcatcctcac gataatatcc   2340

gggtaggcgc aatcactttc gtctctactc cgttacaaag cgaggctggg tatttcccgg   2400

cctttctgtt atccgaaatc cactgaaagc acagcggctg gctgaggaga taaataataa   2460

acgaggggct gtatgcacaa agcatcttct gttgagttaa gaacgagtat cgagatggca   2520

catagccttg ctcaaattgg aatcaggttt gtgccaatac cagtagaaac agacgaagaa   2580

gctagaggtg aatcacgaca aagcgtatca aaaacgtatg gagtagggct ctaaactctg   2640

tataaaaagt ttccagctag ctgataacgg gaaagaaaca gagaagggca caaatattgt   2700

gtactttaat gtgcccttta atttattgat tggtggttga attgtccgta actttttgat   2760

ttaagtgcaa atttctaata aattagaaca ctttcttaaa ttgtcatttg gcatattacg   2820

aacaattccg cgtaaaaacg ttctgttacg ctaaaccctt atccagcagg ctttcaagga   2880

tgtaaaccat aacactctgc gaactagtgt tacattgcgt gtagctttga gtgggcaact   2940

ttgtgtacac ttttgtgtac ccaaaaacaa aaatgtgtac ccattcaatg atcaccgaca   3000
```

```
caaagctcag gaaggcgctc ggcaagaaaa gagatgatat cgagattatt tctgattcgc   3060
acgagctttc tagacgctca agttagtata aaaaagctga acgagaaacg taaaatgata   3120
taaatatcaa tatattaaat tagattttgc ataaaaaaca gactacataa tactgtaaaa   3180
cacaacatat gcagtcacta tgaatcaact acttagatgg tattagtgac ctgtaacaga   3240
ctgcgggccc aggttatgct gcttttaaga cccactttca catttaagtt gtttttctaa   3300
tccgcatatg atcaattcaa ggccgaataa gaaggctggc tctgcacctt ggtgatcaaa   3360
taattcgata gcttgtcgta ataatggcgg catactatca gtagtaggtg tttccctttc   3420
ttctttagcg acttgatgct cttgatcttc caatacgcaa cctaaagtaa aatgccccac   3480
agcgctgagt gcatataatg cattctctag tgaaaaacct tgttggcata aaaaggctaa   3540
ttgattttcg agagtttcat actgtttttc tgtaggccgt gtacctaaat gtacttttgc   3600
tccatcgcga tgacttagta aagcacatct aaaactttta gcgttattac gtaaaaaatc   3660
ttgccagctt tccccttcta aagggcaaaa gtgagtatgg tgcctatcta acatctcaat   3720
ggctaaggcg tcgagcaaag cccgcttatt ttttacatgc caatacaatg taggctgctc   3780
tacacctagc ttctgggcga gtttacgggt tgttaaacct tcgattccga cctcattaag   3840
cagctctaat gcgctgttaa tcactttact tttatctaat ctagacatca ttaattccta   3900
atttttgttg acactctatc attgatagag ttattttacc actccctatc agtgatagag   3960
aaaagtgaaa tgaatagttc gacaaagatc gcattggtaa ttacgttact cgatgccatg   4020
gggattggcc ttatcatgcc agtcttgcca acgttattac gtgaatttat tgcttcggaa   4080
gatatcgcta accactttgg cgtattgctt gcactttatg cgttaatgca ggttatcttt   4140
gctccttggc ttggaaaaat gtctgaccga tttggtcggc gcccagtgct gttgttgtca   4200
ttaataggcg catcgctgga ttacttattg ctggcttttt caagtgcgct ttggatgctg   4260
tatttaggcc gtttgctttc agggatcaca ggagctactg gggctgtcgc ggcatcggtc   4320
attgccgata ccacctcagc ttctcaacgc gtgaagtggt tcggttggtt aggggcaagt   4380
tttgggcttg gtttaatagc ggggcctatt attggtggtt ttgcaggaga gatttcaccg   4440
catagtccct tttttatcgc tgcgttgcta aatattgtca ctttccttgt ggttatgttt   4500
tggttccgtg aaaccaaaaa tacacgtgat aatacagata ccgaagtagg ggttgagacg   4560
caatcgaatt cggtatacat cactttattt aaaacgatgc ccattttgtt gattatttat   4620
ttttcagcgc aattgatagg ccaaattccc gcaacggtgt gggtgctatt taccgaaaat   4680
cgttttggat ggaatagcat gatggttggc ttttcattag cgggtcttgg tcttttacac   4740
tcagtattcc aagcctttgt ggcaggaaga atagccacta aatggggcga aaaaacggca   4800
gtactgctcg aatttattgc agatagtagt gcatttgcct ttttagcgtt tatatctgaa   4860
ggttggttag atttccctgt tttaatttta ttggctggtg gtgggatcgc tttacctgca   4920
ttacagggag tgatgtctat ccaaacaaag agtcatgagc aaggtgcttt acagggatta   4980
ttggtgagcc ttaccaatgc aaccggtgtt attggcccat tactgtttac tgttatttat   5040
aatcattcac taccaatttg ggatggctgg atttggatta ttggtttagc gttttactgt   5100
attattatcc tgctatcgat gaccttcatg ttaacccctc aagctcaggg gagtaaacag   5160
gagacaagtg cttagttatt tcgtcaccaa atgatgttat tccgcgaaat ataatgaccc   5220
tcttgataac ccaagagggc atttttttacg a                                 5251
```

<210> SEQ ID NO 48

<211> LENGTH: 33
<212> TYPE: DNA
<213> ORGANISM: Artificial Sequence
<220> FEATURE:
<223> OTHER INFORMATION: primer P22

<400> SEQUENCE: 48
agctgacgat cgttcactgg agcatgcctg att 33

<210> SEQ ID NO 49
<211> LENGTH: 32
<212> TYPE: DNA
<213> ORGANISM: Artificial Sequence
<220> FEATURE:
<223> OTHER INFORMATION: primer P23

<400> SEQUENCE: 49
agctgacgat cgtcaggatt gcagcgtcgc ca 32

<210> SEQ ID NO 50
<211> LENGTH: 22
<212> TYPE: DNA
<213> ORGANISM: Artificial Sequence
<220> FEATURE:
<223> OTHER INFORMATION: primer P24

<400> SEQUENCE: 50
agtagagacg aaagtgattg cg 22

<210> SEQ ID NO 51
<211> LENGTH: 20
<212> TYPE: DNA
<213> ORGANISM: Artificial Sequence
<220> FEATURE:
<223> OTHER INFORMATION: primer P25

<400> SEQUENCE: 51
gccataaact gccaggcatc 20

<210> SEQ ID NO 52
<211> LENGTH: 1012
<212> TYPE: DNA
<213> ORGANISM: Artificial Sequence
<220> FEATURE:
<223> OTHER INFORMATION: PCR product

<400> SEQUENCE: 52
gccataaact gccaggcatc aaattaagca gaaggccatc ctgacggatg gcctttttgc 60
gtggccagtg ccaagcttgc atgcctgcag gtcgactcta gaggatcccc cgttcactgg 120
agcatgcctg attaatgatt caattatcgg gttgatatca ggttaaaacc tgattttctc 180
ctttctaagc cgctacagat tggttagcat attcaccttt aatcgcgcat gatcgaaaga 240
taattaaaga ggttaatgtg ttcgctgaat acggggttct gaattactgg acctatctgg 300
ttggggccat ttttattgtg ttggtgccag ggccaaatac cctgtttgta ctcaaaaata 360
gcgtcagtag cggtatgaaa ggcggttatc ttgcggcctg cggtgtattt attggcgatg 420
cggtattgat gtttctggca tgggctggag tggcgacatt aattaagacc accccgatat 480
tattcaacat tgtacgttat cttggtgcgt tttatttgct ctatctgggg agtaaaattc 540
tttacgcgac cctgaagggt aaaaatagcg aggccaaatc cgatgagccc caatacggtg 600
ctatttttaa acgcgcgtta attttgagcc tgactaatcc gaaagccatt ttgttctatg 660
tgtcgttttt cgtacagttt atcgatgtta atgccccaca tacgggaatt tcattcttta 720
ttctggcggc gacgctggaa ctggtgagtt tctgctattt gagcttcctg attatatctg 780
gtgcttttgt cacgcagtac atacgtacca aaaagaaact ggctaaagtt ggcaactcac 840
tgattggttt gatgttcgtg ggtttcgctg cccgactggc gacgctgcaa tcctgacggg 900
gtaccgagct cgaattctca tgtttgacag cttatcactg atcagtgaat taatggcgat 960
gacgcatcct cacgataata tccgggtagg cgcaatcact ttcgtctcta ct 1012

<210> SEQ ID NO 53
<211> LENGTH: 64
<212> TYPE: DNA
<213> ORGANISM: Artificial Sequence
<220> FEATURE:
<223> OTHER INFORMATION: primer P26

<400> SEQUENCE: 53
aagtcacagg tgatgtttta ttgtccttca tcgttttgaa gcctgctttt ttatactaag 60
ttgg 64

<210> SEQ ID NO 54
<211> LENGTH: 60
<212> TYPE: DNA
<213> ORGANISM: Artificial Sequence
<220> FEATURE:
<223> OTHER INFORMATION: primer P27

<400> SEQUENCE: 54
gctcagccca ataaataatg ggagcagttt tttcatttat cccccaggaa aaattggtta 60

<210> SEQ ID NO 55
<211> LENGTH: 21
<212> TYPE: DNA
<213> ORGANISM: Artificial Sequence
<220> FEATURE:
<223> OTHER INFORMATION: primer P28

<400> SEQUENCE: 55
gtgaaagtca caggtgatgt t 21

<210> SEQ ID NO 56
<211> LENGTH: 20
<212> TYPE: DNA
<213> ORGANISM: Artificial Sequence
<220> FEATURE:
<223> OTHER INFORMATION: primer P29

<400> SEQUENCE: 56
ataaggtggc tgaacgtgcc 20

<210> SEQ ID NO 57
<211> LENGTH: 363
<212> TYPE: DNA
<213> ORGANISM: Escherichia coli

<400> SEQUENCE: 57
atgtttctaa actatttcgc gttgggagtg ctgatcttcg tctttctggt gatttttat 60 ggaatcatcg cgatacatga catcccttat ctgattgcca aaaagcgcaa ccatccccat 120
gccgacgcta ttcatacggc gggctgggtg agcctgttta ctctgcatgt tatctggccg 180
tttctgtgga tctgggcgac gctctatcaa ccggagcgtg gctggggtat gcagtcacat 240
gttgcgtcgc aggagaaagc gactgacccg gaaatcgccg cactttctga ccgaatttcc 300

```
cggctggagc atcaactcgc cgccgagaaa aagactgact attccacgtt cccggagatc    360

taa                                                                  363


<210> SEQ ID NO 58
<211> LENGTH: 120
<212> TYPE: PRT
<213> ORGANISM: Escherichia coli

<400> SEQUENCE: 58

Met Phe Leu Asn Tyr Phe Ala Leu Gly Val Leu Ile Phe Val Phe Leu
1               5                   10                  15

Val Ile Phe Tyr Gly Ile Ile Ala Ile His Asp Ile Pro Tyr Leu Ile
            20                  25                  30

Ala Lys Lys Arg Asn His Pro His Ala Asp Ala Ile His Thr Ala Gly
        35                  40                  45

Trp Val Ser Leu Phe Thr Leu His Val Ile Trp Pro Phe Leu Trp Ile
    50                  55                  60

Trp Ala Thr Leu Tyr Gln Pro Glu Arg Gly Trp Gly Met Gln Ser His
65                  70                  75                  80

Val Ala Ser Gln Glu Lys Ala Thr Asp Pro Glu Ile Ala Ala Leu Ser
                85                  90                  95

Asp Arg Ile Ser Arg Leu Glu His Gln Leu Ala Ala Glu Lys Lys Thr
            100                 105                 110

Asp Tyr Ser Thr Phe Pro Glu Ile
        115                 120


<210> SEQ ID NO 59
<211> LENGTH: 78
<212> TYPE: DNA
<213> ORGANISM: Artificial Sequence
<220> FEATURE:
<223> OTHER INFORMATION: primer P30

<400> SEQUENCE: 59

gctcaggccg ataagaatgg ggagcaattt cttcatattg ttcctcctgt gtgagctcac     60

aattccacac attatacg                                                   78


<210> SEQ ID NO 60
<211> LENGTH: 64
<212> TYPE: DNA
<213> ORGANISM: Artificial Sequence
<220> FEATURE:
<223> OTHER INFORMATION: primer P31

<400> SEQUENCE: 60

ttaaattgag gcacattaac gccctatggc acgtaacgct caagttagta taaaaaagct     60

gaac                                                                  64


<210> SEQ ID NO 61
<211> LENGTH: 21
<212> TYPE: DNA
<213> ORGANISM: Artificial Sequence
<220> FEATURE:
<223> OTHER INFORMATION: primer P32

<400> SEQUENCE: 61

ttcaaaggca gcatcacgat c                                               21


<210> SEQ ID NO 62
<211> LENGTH: 18
```

<212> TYPE: DNA
<213> ORGANISM: Artificial Sequence
<220> FEATURE:
<223> OTHER INFORMATION: primer P33

<400> SEQUENCE: 62
acgggcaggt tgtctggc 18

<210> SEQ ID NO 63
<211> LENGTH: 78
<212> TYPE: DNA
<213> ORGANISM: Artificial Sequence
<220> FEATURE:
<223> OTHER INFORMATION: primer P34

<400> SEQUENCE: 63
gatcagcact cccaacgcga aatagtttag aaacatattg ttcctcctgt gtgagctcac 60
aattccacac attatacg 78

<210> SEQ ID NO 64
<211> LENGTH: 64
<212> TYPE: DNA
<213> ORGANISM: Artificial Sequence
<220> FEATURE:
<223> OTHER INFORMATION: primer P35

<400> SEQUENCE: 64
tgccagccca aaaacaacac tgataaacgt gaatcccgct caagttagta taaaaaagct 60
gaac 64

<210> SEQ ID NO 65
<211> LENGTH: 20
<212> TYPE: DNA
<213> ORGANISM: Artificial Sequence
<220> FEATURE:
<223> OTHER INFORMATION: primer P36

<400> SEQUENCE: 65
tcgcccagat ccacagaaac 20

<210> SEQ ID NO 66
<211> LENGTH: 24
<212> TYPE: DNA
<213> ORGANISM: Artificial Sequence
<220> FEATURE:
<223> OTHER INFORMATION: primer P37

<400> SEQUENCE: 66
tgccttcgtc atacaatcgt tatg 24

<210> SEQ ID NO 67
<211> LENGTH: 64
<212> TYPE: DNA
<213> ORGANISM: Artificial Sequence
<220> FEATURE:
<223> OTHER INFORMATION: primer P38

<400> SEQUENCE: 67
attttgcttc ccccgctaac aatggcgaca tattatcgct caagttagta taaaaaagct 60
gaac 64

<210> SEQ ID NO 68
<211> LENGTH: 64
<212> TYPE: DNA

<213> ORGANISM: Artificial Sequence
<220> FEATURE:
<223> OTHER INFORMATION: primer P39

<400> SEQUENCE: 68
aaatcaatcg cttttcagca acacctcttc cagccatgaa gcctgctttt ttatactaag 60
ttgg 64

<210> SEQ ID NO 69
<211> LENGTH: 24
<212> TYPE: DNA
<213> ORGANISM: Artificial Sequence
<220> FEATURE:
<223> OTHER INFORMATION: primer P40

<400> SEQUENCE: 69
ctatttcatg ggggataaac cgac 24

<210> SEQ ID NO 70
<211> LENGTH: 24
<212> TYPE: DNA
<213> ORGANISM: Artificial Sequence
<220> FEATURE:
<223> OTHER INFORMATION: primer P41

<400> SEQUENCE: 70
cgcgtcttat catgcctacc aaac 24

<210> SEQ ID NO 71
<211> LENGTH: 64
<212> TYPE: DNA
<213> ORGANISM: Artificial Sequence
<220> FEATURE:
<223> OTHER INFORMATION: primer P42

<400> SEQUENCE: 71
gtaatattca cagggatcac tgtaattaaa ataaatcgct caagttagta taaaaaagct 60
gaac 64

<210> SEQ ID NO 72
<211> LENGTH: 64
<212> TYPE: DNA
<213> ORGANISM: Artificial Sequence
<220> FEATURE:
<223> OTHER INFORMATION: primer P43

<400> SEQUENCE: 72
gtggctaaca tccttatagc cactctgtag tattaatgaa gcctgctttt ttatactaag 60
ttgg 64

<210> SEQ ID NO 73
<211> LENGTH: 60
<212> TYPE: DNA
<213> ORGANISM: Artificial Sequence
<220> FEATURE:
<223> OTHER INFORMATION: primer P44

<400> SEQUENCE: 73
atgcgtctgg aagtcttttg tgaagaccga ctcggtctcg ctcaagttag tataaaaaag 60

<210> SEQ ID NO 74
<211> LENGTH: 56
<212> TYPE: DNA
<213> ORGANISM: Artificial Sequence
<220> FEATURE:
<223> OTHER INFORMATION: primer P45

<400> SEQUENCE: 74
ctcttcgttc ttcttctgac tcagaccata ttcccgagat cttgaagcct gctttt 56

<210> SEQ ID NO 75
<211> LENGTH: 63
<212> TYPE: DNA
<213> ORGANISM: Artificial Sequence
<220> FEATURE:
<223> OTHER INFORMATION: primer P46

<400> SEQUENCE: 75
tatggttgct gaattgaccg cattacgcga tcaaatcgct caagttagta taaaaaagct 60
gaa 63

<210> SEQ ID NO 76
<211> LENGTH: 63
<212> TYPE: DNA
<213> ORGANISM: Artificial Sequence
<220> FEATURE:
<223> OTHER INFORMATION: primer P47

<400> SEQUENCE: 76
ggcaacacta tgacatcgga aaacccgtta ctggcgtgaa gcctgctttt ttatactaag 60
ttg 63

<210> SEQ ID NO 77
<211> LENGTH: 32
<212> TYPE: DNA
<213> ORGANISM: Artificial Sequence
<220> FEATURE:
<223> OTHER INFORMATION: primer P48

<400> SEQUENCE: 77
gtgatctatt tgtttgctat atcttaattt tg 32

<210> SEQ ID NO 78
<211> LENGTH: 26
<212> TYPE: DNA
<213> ORGANISM: Artificial Sequence
<220> FEATURE:
<223> OTHER INFORMATION: primer P49

<400> SEQUENCE: 78
accaattact gtacctgcta taacca 26

<210> SEQ ID NO 79
<211> LENGTH: 15
<212> TYPE: DNA
<213> ORGANISM: Artificial Sequence
<220> FEATURE:
<223> OTHER INFORMATION: primer P50

<400> SEQUENCE: 79
cgcccgctgc cgtgg 15

<210> SEQ ID NO 80
<211> LENGTH: 22
<212> TYPE: DNA
<213> ORGANISM: Artificial Sequence
<220> FEATURE:
<223> OTHER INFORMATION: primer P51

<400> SEQUENCE: 80
gcgtgccgtt gtggttattg ac 22

<210> SEQ ID NO 81
<211> LENGTH: 19
<212> TYPE: DNA
<213> ORGANISM: Artificial Sequence
<220> FEATURE:
<223> OTHER INFORMATION: primer P52

<400> SEQUENCE: 81
agctgggaaa tgaccgatg 19

<210> SEQ ID NO 82
<211> LENGTH: 23
<212> TYPE: DNA
<213> ORGANISM: Artificial Sequence
<220> FEATURE:
<223> OTHER INFORMATION: primer P53

<400> SEQUENCE: 82
tcctttatat tgagtgtatc gcc 23

<210> SEQ ID NO 83
<211> LENGTH: 1613
<212> TYPE: DNA
<213> ORGANISM: Artificial Sequence
<220> FEATURE:
<223> OTHER INFORMATION: trp(L'-'B)E5

<400> SEQUENCE: 83
gtatcgacaa tgaaagcaat tttcgtactg aaaggtcgag ggaaatctg atgcaaacac 60 aaaaaccgac tctcgaactg ctaacctgcg aaggcgctta tcgcgacaat cccaccgcgc 120
tttttcacca gttgtgtggg gatcgtccgg caacgctgct gctgacatcc gcagatatcg 180
acagcaaaga tgatttaaaa agcctgctgc tggtagacag tgcgctgcgc attacagctt 240
taggtgacac tgtcacaatc caggcacttt ccggcaacgg cgaagccctc ctggcactac 300
tggataacgc cctgcctgcg ggtgtggaaa gtgaacaatc accaaactgc cgtgtgctgc 360
gcttcccccc tgtcagtcca ctgctggatg aagacgcccg cttatgctcc ctttcggttt 420
ttgacgcttt ccgtttattg cagaatctgt tgaatgtacc gaaggaagaa cgagaagcca 480
tgttcttcgg cggcctgttc tcttatgacc ttgtggcggg atttgaagat ttaccgcaac 540
tgtcagcgga aaataactgc cctgatttct gtttttatct cgctgaaacg ctgatggtga 600
ttgaccatca gaaaaaaagc acccgtattc aggccagcct gtttgctccg aatgaagaag 660
aaaaacaacg tctcactgct cgcctgaacg aactacgtca gcaactgacc gaagccgcgc 720
cgccgctgcc agtggtttcc gtgccgcata tgcgttgtga atgtaatcag agcgatgaag 780
agttcggtgg cgtagtgcgt ttgttgcaaa aagcgattcg cgctggagaa attttccagg 840
tggtgccatc tcgccgtttc tctctgccct gcccgtcacc gctggcggcc tattacgtgc 900
tgaaaaagag taatcccagc ccgtacatgt tttttatgca ggataatgat ttcaccctat 960
ttggcgcgtc gccggaaagc tcgctcaagt atgatgccac cagccgccag attgagatct 1020
acccgattgc cggaacacgc ccacgcggtc gtcgcgccga tggttcactg gacagagatc 1080
tcgacagccg tattgaactg gaaatgcgta ccgatcataa agagctgtct gaacatctga 1140
tgctggttga tctcgcccgt aatgatctgg cacgcatttg cacccccggc agccgctacg 1200
tcgccgatct caccaaagtt gaccgttatt cctatgtgat gcacctcgtc tctcgcgtag 1260

```
tcggcgaact gcgtcacgat cttgacgccc tgcacgctta tcgcgcctgt atgaatatgg   1320

ggacgttaag cggtgcgccg aaagtacgcg ctatgcagtt aattgccgag gcggaaggtc   1380

gtcgccgcgg cagctacggc ggcgcggtag gttatttcac cgcgcatggc gatctcgaca   1440

cctgcattgt gatccgctcg gcgctggtgg aaaacggtat cgccaccgtg caagcgggtg   1500

ctggtgtagt ccttgattct gttccgcagt cggaagccga cgaaacccgt aacaaagccc   1560

gcgctgtact gcgcgctatt gccaccgcgc atcatgcaca ggagactttc tga          1613
```

<210> SEQ ID NO 84
<211> LENGTH: 58
<212> TYPE: DNA
<213> ORGANISM: Artificial Sequence
<220> FEATURE:
<223> OTHER INFORMATION: primer P54

<400> SEQUENCE: 84

```
ttactctacc gttaaaatac gcgtggtatt cgctcaagtt agtataaaaa agctgaac       58
```

<210> SEQ ID NO 85
<211> LENGTH: 67
<212> TYPE: DNA
<213> ORGANISM: Artificial Sequence
<220> FEATURE:
<223> OTHER INFORMATION: primer P55

<400> SEQUENCE: 85

```
gcttcgcaga acaaaaatcg ttaccacgtt aggccctctt gaagcctgct tttttatact     60

aagttgg                                                               67
```

<210> SEQ ID NO 86
<211> LENGTH: 63
<212> TYPE: DNA
<213> ORGANISM: Artificial Sequence
<220> FEATURE:
<223> OTHER INFORMATION: primer P56

<400> SEQUENCE: 86

```
taatttcagc gtataatgcg cgccaattga ctctcttgaa gcctgctttt ttatactaag     60

ttg                                                                   63
```

<210> SEQ ID NO 87
<211> LENGTH: 63
<212> TYPE: DNA
<213> ORGANISM: Artificial Sequence
<220> FEATURE:
<223> OTHER INFORMATION: primer P57

<400> SEQUENCE: 87

```
ggtgttagta gtgccgctcg gtaccagtgc accagacgct caagttagta taaaaaagct     60

gaa                                                                   63
```

<210> SEQ ID NO 88
<211> LENGTH: 60
<212> TYPE: DNA
<213> ORGANISM: Artificial Sequence
<220> FEATURE:
<223> OTHER INFORMATION: primer P58

<400> SEQUENCE: 88

```
tcagcgcatt ccaccgtacg ccagcgtcac ttcctttgaa gcctgctttt ttatactaag     60
```

<210> SEQ ID NO 89
<211> LENGTH: 60
<212> TYPE: DNA
<213> ORGANISM: Artificial Sequence
<220> FEATURE:
<223> OTHER INFORMATION: primer P59

<400> SEQUENCE: 89
aatgaaaatg atttccacga tacagaaaaa agagaccgct caagttagta taaaaaagct 60

<210> SEQ ID NO 90
<211> LENGTH: 18
<212> TYPE: DNA
<213> ORGANISM: Artificial Sequence
<220> FEATURE:
<223> OTHER INFORMATION: primer P60

<400> SEQUENCE: 90
attaatttat cgccatcg 18

<210> SEQ ID NO 91
<211> LENGTH: 18
<212> TYPE: DNA
<213> ORGANISM: Artificial Sequence
<220> FEATURE:
<223> OTHER INFORMATION: primer P61

<400> SEQUENCE: 91
gataagttca agtttgct 18

<210> SEQ ID NO 92
<211> LENGTH: 23
<212> TYPE: DNA
<213> ORGANISM: Artificial Sequence
<220> FEATURE:
<223> OTHER INFORMATION: primer P62

<400> SEQUENCE: 92
aacaaaatca gacaaataac gcg 23

<210> SEQ ID NO 93
<211> LENGTH: 27
<212> TYPE: DNA
<213> ORGANISM: Artificial Sequence
<220> FEATURE:
<223> OTHER INFORMATION: primer P63

<400> SEQUENCE: 93
aaaattgaga gaaaacagga tgcttcc 27

<210> SEQ ID NO 94
<211> LENGTH: 19
<212> TYPE: DNA
<213> ORGANISM: Artificial Sequence
<220> FEATURE:
<223> OTHER INFORMATION: primer P64

<400> SEQUENCE: 94
tcagcgcatt ccaccgtac 19

<210> SEQ ID NO 95
<211> LENGTH: 17
<212> TYPE: DNA
<213> ORGANISM: Artificial Sequence
<220> FEATURE:
<223> OTHER INFORMATION: primer P65

```
<400> SEQUENCE: 95

gcggcgatca cttccgg                                                 17


<210> SEQ ID NO 96
<211> LENGTH: 78
<212> TYPE: DNA
<213> ORGANISM: Artificial Sequence
<220> FEATURE:
<223> OTHER INFORMATION: primer P66

<400> SEQUENCE: 96

tatcagccct atgagcgttg ctttttgtcg tgtcatattg ttcctcctgt gtgagctcac     60

aattccacac attatacg                                                78


<210> SEQ ID NO 97
<211> LENGTH: 63
<212> TYPE: DNA
<213> ORGANISM: Artificial Sequence
<220> FEATURE:
<223> OTHER INFORMATION: primer P67

<400> SEQUENCE: 97

ttaattttta acggcaagag agacaaaaca gcgagccgct caagttagta taaaaaagct     60

gaa                                                                63


<210> SEQ ID NO 98
<211> LENGTH: 20
<212> TYPE: DNA
<213> ORGANISM: Artificial Sequence
<220> FEATURE:
<223> OTHER INFORMATION: primer P68

<400> SEQUENCE: 98

cctcactgac accgcgaatc                                              20


<210> SEQ ID NO 99
<211> LENGTH: 18
<212> TYPE: DNA
<213> ORGANISM: Artificial Sequence
<220> FEATURE:
<223> OTHER INFORMATION: primer P69

<400> SEQUENCE: 99

gacctacctc aatagcgg                                                18
```